(12) United States Patent
Ting et al.

(10) Patent No.: US 7,687,462 B2
(45) Date of Patent: Mar. 30, 2010

(54) COMPOSITION FOR PROMOTING CARTILAGE FORMATION OR REPAIR COMPRISING A NELL GENE PRODUCT AND METHOD OF TREATING CARTILAGE-RELATED CONDITIONS USING SUCH COMPOSITION

(75) Inventors: Kang Ting, Beverly Hills, CA (US); Ben Wu, Los Angeles, CA (US); Chia Soo, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/594,510

(22) Filed: Nov. 7, 2006

(65) Prior Publication Data

US 2007/0134291 A1 Jun. 14, 2007

Related U.S. Application Data

(63) Continuation-in-part of application No. 10/527,786, filed as application No. PCT/US03/29281 on Sep. 15, 2003, now abandoned, application No. 11/594,510, which is a continuation-in-part of application No. 10/544,553, filed as application No. PCT/US2004/003808 on Feb. 9, 2004, now Pat. No. 7,544,486, application No. 11/594,510, which is a continuation-in-part of application No. PCT/US2006/005473, filed on Feb. 16, 2006, and a continuation-in-part of application No. 11/392,294, filed on Mar. 28, 2006, which is a continuation of application No. 09/412,297, filed on Oct. 5, 1999, now Pat. No. 7,052,856.

(60) Provisional application No. 60/410,846, filed on Sep. 13, 2002, provisional application No. 60/445,672, filed on Feb. 7, 2003, provisional application No. 60/653,722, filed on Feb. 16, 2005.

(51) Int. Cl.
| | |
|---|---|
| A61K 38/00 | (2006.01) |
| A61K 38/16 | (2006.01) |
| A61K 38/17 | (2006.01) |
| A61K 38/18 | (2006.01) |
| A61K 31/7088 | (2006.01) |
| A61K 31/7105 | (2006.01) |
| A61K 31/711 | (2006.01) |
| A61K 31/713 | (2006.01) |

(52) U.S. Cl. .................... 514/12; 514/2; 514/7; 514/8; 514/44

(58) Field of Classification Search .................. None
See application file for complete search history.

(56) References Cited

U.S. PATENT DOCUMENTS 4,394,370 A 7/1983 Jefferies (Continued)

FOREIGN PATENT DOCUMENTS

WO WO 01/24821 4/2001

(Continued)

OTHER PUBLICATIONS

Barron et al., 2007, J. Am. Osteopath. Assoc. 107(suppl 6):ES21-ES27.*

(Continued)

*Primary Examiner*—Elizabeth C. Kemmerer
(74) *Attorney, Agent, or Firm*—Squire, Sanders & Dempsey L.L.P.

(57) ABSTRACT

Provided herein is a composition for cartilage formation or regeneration comprising a NELL gene product and a method of treating cartilage-related conditions using such a composition.

8 Claims, 11 Drawing Sheets

Normal cartilage  Nell-1 overexpression cartilage

U.S. PATENT DOCUMENTS

| | | | |
|---|---|---|---|
| 4,409,332 | A | 10/1983 | Jefferies et al. |
| 5,385,887 | A | 1/1995 | Yim et al. |
| 5,486,359 | A | 1/1996 | Caplan et al. |
| 5,674,725 | A | 10/1997 | Beertsen et al. |
| 5,674,844 | A | 10/1997 | Kuberasampath et al. |
| 5,763,416 | A | 6/1998 | Bonadio et al. |
| 5,846,931 | A * | 12/1998 | Hattersley et al. .............. 514/2 |
| 5,854,207 | A | 12/1998 | Lee et al. |
| 5,916,870 | A | 6/1999 | Lee et al. |
| 5,942,496 | A | 8/1999 | Bonadio et al. |
| 5,948,428 | A | 9/1999 | Lee et al. |
| 6,077,987 | A | 6/2000 | Breitbart et al. |
| 6,083,690 | A | 7/2000 | Harris et al. |
| 6,200,606 | B1 | 3/2001 | Peterson et al. |
| 6,352,972 | B1 | 3/2002 | Nimni et al. |
| 6,413,998 | B1 | 7/2002 | Petrie et al. |
| 6,462,019 | B1 | 10/2002 | Mundy et al. |
| 2003/0143688 | A1 | 7/2003 | Fujiwara et al. |
| 2006/0053503 | A1* | 3/2006 | Culiat et al. .................. 800/18 |

FOREIGN PATENT DOCUMENTS

| | | |
|---|---|---|
| WO | WO 2004/024893 | 3/2004 |

OTHER PUBLICATIONS

"Prevent." Compact Oxford English Dictionary, www.AskOxford.com, accessed Jun. 19, 2008.*

Chiang et al., 2009, J. Formos. Med. Assoc. 108(2): 87-101.*

International Search Report for PCT/US04/03808 filed Feb. 9, 2004, mailed Sep. 19, 2006, 9 pgs.

Beck et al. "Rapid Publication TGF-$\beta_1$ Induces Bone Closure of Skull Defects." J. of *Bone Miner. Res.* vol. 6, No. 11:1257-1265 (1991).

Bellows et al. "Determination of Numbers of Osteoprogenitors Present in Isolated Fetal Rat Calvaria Cells in Vitro." Dev. Biol. 133, pp. 8-13 (1989).

Burger et al., "Osteoblast and Osteoclast Precursors in Primary Cultures of Calvarial Bone Cells." Anat. Rec. Jan. 1986; 214(1): 32-40. Abstract only.

Chen et al. "Structure, Chromosomal Localization, and Expression Pattern of the Murine *Magp* Gene," J. Biol Chem. vol. 268, No. 36: 27381-27389 (1998).

Crawford et al. "Thrombospondin-1 is a Major Activator of TGF-$\beta_1$ in Vivo." Cell, vol. 93:1159-1170 (1998).

Francois and Bier "Xenopus chordin and Drosophila short gastrulation Genes Encode Homologous Proteins Functioning in Dorsal-Ventral Axis Formation" Cell, vol. 80:19-20 (1995).

Gelbart, "Databases in Genomic Research" Science, vol. 282, Oct. 23, 1998.

Hoshi, K. et al., "Fibroblasts of Spinal Ligaments Pathologically Differentiate into Chondrocytes Induced by Recombinant Human Bone Morphogenetic Protein-2: Morphological Examinations for Ossification and Spinal Ligaments" Bone vol. 21, No. 2:155-162 (1997).

Kim et al. "NELL-1 Enhances Mineralization in Fetal Calvarial Osteoblastic Cells." Plastic Surgery, 599-601 (1999).

Kuroda and Tanizawa "Involvement of Epidermal Growth Factor-like Domain of NELL Proteins in the Novel Protein-Protein Interaction with Protein Kinase C[1]" Biochem Biophys Res. Commun. 265: 752-757 (1999).

Kuroda et al. "Biochemical Characterization and Expression Analysis of Neural Thrombospondin-1-like Proteins NELL1 and NELL2" Biochem Biophys Res Comm. 265: 79-86 (1999).

Luce and Burrows "The neuronal EGF-related genes NELL1 and NELL2 are expressed in hemopoietic cells and developmentally regulated in the B lineage" *Gene* 231:121-126 (1999).

Opperman, et al., "TGF-$\beta$1, TGF-$\beta$2, and TGF-$\beta$3 Exhbit Distinct Patterns of Expression During Cranial Suture Formation and Obliteration in Vivo and in Vitro" J. of Bone and Mineral Research, vol. 12, No. 3: 301-310 (1997).

Piccolo et al. "Dorsoventral Patterning in Xenopus: Inhibition of Ventral Signals by Direct Binding of Chordin to BMP-4" Cell, vol. 86: 589-598 (1996).

Siris et al., "Design of NORA, the National Osteoporosis Risk Assessment program: A Longitudinal US Registry of Postmenopausal Women" Osteoporos Int. Suppl. 1: 62-69 (1998).

Takagi et al. "The reaction of the dura to bone morphogenetic protein (BMP) in repair of skull defects" Ann Surg. vol. 196, No. 1:100-109. Abstract only (1982).

Takami et al. "$Ca^{2+}$-ATPase Inhibitors and $Ca^{2+}$-Ionophore Induce Osteoclast-like Cell Formation in the Cocultures of Mouse Bone Marrow Cells and Calvarial Cells" Biochemical and Biophysical Research Comm, vol. 237: 111-115 1997.

Tieu A. et al. "Identification of Human NEL-2 Associated with Premature Suture Fusion." J Dent Res. 77(A):635, Abstract only (1998).

Ting et al. "Human NELL1 Expressed in Unilaterial Coronal Synostosis" J. of Bone and Mineral Res. vol. 14: 80-89 (1999).

Ting et al. "NELL-1 Enhances Mineralization in Fetal Calvarial Osteoblastic Cells." *J. Dent. Res.* 79:625 (2000).

Ting et al. "NEL-2 Expressed in Unilateral Prematurely Fusing and Fused Coronal Sutures." J Dent Res. 77(B):2224 (1998) Abstract only.

Ting et al. "NEL-2 Gene is associated with bone formation in Craniosynostosis", Plastic Surgery, 602-603 (no date).

Toriumi et al. "Mandibular Reconstruction With a Recombinant Bone-Inducing Factor." Arch. Otolaryngol. Head Neck Surg. vol. 117: 1101-1112 (1991).

Watanabe, T.K. et al. "Cloning and Characterization of Two Novel Human cDNAs (NELL1 and NELL2) Encoding Proteins with Six EGF-like Repeats." Genomics, vol. 38, 273-276 (1996).

Wobus, "Potential of embryonic stem cells" Molecular Aspects of Medicine (2001), 22/3 (149-164) (Abstract only) 1 pg.

Yasko et al. "The Healing of Segmental Bone Defects, Induced by Recombinant Human Bone Morphogenetic Protein (rhBMP-2)." J. of Bone and Joint Surgery vol. 74A, No. 5: 659-670 (1992).

Zhang et al., "Graniosynostosis in transgenic mice overexpressing Nell-1" The J. of Clinical Investigation, vol. 110, No. 6 (2002).

Liu et al., "Simultaneous Detection of Multiple Bone-Related mRNAs and Protein Expression during Osteoblast Differentiation: Polymerase Chain Reaction and Immunocytochemical Studies at the Single Cell Level", Development Biology, vol. 166, pp. 220-234 (1994).

Zhang et al., "NELL-1 Overexpression Transgenic Mice Stimulate Human Craniosynostosis", Surgical Forum, vol. 52, pp. 576-578 (2001).

International Search Report for PCT/US2008/054779, mailed Aug. 1, 2008, 11 pgs.

Aghaloo et al., "Nell-1-induced bone regeneration in calvarial defects", Am. J. Pathol., vol. 169, pp. 903-915 (2006).

Cowan et al., "Nell-1 induced bone formation within the distracted intermaxillary suture", Bone, vol. 38, pp. 48-58 (2006).

Lu et al., "The osteoinductive properties of Nell-1 in a rat spinal fusion model", The Spine J. vol. 7, No. 1, pp. 50-60 (2007).

* cited by examiner

Normal cartilage    Nell-1 overexpression cartilage

A

B           AdNell-1        AdBMP-2        AdLacZ

Nell-1 actin

SEQUENCE LISTING

```
<160> NUMBER OF SEQ ID NOS: 14

<210> SEQ ID NO 1
<211> LENGTH: 2433
<212> TYPE: DNA
<213> ORGANISM: Homo sapiens
<220> FEATURE:
<221> NAME/KEY: CDS
<222> LOCATION: (1)...(2433)

<400> SEQUENCE: 1 atg ccg atg gat ttg att tta gtt gtg tgg ttc tgt gtg tgc act gcc      48
Met Pro Met Asp Leu Ile Leu Val Val Trp Phe Cys Val Cys Thr Ala
 1               5                  10                  15 agg aca gtg gtg ggc ttt ggg atg gac cct gac ctt cag atg gat atc      96
Arg Thr Val Val Gly Phe Gly Met Asp Pro Asp Leu Gln Met Asp Ile
             20                  25                  30 gtc acc gag ctt gac ctt gtg aac acc acc ctt gga gtt gct cag gtg     144
Val Thr Glu Leu Asp Leu Val Asn Thr Thr Leu Gly Val Ala Gln Val
         35                  40                  45
```

```
tct gga atg cac aat gcc agc aaa gca ttt tta ttt caa gac ata gaa    192
Ser Gly Met His Asn Ala Ser Lys Ala Phe Leu Phe Gln Asp Ile Glu
 50                  55                  60 aga gag atc cat gca gct cct cat gtg agt gag aaa tta att cag ctg    240
Arg Glu Ile His Ala Ala Pro His Val Ser Glu Lys Leu Ile Gln Leu
 65                  70                  75                  80 ttc cag aac aag agt gaa ttc acc att ttg gcc act gta cag cag aag    288
Phe Gln Asn Lys Ser Glu Phe Thr Ile Leu Ala Thr Val Gln Gln Lys
                 85                  90                  95 cca tcc act tca gga gtg ata ctg tcc att cga gaa ctg gag cac agc    336
Pro Ser Thr Ser Gly Val Ile Leu Ser Ile Arg Glu Leu Glu His Ser
            100                 105                 110 tat ttt gaa ctg gag agc agt ggc ctg agg gat gag att cgg tat cac    384
Tyr Phe Glu Leu Glu Ser Ser Gly Leu Arg Asp Glu Ile Arg Tyr His
        115                 120                 125 tac ata cac aat ggg aag cca agg aca gag gca ctt cct tac cgc atg    432
Tyr Ile His Asn Gly Lys Pro Arg Thr Glu Ala Leu Pro Tyr Arg Met
130                 135                 140 gca gat gga caa tgg cac aag gtt gca ctg tca gtt agc gcc tct cat    480
Ala Asp Gly Gln Trp His Lys Val Ala Leu Ser Val Ser Ala Ser His
145                 150                 155                 160 ctc ctg ctc cat gtc gac tgt aac agg att tat gag cgt gtg ata gac    528
Leu Leu Leu His Val Asp Cys Asn Arg Ile Tyr Glu Arg Val Ile Asp
                165                 170                 175 cct cca gat acc aac ctt ccc cca gga atc aat tta tgg ctt ggc cag    576
Pro Pro Asp Thr Asn Leu Pro Pro Gly Ile Asn Leu Trp Leu Gly Gln
            180                 185                 190 cgc aac caa aag cat ggc tta ttc aaa ggg atc atc caa gat ggg aag    624
Arg Asn Gln Lys His Gly Leu Phe Lys Gly Ile Ile Gln Asp Gly Lys
        195                 200                 205 atc atc ttt atg ccg aat gga tat ata aca cag tgt cca aat cta aat    672
Ile Ile Phe Met Pro Asn Gly Tyr Ile Thr Gln Cys Pro Asn Leu Asn
210                 215                 220 cac act tgc cca acc tgc agt gat ttc tta agc ctg gtg caa gga ata    720
His Thr Cys Pro Thr Cys Ser Asp Phe Leu Ser Leu Val Gln Gly Ile
225                 230                 235                 240 atg gat tta caa gag ctt ttg gcc aag atg act gca aaa cta aat tat    768
Met Asp Leu Gln Glu Leu Leu Ala Lys Met Thr Ala Lys Leu Asn Tyr
                245                 250                 255 gca gag aca aga ctt agt caa ttg gaa aac tgt cat tgt gag aag act    816
Ala Glu Thr Arg Leu Ser Gln Leu Glu Asn Cys His Cys Glu Lys Thr
            260                 265                 270 tgt caa gtg agt gga ctg ctc tat cga gat caa gac tct tgg gta gat    864
Cys Gln Val Ser Gly Leu Leu Tyr Arg Asp Gln Asp Ser Trp Val Asp
        275                 280                 285 ggt gac cat tgc agg aac tgc act tgc aaa agt ggt gcc gtg gaa tgc    912
Gly Asp His Cys Arg Asn Cys Thr Cys Lys Ser Gly Ala Val Glu Cys
290                 295                 300 cga agg atg tcc tgt ccc cct ctc aat tgc tcc cca gac tcc ctc cca    960
Arg Arg Met Ser Cys Pro Pro Leu Asn Cys Ser Pro Asp Ser Leu Pro
305                 310                 315                 320 gta cac att gct ggc cag tgc tgt aag gtc tgc cga cca aaa tgt atc   1008
Val His Ile Ala Gly Gln Cys Cys Lys Val Cys Arg Pro Lys Cys Ile
                325                 330                 335 tat gga gga aaa gtt ctt gca gaa ggc cag cgg att tta acc aag agc   1056
Tyr Gly Gly Lys Val Leu Ala Glu Gly Gln Arg Ile Leu Thr Lys Ser
            340                 345                 350 tgt cgg gaa tgc cga ggt gga gtt tta gta aaa att aca gaa atg tgt   1104
Cys Arg Glu Cys Arg Gly Gly Val Leu Val Lys Ile Thr Glu Met Cys
        355                 360                 365
```

-continued

```
cct cct ttg aac tgc tca gaa aag gat cac att ctt cct gag aat cag    1152
Pro Pro Leu Asn Cys Ser Glu Lys Asp His Ile Leu Pro Glu Asn Gln
        370                 375                 380 tgc tgc cgt gtc tgt aga ggt cat aac ttt tgt gca gaa gga cct aaa    1200
Cys Cys Arg Val Cys Arg Gly His Asn Phe Cys Ala Glu Gly Pro Lys
385                 390                 395                 400 tgt ggt gaa aac tca gag tgc aaa aac tgg aat aca aaa gct act tgt    1248
Cys Gly Glu Asn Ser Glu Cys Lys Asn Trp Asn Thr Lys Ala Thr Cys
                405                 410                 415 gag tgc aag agt ggt tac atc tct gtc cag gga gac tct gcc tac tgt    1296
Glu Cys Lys Ser Gly Tyr Ile Ser Val Gln Gly Asp Ser Ala Tyr Cys
        420                 425                 430 gaa gat att gat gag tgt gca gct aag atg cat tac tgt cat gcc aat    1344
Glu Asp Ile Asp Glu Cys Ala Ala Lys Met His Tyr Cys His Ala Asn
435                 440                 445 act gtg tgt gtc aac ctt cct ggg tta tat cgc tgt gac tgt gtc cca    1392
Thr Val Cys Val Asn Leu Pro Gly Leu Tyr Arg Cys Asp Cys Val Pro
                450                 455                 460 gga tac att cgt gtg gat gac ttc tct tgt aca gaa cac gat gaa tgt    1440
Gly Tyr Ile Arg Val Asp Asp Phe Ser Cys Thr Glu His Asp Glu Cys
465                 470                 475                 480 ggc agc ggc cag cac aac tgt gat gag aat gcc atc tgc acc aac act    1488
Gly Ser Gly Gln His Asn Cys Asp Glu Asn Ala Ile Cys Thr Asn Thr
        485                 490                 495 gtc cag gga cac agc tgc acc tgc aaa ccg ggc tac gtg ggg aac ggg    1536
Val Gln Gly His Ser Cys Thr Cys Lys Pro Gly Tyr Val Gly Asn Gly
                500                 505                 510 acc atc tgc aga gct ttc tgt gaa gag ggc tgc aga tac ggt gga acg    1584
Thr Ile Cys Arg Ala Phe Cys Glu Glu Gly Cys Arg Tyr Gly Gly Thr
        515                 520                 525 tgt gtg gct ccc aac aaa tgt gtc tgt cca tct gga ttc aca gga agc    1632
Cys Val Ala Pro Asn Lys Cys Val Cys Pro Ser Gly Phe Thr Gly Ser
530                 535                 540 cac tgc gag aaa gat att gat gaa tgt tca gag gga atc att gag tgc    1680
His Cys Glu Lys Asp Ile Asp Glu Cys Ser Glu Gly Ile Ile Glu Cys
545                 550                 555                 560 cac aac cat tcc cgc tgc gtt aac ctg cca ggg tgg tac cac tgt gag    1728
His Asn His Ser Arg Cys Val Asn Leu Pro Gly Trp Tyr His Cys Glu
                565                 570                 575 tgc aga agc ggt ttc cat gac gat ggg acc tat tca ctg tcc ggg gag    1776
Cys Arg Ser Gly Phe His Asp Asp Gly Thr Tyr Ser Leu Ser Gly Glu
        580                 585                 590 tcc tgt att gac att gat gaa tgt gcc tta aga act cac acc tgt tgg    1824
Ser Cys Ile Asp Ile Asp Glu Cys Ala Leu Arg Thr His Thr Cys Trp
                595                 600                 605 aac gat tct gcc tgc atc aac ctg gca ggg ggt ttt gac tgt ctc tgc    1872
Asn Asp Ser Ala Cys Ile Asn Leu Ala Gly Gly Phe Asp Cys Leu Cys
610                 615                 620 ccc tct ggg ccc tcc tgc tct ggt gac tgt cct cat gaa ggg ggg ctg    1920
Pro Ser Gly Pro Ser Cys Ser Gly Asp Cys Pro His Glu Gly Gly Leu
625                 630                 635                 640 aag cac aat ggc cag gtg tgg acc ttg aaa gaa gac agg tgt tct gtc    1968
Lys His Asn Gly Gln Val Trp Thr Leu Lys Glu Asp Arg Cys Ser Val
                645                 650                 655 tgc tcc tgc aag gat ggc aag ata ttc tgc cga cgg aca gct tgt gat    2016
Cys Ser Cys Lys Asp Gly Lys Ile Phe Cys Arg Arg Thr Ala Cys Asp
        660                 665                 670 tgc cag aat cca agt gct gac cta ttc tgt tgc cca gaa tgt gac acc    2064
Cys Gln Asn Pro Ser Ala Asp Leu Phe Cys Cys Pro Glu Cys Asp Thr
```

-continued

```
aga gtc aca agt caa tgt tta gac caa aat ggt cac aag ctg tat cga    2112
Arg Val Thr Ser Gln Cys Leu Asp Gln Asn Gly His Lys Leu Tyr Arg
        690                 695                 700 agt gga gac aat tgg acc cat agc tgt cag cag tgt cgg tgt ctg gaa    2160
Ser Gly Asp Asn Trp Thr His Ser Cys Gln Gln Cys Arg Cys Leu Glu
705                 710                 715                 720 gga gag gta gat tgc tgg cca ctc act tgc ccc aac ttg agc tgt gag    2208
Gly Glu Val Asp Cys Trp Pro Leu Thr Cys Pro Asn Leu Ser Cys Glu
                725                 730                 735 tat aca gct atc tta gaa ggg gaa tgt tgt ccc cgc tgt gtc agt gac    2256
Tyr Thr Ala Ile Leu Glu Gly Glu Cys Cys Pro Arg Cys Val Ser Asp
            740                 745                 750 ccc tgc cta gct gat aac atc acc tat gac atc aga aaa act tgc ctg    2304
Pro Cys Leu Ala Asp Asn Ile Thr Tyr Asp Ile Arg Lys Thr Cys Leu
        755                 760                 765 gac agc tat ggt gtt tca cgg ctt agt ggc tca gtg tgg acg atg gct    2352
Asp Ser Tyr Gly Val Ser Arg Leu Ser Gly Ser Val Trp Thr Met Ala
770                 775                 780 gga tct ccc tgc aca acc tgt aaa tgc aag aat gga aga gtc tgt tgt    2400
Gly Ser Pro Cys Thr Thr Cys Lys Cys Lys Asn Gly Arg Val Cys Cys
785                 790                 795                 800 tct gtg gat ttt gag tgt ctt caa aat aat tga                        2433
Ser Val Asp Phe Glu Cys Leu Gln Asn Asn  *
                805                 810
```

<210> SEQ ID NO 2
<211> LENGTH: 810
<212> TYPE: PRT
<213> ORGANISM: Homo sapiens

<400> SEQUENCE: 2

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Gln Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
```

-continued

```
            195                 200                 205
Ile Ile Phe Met Pro Asn Gly Tyr Ile Thr Gln Cys Pro Asn Leu Asn
    210                 215                 220
His Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Ser Gln Leu Glu Asn Cys His Cys Glu Lys Thr
            260                 265                 270
Cys Gln Val Ser Gly Leu Leu Tyr Arg Asp Gln Asp Ser Trp Val Asp
        275                 280                 285
Gly Asp His Cys Arg Asn Cys Thr Cys Lys Ser Gly Ala Val Glu Cys
    290                 295                 300
Arg Arg Met Ser Cys Pro Pro Leu Asn Cys Ser Pro Asp Ser Leu Pro
305                 310                 315                 320
Val His Ile Ala Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Ser
            340                 345                 350
Cys Arg Glu Cys Arg Gly Gly Val Leu Val Lys Ile Thr Glu Met Cys
        355                 360                 365
Pro Pro Leu Asn Cys Ser Glu Lys Asp His Ile Leu Pro Glu Asn Gln
    370                 375                 380
Cys Cys Arg Val Cys Arg Gly His Asn Phe Cys Ala Glu Gly Pro Lys
385                 390                 395                 400
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
```

```
Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
            645                 650                 655

Cys Ser Cys Lys Asp Gly Lys Ile Phe Cys Arg Arg Thr Ala Cys Asp
        660                 665                 670

Cys Gln Asn Pro Ser Ala Asp Leu Phe Cys Pro Gly Cys Asp Thr
    675                 680                 685

Arg Val Thr Ser Gln Cys Leu Asp Gln Asn Gly His Lys Leu Tyr Arg
    690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
            725                 730                 735

Tyr Thr Ala Ile Leu Glu Gly Glu Cys Cys Pro Arg Cys Val Ser Asp
        740                 745                 750

Pro Cys Leu Ala Asp Asn Ile Thr Tyr Asp Ile Arg Lys Thr Cys Leu
    755                 760                 765

Asp Ser Tyr Gly Val Ser Arg Leu Ser Gly Ser Val Trp Thr Met Ala
770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
            805                 810

<210> SEQ ID NO 3
<211> LENGTH: 2433
<212> TYPE: DNA
<213> ORGANISM: Rattus norvegicus
<220> FEATURE:
<221> NAME/KEY: CDS
<222> LOCATION: (1)...(2433)

<400> SEQUENCE: 3 atg ccg atg gat gtg att tta gtt ttg tgg ttc tgt gta tgc acc gcc     48
Met Pro Met Asp Val Ile Leu Val Leu Trp Phe Cys Val Cys Thr Ala
1               5                   10                  15 agg aca gtg ttg ggc ttt ggg atg gac cct gac ctt cag ctg gac atc     96
Arg Thr Val Leu Gly Phe Gly Met Asp Pro Asp Leu Gln Leu Asp Ile
            20                  25                  30 atc tca gag ctc gac ctg gtg aac acc acc ctg gga gtc acg cag gtg    144
Ile Ser Glu Leu Asp Leu Val Asn Thr Thr Leu Gly Val Thr Gln Val
        35                  40                  45 gct gga ctg cac aac gcc agt aaa gca ttt cta ttt caa gat gta cag    192
Ala Gly Leu His Asn Ala Ser Lys Ala Phe Leu Phe Gln Asp Val Gln
    50                  55                  60 aga gag atc cat tcg gcc cct cac gtg agt gag aag ctg atc cag cta    240
Arg Glu Ile His Ser Ala Pro His Val Ser Glu Lys Leu Ile Gln Leu
65                  70                  75                  80 ttc cgg aat aag agc gag ttc acc ttt ttg gct aca gtg cag cag aaa    288
Phe Arg Asn Lys Ser Glu Phe Thr Phe Leu Ala Thr Val Gln Gln Lys
                85                  90                  95 cca tcc acc tca ggg gtg ata ctg tcc atc cgg gag ctg gag cac agc    336
Pro Ser Thr Ser Gly Val Ile Leu Ser Ile Arg Glu Leu Glu His Ser
            100                 105                 110 tat ttt gaa ctg gag agc agt ggc cca aga gaa gag ata cgc tac cat    384
Tyr Phe Glu Leu Glu Ser Ser Gly Pro Arg Glu Glu Ile Arg Tyr His
        115                 120                 125
```

-continued

```
tac ata cat ggt gga aag ccc agg act gag gcc ctt ccc tac cgc atg      432
Tyr Ile His Gly Gly Lys Pro Arg Thr Glu Ala Leu Pro Tyr Arg Met
        130                 135                 140 gca gac gga caa tgg cac aag gtc gcg ctg tca gtg agc gcc tct cac      480
Ala Asp Gly Gln Trp His Lys Val Ala Leu Ser Val Ser Ala Ser His
145                 150                 155                 160 ctc ctg ctc cac atc gac tgc aat agg att tac gag cgt gtg ata gac      528
Leu Leu Leu His Ile Asp Cys Asn Arg Ile Tyr Glu Arg Val Ile Asp
                165                 170                 175 cct ccg gag acc aac ctt cct cca gga agc aat ctg tgg ctt ggg caa      576
Pro Pro Glu Thr Asn Leu Pro Pro Gly Ser Asn Leu Trp Leu Gly Gln
            180                 185                 190 cgt aac caa aag cat ggc ttt ttc aaa gga atc atc caa gat ggt aag      624
Arg Asn Gln Lys His Gly Phe Phe Lys Gly Ile Ile Gln Asp Gly Lys
        195                 200                 205 atc atc ttc atg ccg aat ggt ttc atc aca cag tgt ccc aac ctc aat      672
Ile Ile Phe Met Pro Asn Gly Phe Ile Thr Gln Cys Pro Asn Leu Asn
    210                 215                 220 cgc act tgc cca aca tgc agt gac ttc ctg agc ctg gtt caa gga ata      720
Arg Thr Cys Pro Thr Cys Ser Asp Phe Leu Ser Leu Val Gln Gly Ile
225                 230                 235                 240 atg gat ttg caa gag ctt ttg gcc aag atg act gca aaa ctg aat tat      768
Met Asp Leu Gln Glu Leu Leu Ala Lys Met Thr Ala Lys Leu Asn Tyr
                245                 250                 255 gca gag acg aga ctt ggt caa ctg gaa aat tgc cac tgt gag aag acc      816
Ala Glu Thr Arg Leu Gly Gln Leu Glu Asn Cys His Cys Glu Lys Thr
            260                 265                 270 tgc caa gtg agt ggg ctc ctc tac agg gac caa gac tcc tgg gtg gat      864
Cys Gln Val Ser Gly Leu Leu Tyr Arg Asp Gln Asp Ser Trp Val Asp
        275                 280                 285 ggt gac aac tgt ggg aac tgc acg tgc aaa agt ggt gcc gtg gag tgc      912
Gly Asp Asn Cys Gly Asn Cys Thr Cys Lys Ser Gly Ala Val Glu Cys
    290                 295                 300 cgc agg atg tcc tgt ccc ccg ctc aac tgt tcc ccg gac tca ctt cct      960
Arg Arg Met Ser Cys Pro Pro Leu Asn Cys Ser Pro Asp Ser Leu Pro
305                 310                 315                 320 gtg cac att tcc ggc cag tgt tgt aaa gtt tgc aga cca aaa tgt atc     1008
Val His Ile Ser Gly Gln Cys Cys Lys Val Cys Arg Pro Lys Cys Ile
                325                 330                 335 tat gga gga aaa gtt ctt gct gag ggc cag cgg att tta acc aag acc     1056
Tyr Gly Gly Lys Val Leu Ala Glu Gly Gln Arg Ile Leu Thr Lys Thr
            340                 345                 350 tgc cgg gaa tgt cga ggt gga gtc ttg gta aaa atc aca gaa gct tgc     1104
Cys Arg Glu Cys Arg Gly Gly Val Leu Val Lys Ile Thr Glu Ala Cys
        355                 360                 365 cct cct ttg aac tgc tca gca aag gat cat att ctt cca gag aat cag     1152
Pro Pro Leu Asn Cys Ser Ala Lys Asp His Ile Leu Pro Glu Asn Gln
    370                 375                 380 tgc tgc agg gtc tgc cca ggt cat aac ttc tgt gca gaa gca cct aag     1200
Cys Cys Arg Val Cys Pro Gly His Asn Phe Cys Ala Glu Ala Pro Lys
385                 390                 395                 400 tgc gga gaa aac tcg gaa tgc aaa aat tgg aat aca aaa gca acc tgt     1248
Cys Gly Glu Asn Ser Glu Cys Lys Asn Trp Asn Thr Lys Ala Thr Cys
                405                 410                 415 gag tgc aag aat gga tac atc tct gtc cag ggc aac tct gca tac tgt     1296
Glu Cys Lys Asn Gly Tyr Ile Ser Val Gln Gly Asn Ser Ala Tyr Cys
            420                 425                 430 gaa gat att gat gag tgt gca gct aaa atg cac tat tgt cat gcc aac     1344
Glu Asp Ile Asp Glu Cys Ala Ala Lys Met His Tyr Cys His Ala Asn
```

-continued

|     |     |     | 435 |     |     |     |     | 440 |     |     |     |     | 445 |     |     |      |
|-----|-----|-----|-----|-----|-----|-----|-----|-----|-----|-----|-----|-----|-----|-----|-----|------|
| acc | gtg | tgt | gtc | aac | ttg | ccg | ggg | ttg | tat | cgc | tgt | gac | tgc | gtc | cca | 1392 |
| Thr | Val | Cys | Val | Asn | Leu | Pro | Gly | Leu | Tyr | Arg | Cys | Asp | Cys | Val | Pro |      |
|     | 450 |     |     |     |     | 455 |     |     |     |     | 460 |     |     |     |     |      |

```
ggg tac atc cgt gtg gat gac ttc tct tgt acg gag cat gat gat tgt    1440
Gly Tyr Ile Arg Val Asp Asp Phe Ser Cys Thr Glu His Asp Asp Cys
465                 470                 475                 480 ggc agc gga caa cac aac tgc gac aaa aat gcc atc tgt acc aac aca    1488
Gly Ser Gly Gln His Asn Cys Asp Lys Asn Ala Ile Cys Thr Asn Thr
                485                 490                 495 gtc cag gga cac agc tgc acc tgc cag ccg ggt tac gtg gga aat ggc    1536
Val Gln Gly His Ser Cys Thr Cys Gln Pro Gly Tyr Val Gly Asn Gly
            500                 505                 510 acc atc tgc aaa gca ttc tgt gaa gag ggt tgc aga tac gga ggt acc    1584
Thr Ile Cys Lys Ala Phe Cys Glu Glu Gly Cys Arg Tyr Gly Gly Thr
        515                 520                 525 tgt gtg gct cct aac aag tgt gtc tgt cct tct gga ttc acg gga agc    1632
Cys Val Ala Pro Asn Lys Cys Val Cys Pro Ser Gly Phe Thr Gly Ser
    530                 535                 540 cac tgt gag aaa gat att gat gaa tgc gca gag gga ttc gtt gaa tgc    1680
His Cys Glu Lys Asp Ile Asp Glu Cys Ala Glu Gly Phe Val Glu Cys
545                 550                 555                 560 cac aac tac tcc cgc tgt gtt aac ctg cca ggg tgg tac cac tgt gag    1728
His Asn Tyr Ser Arg Cys Val Asn Leu Pro Gly Trp Tyr His Cys Glu
                565                 570                 575 tgc aga agc ggt ttc cat gac gat ggg acc tac tca ctg tcc ggg gag    1776
Cys Arg Ser Gly Phe His Asp Asp Gly Thr Tyr Ser Leu Ser Gly Glu
            580                 585                 590 tcc tgc att gat atc gat gaa tgt gcc tta aga act cac act tgt tgg    1824
Ser Cys Ile Asp Ile Asp Glu Cys Ala Leu Arg Thr His Thr Cys Trp
        595                 600                 605 aat gac tct gcc tgc atc aac tta gca gga gga ttt gac tgc ctg tgt    1872
Asn Asp Ser Ala Cys Ile Asn Leu Ala Gly Gly Phe Asp Cys Leu Cys
    610                 615                 620 ccc tct ggg ccc tcc tgc tct ggt gac tgt ccc cac gaa gga ggg ctg    1920
Pro Ser Gly Pro Ser Cys Ser Gly Asp Cys Pro His Glu Gly Gly Leu
625                 630                 635                 640 aag cat aat ggg cag gtg tgg att ctg aga gaa gac agg tgt tca gtc    1968
Lys His Asn Gly Gln Val Trp Ile Leu Arg Glu Asp Arg Cys Ser Val
                645                 650                 655 tgt tcc tgc aag gat ggg aag ata ttc tgc cgg cgg aca gct tgt gat    2016
Cys Ser Cys Lys Asp Gly Lys Ile Phe Cys Arg Arg Thr Ala Cys Asp
            660                 665                 670 tgc cag aat cca aat gtt gac ctt ttt tgc tgc cca gag tgc gat acc    2064
Cys Gln Asn Pro Asn Val Asp Leu Phe Cys Cys Pro Glu Cys Asp Thr
        675                 680                 685 agg gtc acc agc caa tgt tta gat caa agt gga cag aag ctc tat cga    2112
Arg Val Thr Ser Gln Cys Leu Asp Gln Ser Gly Gln Lys Leu Tyr Arg
    690                 695                 700 agt gga gac aac tgg acc cac agc tgc cag cag tgc cga tgt ctg gaa    2160
Ser Gly Asp Asn Trp Thr His Ser Cys Gln Gln Cys Arg Cys Leu Glu
705                 710                 715                 720 gga gag gca gac tgc tgg cct ctg gct tgc cct agt ttg ggc tgt gaa    2208
Gly Glu Ala Asp Cys Trp Pro Leu Ala Cys Pro Ser Leu Gly Cys Glu
                725                 730                 735 tac aca gcc atg ttt gaa ggg gag tgt tgt ccc cga tgt gtc agt gac    2256
Tyr Thr Ala Met Phe Glu Gly Glu Cys Cys Pro Arg Cys Val Ser Asp
            740                 745                 750 ccc tgc ctg gct ggt aat att gcc tat gac atc aga aaa act tgc ctg    2304
```

```
Pro Cys Leu Ala Gly Asn Ile Ala Tyr Asp Ile Arg Lys Thr Cys Leu
        755                 760                 765 gac agc ttt ggt gtt tcg agg ctg agc gga gcc gtg tgg aca atg gct    2352
Asp Ser Phe Gly Val Ser Arg Leu Ser Gly Ala Val Trp Thr Met Ala
        770                 775                 780 gga tct cct tgt aca acc tgc aaa tgc aag aat ggg aga gtc tgc tgc    2400
Gly Ser Pro Cys Thr Thr Cys Lys Cys Lys Asn Gly Arg Val Cys Cys
785                 790                 795                 800 tct gtg gat ctg gag tgt att gag aat aac tga                        2433
Ser Val Asp Leu Glu Cys Ile Glu Asn Asn  *
                805                 810

<210> SEQ ID NO 4
<211> LENGTH: 810
<212> TYPE: PRT
<213> ORGANISM: Rattus norvegicus

<400> SEQUENCE: 4

Met Pro Met Asp Val Ile Leu Val Leu Trp Phe Cys Val Cys Thr Ala
 1               5                  10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
    290                 295                 300
```

-continued

```
Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
                340                 345                 350

Cys Arg Glu Cys Arg Gly Gly Val Leu Val Lys Ile Thr Glu Ala Cys
            355                 360                 365

Pro Pro Leu Asn Cys Ser Ala Lys Asp His Ile Leu Pro Glu Asn Gln
        370                 375                 380

Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
                420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Val Pro
        450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720
```

```
Gly Glu Ala Asp Cys Trp Pro Leu Ala Cys Pro Ser Leu Gly Cys Glu
            725                 730                 735
Tyr Thr Ala Met Phe Glu Gly Glu Cys Cys Pro Arg Cys Val Ser Asp
            740                 745                 750
Pro Cys Leu Ala Gly Asn Ile Ala Tyr Asp Ile Arg Lys Thr Cys Leu
            755                 760                 765
Asp Ser Phe Gly Val Ser Arg Leu Ser Gly Ala Val Trp Thr Met Ala
            770                 775                 780
Gly Ser Pro Cys Thr Thr Cys Lys Cys Lys Asn Gly Arg Val Cys Cys
785                 790                 795                 800
Ser Val Asp Leu Glu Cys Ile Glu Asn Asn
                805                 810

<210> SEQ ID NO 5
<211> LENGTH: 2433
<212> TYPE: DNA
<213> ORGANISM: Mus musculus

<400> SEQUENCE: 5
atgccgatgg atgtgatttt agttttgtgg ttctgtgtgt gcaccgccag gacagtgctg      60
ggctttggga tggaccctga ccttcagatg acatcatca ctgaacttga ccttgtgaac     120
accaccctgg gcgtcactca ggtggctgga ctacacaatg ccagtaaggc atttctgttt     180
caagatgtac agagagagat ccactcagcc cctcatgtga gtgagaagct gatccagcta     240
ttccggaata gagtgagtt accttttttg gctacagtgc agcagaagcc gtccacctca     300
ggggtgatac tgtcgatccg ggagctggaa cacagctatt tgaactggag agcagtggc     360
ccaagagaag agatacgcta tcattacatc catggcggca agcccaggac tgaggccctt     420
ccctaccgca tggccgatgg acagtggcac aaggtcgcgc tgtctgtgag cgcctctcac     480
ctcctactcc atgtcgactg caataggatt tatgagcgtg tgatagatcc tccggagacc     540
aaccttcctc caggaagcaa tctatggctt gggcaacgta atcaaaagca tggcttttc     600
aaaggaatca tccaagatgg caagatcatc ttcatgccga acggcttcat cacacagtgc     660
cccaacctaa atcgcacttg cccaacatgc agtgatttcc tgagcctggt tcaaggaata     720
atggatttgc aagagctttt ggccaagatg actgcaaaac tgaattatgc agagacgaga     780
cttggtcaac tggaaaattg ccactgtgag aagacctgcc aagtgagtgg gctgctctac     840
agggaccaag actcctgggt agatggtgac aactgcagga actgcacatg caaaagtggt     900
gctgtggagt gccgaaggat gtcctgtccc ccactcaact gttccccaga ctcacttcct     960
gtgcatattt ctggccaatg ttgtaaagtt tgcagaccaa atgtatcta tggaggaaaa    1020
gttcttgctg agggccagcg gatttaacc aagacctgcc gggaatgtcg aggtggagtc    1080
ttggtaaaaa tcacagaagc ttgcccctcct ttgaactgct cagagaagga tcatattctt    1140
ccggagaacc agtgctgcag ggtctgccga ggtcataact tctgtgcaga agcacctaag    1200
tgtggagaaa actcggaatg caaaaattgg aatacaaaag cgacttgtga gtgcaagaat    1260
ggatacatct ctgtccaggg caactctgca tactgtgaag atatcgatga gtgtgcagca    1320
aagatgcact actgtcatgc caacacggtg tgtgtcaact gccggggtt atatcgctgt    1380
gactgcatcc caggatacat ccgtgtggat gacttctctt gtacggagca tgatgattgt    1440
ggcagcggac aacacaactg tgacaaaaat gccatctgta ccaacacagt ccaggacac    1500
agctgtacct gccagccagg ctacgtggga aatggtactg tctgcaaagc attctgtgaa    1560
gagggttgca gatacggagg tacctgtgtg gcccctaaca atgtgtctg tccttctgga    1620
```

```
ttcacaggaa gccactgtga gaaagatatt gatgaatgtg cagagggatt cgttgagtgc   1680
cacaaccact cccgctgcgt taaccttcca gggtggtacc actgtgagtg cagaagcggt   1740
ttccatgacg atgggaccta ttcactgtcc ggggagtcct gcattgatat tgatgaatgt   1800
gccttaagaa ctcacacttg ttggaatgac tctgcctgca tcaacttagc aggaggattt   1860
gactgcctgt gtccctctgg gccctcctgc tctggtgact gtccccacga agggggctg    1920 aagcataatg ggcaggtgtg gattctgaga aagacaggt gttcagtctg ttcctgtaag    1980
gatgggaaga tattctgccg gcggacagct tgtgattgcc agaatccaaa tgttgacctt   2040
ttctgctgcc cagagtgtga caccagggtc actagccaat gtttagatca aagcggacag   2100
aagctctatc gaagtggaga caactggacc cacagctgcc agcagtgccg atgtctggaa   2160
ggagaggcag actgctggcc tctagcttgc cctagtttga gctgtgaata cacagccatc   2220
tttgaaggag agtgttgtcc ccgctgtgtc agtgacccct gcctggctga taatattgcc   2280
tatgacatca gaaaaacttg cctggacagc tctggtattt cgaggctgag cggcgcagtg   2340
tggacaatgg ctggatctcc ctgtacaacc tgtcaatgca agaatgggag agtctgctgc   2400
tctgtggatc tggtgtgtct tgagaataac tga                                2433

<210> SEQ ID NO 6
<211> LENGTH: 810
<212> TYPE: PRT
<213> ORGANISM: Mus musculus

<400> SEQUENCE: 6

Met Pro Met Asp Val Ile Leu Val Leu Trp Phe Cys Val Cys Thr Ala
  1               5                  10                  15

Arg Thr Val Leu Gly Phe Gly Met Asp Pro Asp Leu Gln Met Asp Ile
                 20                  25                  30

Ile Thr Glu Leu Asp Leu Val Asn Thr Thr Leu Gly Val Thr Gln Val
             35                  40                  45

Ala Gly Leu His Asn Ala Ser Lys Ala Phe Leu Phe Gln Asp Val Gln
         50                  55                  60

Arg Glu Ile His Ser Ala Pro His Val Ser Glu Lys Leu Ile Gln Leu
 65                  70                  75                  80

Phe Arg Asn Lys Ser Glu Phe Thr Phe Leu Ala Thr Val Gln Gln Lys
                 85                  90                  95

Pro Ser Thr Ser Gly Val Ile Leu Ser Ile Arg Glu Leu Glu His Ser
                100                 105                 110

Tyr Phe Glu Leu Glu Ser Ser Gly Pro Arg Glu Glu Ile Arg Tyr His
            115                 120                 125

Tyr Ile His Gly Gly Lys Pro Arg Thr Glu Ala Leu Pro Tyr Arg Met
        130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
                180                 185                 190

Arg Asn Gln Lys His Gly Phe Phe Lys Gly Ile Ile Gln Asp Gly Lys
            195                 200                 205

Ile Ile Phe Met Pro Asn Gly Phe Ile Thr Gln Cys Pro Asn Leu Asn
        210                 215                 220
```

-continued

```
Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
            245                 250                 255

Ala Glu Thr Arg Leu Gly Gln Leu Glu Asn Cys His Cys Glu Lys Thr
        260                 265                 270

Cys Gln Val Ser Gly Leu Leu Tyr Arg Asp Gln Asp Ser Trp Val Asp
    275                 280                 285

Gly Asp Asn Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
            325                 330                 335

Tyr Gly Gly Lys Val Leu Ala Glu Gly Gln Arg Ile Leu Thr Lys Thr
        340                 345                 350

Cys Arg Glu Cys Arg Gly Gly Val Leu Val Lys Ile Thr Glu Ala Cys
    355                 360                 365

Pro Pro Leu Asn Cys Ser Glu Lys Asp His Ile Leu Pro Glu Asn Gln
370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
            405                 410                 415

Glu Cys Lys Asn Gly Tyr Ile Ser Val Gln Gly Asn Ser Ala Tyr Cys
        420                 425                 430

Glu Asp Ile Asp Glu Cys Ala Ala Lys Met His Tyr Cys His Ala Asn
    435                 440                 445

Thr Val Cys Val Asn Leu Pro Gly Leu Tyr Arg Cys Asp Cys Ile Pro
450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
            485                 490                 495

Val Gln Gly His Ser Cys Thr Cys Gln Pro Gly Tyr Val Gly Asn Gly
        500                 505                 510

Thr Val Cys Lys Ala Phe Cys Glu Glu Gly Cys Arg Tyr Gly Gly Thr
    515                 520                 525

Cys Val Ala Pro Asn Lys Cys Val Cys Pro Ser Gly Phe Thr Gly Ser
530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
            565                 570                 575

Cys Arg Ser Gly Phe His Asp Asp Gly Thr Tyr Ser Leu Ser Gly Glu
        580                 585                 590

Ser Cys Ile Asp Ile Asp Glu Cys Ala Leu Arg Thr His Thr Cys Trp
    595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
```

-continued

```
                          645                 650                 655
Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810

<210> SEQ ID NO 7
<211> LENGTH: 2451
<212> TYPE: DNA
<213> ORGANISM: Homo sapiens
<220> FEATURE:
<221> NAME/KEY: CDS
<222> LOCATION: (1)...(2451)

<400> SEQUENCE: 7 atg gag tct cgg gtc tta ctg aga aca ttc tgt ttg atc ttc ggt ctc      48
Met Glu Ser Arg Val Leu Leu Arg Thr Phe Cys Leu Ile Phe Gly Leu
  1               5                  10                  15 gga gca gtt tgg ggg ctt ggt gtg gac cct tcc cta cag att gac gtc      96
Gly Ala Val Trp Gly Leu Gly Val Asp Pro Ser Leu Gln Ile Asp Val
                 20                  25                  30 tta aca gag tta gaa ctt ggg gag tcc acg acc gga gtg cgt cag gtc     144
Leu Thr Glu Leu Glu Leu Gly Glu Ser Thr Thr Gly Val Arg Gln Val
             35                  40                  45 ccg ggg ctg cat aat ggg acg aaa gcc ttt ctc ttt caa gat act ccc     192
Pro Gly Leu His Asn Gly Thr Lys Ala Phe Leu Phe Gln Asp Thr Pro
         50                  55                  60 aga agc ata aaa gca tcc act gct aca gct gaa cag ttt ttt cag aag     240
Arg Ser Ile Lys Ala Ser Thr Ala Thr Ala Glu Gln Phe Phe Gln Lys
 65                  70                  75                  80 ctg aga aat aaa cat gaa ttt act att ttg gtg acc cta aaa cag acc     288
Leu Arg Asn Lys His Glu Phe Thr Ile Leu Val Thr Leu Lys Gln Thr
                 85                  90                  95 cac tta aat tca gga gtt att ctc tca att cac cac ttg gat cac agg     336
His Leu Asn Ser Gly Val Ile Leu Ser Ile His His Leu Asp His Arg
            100                 105                 110 tac ctg gaa ctg gaa agt agt ggc cat cgg aat gaa gtc aga ctg cat     384
Tyr Leu Glu Leu Glu Ser Ser Gly His Arg Asn Glu Val Arg Leu His
        115                 120                 125 tac cgc tca ggc agt cac cgc cct cac aca gaa gtg ttt cct tac att     432
Tyr Arg Ser Gly Ser His Arg Pro His Thr Glu Val Phe Pro Tyr Ile
    130                 135                 140
```

-continued

| | |
|---|---|
| ttg gct gat gac aag tgg cac aag ctc tcc tta gcc atc agt gct tcc<br>Leu Ala Asp Asp Lys Trp His Lys Leu Ser Leu Ala Ile Ser Ala Ser<br>145                        150                        155                        160 | 480 |
| cat ttg att tta cac att gac tgc aat aaa att tat gaa agg gta gta<br>His Leu Ile Leu His Ile Asp Cys Asn Lys Ile Tyr Glu Arg Val Val<br>                        165                        170                        175 | 528 |
| gaa aag ccc tcc aca gac ttg cct cta ggc aca aca ttt tgg cta gga<br>Glu Lys Pro Ser Thr Asp Leu Pro Leu Gly Thr Thr Phe Trp Leu Gly<br>                180                        185                        190 | 576 |
| cag aga aat aat gcg cat gga tat ttt aag ggt ata atg caa gat gtc<br>Gln Arg Asn Asn Ala His Gly Tyr Phe Lys Gly Ile Met Gln Asp Val<br>195                        200                        205 | 624 |
| caa tta ctt gtc atg ccc cag gga ttt att gct cag tgc cca gat ctt<br>Gln Leu Leu Val Met Pro Gln Gly Phe Ile Ala Gln Cys Pro Asp Leu<br>    210                        215                        220 | 672 |
| aat cgc acc tgt cca act tgc aat gac ttc cat gga ctt gtg cag aaa<br>Asn Arg Thr Cys Pro Thr Cys Asn Asp Phe His Gly Leu Val Gln Lys<br>225                        230                        235                        240 | 720 |
| atc atg gag cta cag gat att tta gcc aaa aca tca gcc aag ctg tct<br>Ile Met Glu Leu Gln Asp Ile Leu Ala Lys Thr Ser Ala Lys Leu Ser<br>                        245                        250                        255 | 768 |
| cga gct gaa cag cga atg aat aga ttg gat cag tgc tat tgt gaa agg<br>Arg Ala Glu Gln Arg Met Asn Arg Leu Asp Gln Cys Tyr Cys Glu Arg<br>                260                        265                        270 | 816 |
| act tgc acc atg aag gga acc acc tac cga gaa ttt gag tcc tgg ata<br>Thr Cys Thr Met Lys Gly Thr Thr Tyr Arg Glu Phe Glu Ser Trp Ile<br>                        275                        280                        285 | 864 |
| gac ggc tgt aag aac tgc aca tgc ctg aat gga acc atc cag tgt gaa<br>Asp Gly Cys Lys Asn Cys Thr Cys Leu Asn Gly Thr Ile Gln Cys Glu<br>                290                        295                        300 | 912 |
| act cta atc tgc cca aat cct gac tgc cca ctt aag tcg gct ctt gcg<br>Thr Leu Ile Cys Pro Asn Pro Asp Cys Pro Leu Lys Ser Ala Leu Ala<br>305                        310                        315                        320 | 960 |
| tat gtg gat ggc aaa tgc tgt aag gaa tgc aaa tcg ata tgc caa ttt<br>Tyr Val Asp Gly Lys Cys Cys Lys Glu Cys Lys Ser Ile Cys Gln Phe<br>                        325                        330                        335 | 1008 |
| caa gga cga acc tac ttt gaa gga gaa aga aat aca gtc tat tcc tct<br>Gln Gly Arg Thr Tyr Phe Glu Gly Glu Arg Asn Thr Val Tyr Ser Ser<br>                340                        345                        350 | 1056 |
| tct gga gta tgt gtt ctc tat gag tgc aag gac cag acc atg aaa ctt<br>Ser Gly Val Cys Val Leu Tyr Glu Cys Lys Asp Gln Thr Met Lys Leu<br>                        355                        360                        365 | 1104 |
| gtt gag agt tca ggc tgt cca gct ttg gat tgt cca gag tct cat cag<br>Val Glu Ser Ser Gly Cys Pro Ala Leu Asp Cys Pro Glu Ser His Gln<br>    370                        375                        380 | 1152 |
| ata acc ttg tct cac agc tgt tgc aaa gtt tgt aaa ggt tat gac ttt<br>Ile Thr Leu Ser His Ser Cys Cys Lys Val Cys Lys Gly Tyr Asp Phe<br>385                        390                        395                        400 | 1200 |
| tgt tct gaa agg cat aac tgc atg gag aat tcc atc tgc aga aat ctg<br>Cys Ser Glu Arg His Asn Cys Met Glu Asn Ser Ile Cys Arg Asn Leu<br>                        405                        410                        415 | 1248 |
| aat gac agg gct gtt tgt agc tgt cga gat ggt ttt agg gct ctt cga<br>Asn Asp Arg Ala Val Cys Ser Cys Arg Asp Gly Phe Arg Ala Leu Arg<br>                420                        425                        430 | 1296 |
| gag gat aat gcc tac tgt gaa gac atc gat gag tgt gct gaa ggg cgc<br>Glu Asp Asn Ala Tyr Cys Glu Asp Ile Asp Glu Cys Ala Glu Gly Arg<br>                        435                        440                        445 | 1344 |
| cat tac tgt cgt gaa aat aca atg tgt gtc aac acc ccg ggt tct ttt<br>His Tyr Cys Arg Glu Asn Thr Met Cys Val Asn Thr Pro Gly Ser Phe<br>                450                        455                        460 | 1392 |

-continued

```
atg tgc atc tgc aaa act gga tac atc aga att gat gat tat tca tgt      1440
Met Cys Ile Cys Lys Thr Gly Tyr Ile Arg Ile Asp Asp Tyr Ser Cys
465                 470                 475                 480 aca gaa cat gat gag tgt atc aca aat cag cac aac tgt gat gaa aat      1488
Thr Glu His Asp Glu Cys Ile Thr Asn Gln His Asn Cys Asp Glu Asn
                485                 490                 495 gct tta tgc ttc aac act gtt gga gga cac aac tgt gtt tgc aag ccg      1536
Ala Leu Cys Phe Asn Thr Val Gly Gly His Asn Cys Val Cys Lys Pro
            500                 505                 510 ggc tat aca ggg aat gga acg aca tgc aaa gca ttt tgc aaa gat ggc      1584
Gly Tyr Thr Gly Asn Gly Thr Thr Cys Lys Ala Phe Cys Lys Asp Gly
        515                 520                 525 tgt agg aat gga gga gcc tgt att gcc gct aat gtg tgt gcc tgc cca      1632
Cys Arg Asn Gly Gly Ala Cys Ile Ala Ala Asn Val Cys Ala Cys Pro
530                 535                 540 caa ggc ttc act gga ccc agc tgt gaa acg gac att gat gaa tgc tct      1680
Gln Gly Phe Thr Gly Pro Ser Cys Glu Thr Asp Ile Asp Glu Cys Ser
545                 550                 555                 560 gat ggt ttt gtt caa tgt gac agt cgt gct aat tgc att aac ctg cct      1728
Asp Gly Phe Val Gln Cys Asp Ser Arg Ala Asn Cys Ile Asn Leu Pro
                565                 570                 575 gga tgg tac cac tgt gag tgc aga gat ggc tac cat gac aat ggg atg      1776
Gly Trp Tyr His Cys Glu Cys Arg Asp Gly Tyr His Asp Asn Gly Met
            580                 585                 590 ttt tca cca agt gga gaa tcg tgt gaa gat att gat gag tgt ggg acc      1824
Phe Ser Pro Ser Gly Glu Ser Cys Glu Asp Ile Asp Glu Cys Gly Thr
        595                 600                 605 ggg agg cac agc tgt gcc aat gat acc att tgc ttc aat ttg gat ggc      1872
Gly Arg His Ser Cys Ala Asn Asp Thr Ile Cys Phe Asn Leu Asp Gly
610                 615                 620 gga tat gat tgt cga tgt cct cat gga aag aat tgc aca ggg gac tgc      1920
Gly Tyr Asp Cys Arg Cys Pro His Gly Lys Asn Cys Thr Gly Asp Cys
625                 630                 635                 640 atc cat gat gga aaa gtt aag cac aat ggt cag att tgg gtg ttg gaa      1968
Ile His Asp Gly Lys Val Lys His Asn Gly Gln Ile Trp Val Leu Glu
                645                 650                 655 aat gac agg tgc tct gtg tgc tca tgt cag aat gga ttc gtt atg tgt      2016
Asn Asp Arg Cys Ser Val Cys Ser Cys Gln Asn Gly Phe Val Met Cys
            660                 665                 670 cga cgg atg gtc tgt gac tgt gag aat ccc aca gtt gat ctt ttt tgc      2064
Arg Arg Met Val Cys Asp Cys Glu Asn Pro Thr Val Asp Leu Phe Cys
        675                 680                 685 tgc cct gaa tgt gac cca agg ctt agt agt cag tgc ctc cat caa aat      2112
Cys Pro Glu Cys Asp Pro Arg Leu Ser Ser Gln Cys Leu His Gln Asn
690                 695                 700 ggg gaa act ttg tat aac agt ggt gac acc tgg gtc cag aat tgt caa      2160
Gly Glu Thr Leu Tyr Asn Ser Gly Asp Thr Trp Val Gln Asn Cys Gln
705                 710                 715                 720 cag tgc cgc tgc ttg caa ggg gaa gtt gat tgt tgg ccc ctg cct tgc      2208
Gln Cys Arg Cys Leu Gln Gly Glu Val Asp Cys Trp Pro Leu Pro Cys
                725                 730                 735 cca gat gtg gag tgt gaa ttc agc att ctc cca gag aat gag tgc tgc      2256
Pro Asp Val Glu Cys Glu Phe Ser Ile Leu Pro Glu Asn Glu Cys Cys
            740                 745                 750 ccg cgc tgt gtc aca gac cct tgc cag gct gac acc atc cgc aat gac      2304
Pro Arg Cys Val Thr Asp Pro Cys Gln Ala Asp Thr Ile Arg Asn Asp
        755                 760                 765 atc acc aag act tgc ctg gac gaa atg aat gtg gtt cgc ttc acc ggg      2352
Ile Thr Lys Thr Cys Leu Asp Glu Met Asn Val Val Arg Phe Thr Gly
```

```
                770                 775                 780
tcc tct tgg atc aaa cat ggc act gag tgt act ctc tgc cag tgc aag         2400
Ser Ser Trp Ile Lys His Gly Thr Glu Cys Thr Leu Cys Gln Cys Lys
785                 790                 795                 800 aat ggc cac atc tgt tgc tca gtg gat cca cag tgc ctt cag gaa ctg         2448
Asn Gly His Ile Cys Cys Ser Val Asp Pro Gln Cys Leu Gln Glu Leu
                805                 810                 815 tga                                                                     2451
*
```

<210> SEQ ID NO 8
<211> LENGTH: 816
<212> TYPE: PRT
<213> ORGANISM: Homo sapiens

<400> SEQUENCE: 8

```
Met Glu Ser Arg Val Leu Leu Arg Thr Phe Cys Leu Ile Phe Gly Leu
 1               5                  10                  15

Gly Ala Val Trp Gly Leu Gly Val Asp Pro Ser Leu Gln Ile Asp Val
                20                  25                  30

Leu Thr Glu Leu Glu Leu Gly Glu Ser Thr Thr Gly Val Arg Gln Val
            35                  40                  45

Pro Gly Leu His Asn Gly Thr Lys Ala Phe Leu Phe Gln Asp Thr Pro
        50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
               100                 105                 110

Tyr Leu Glu Leu Glu Ser Ser Gly His Arg Asn Glu Val Arg Leu His
           115                 120                 125

Tyr Arg Ser Gly Ser His Arg Pro His Thr Glu Val Phe Pro Tyr Ile
       130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
               165                 170                 175

Glu Lys Pro Ser Thr Asp Leu Pro Leu Gly Thr Thr Phe Trp Leu Gly
           180                 185                 190

Gln Arg Asn Asn Ala His Gly Tyr Phe Lys Gly Ile Met Gln Asp Val
       195                 200                 205

Gln Leu Leu Val Met Pro Gln Gly Phe Ile Ala Gln Cys Pro Asp Leu
   210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
               245                 250                 255

Arg Ala Glu Gln Arg Met Asn Arg Leu Asp Gln Cys Tyr Cys Glu Arg
           260                 265                 270

Thr Cys Thr Met Lys Gly Thr Thr Tyr Arg Glu Phe Glu Ser Trp Ile
       275                 280                 285

Asp Gly Cys Lys Asn Cys Thr Cys Leu Asn Gly Thr Ile Gln Cys Glu
   290                 295                 300

Thr Leu Ile Cys Pro Asn Pro Asp Cys Pro Leu Lys Ser Ala Leu Ala
```

-continued

```
            305                 310                 315                 320
        Tyr Val Asp Gly Lys Cys Cys Lys Glu Cys Lys Ser Ile Cys Gln Phe
                        325                 330                 335
        Gln Gly Arg Thr Tyr Phe Glu Gly Glu Arg Asn Thr Val Tyr Ser Ser
                        340                 345                 350
        Ser Gly Val Cys Val Leu Tyr Glu Cys Lys Asp Gln Thr Met Lys Leu
                        355                 360                 365
        Val Glu Ser Ser Gly Cys Pro Ala Leu Asp Cys Pro Glu Ser His Gln
                370                 375                 380
        Ile Thr Leu Ser His Ser Cys Cys Lys Val Cys Lys Gly Tyr Asp Phe
        385                 390                 395                 400
        Cys Ser Glu Arg His Asn Cys Met Glu Asn Ser Ile Cys Arg Asn Leu
                        405                 410                 415
        Asn Asp Arg Ala Val Cys Ser Cys Arg Asp Gly Phe Arg Ala Leu Arg
                        420                 425                 430
        Glu Asp Asn Ala Tyr Cys Glu Asp Ile Asp Glu Cys Ala Glu Gly Arg
                        435                 440                 445
        His Tyr Cys Arg Glu Asn Thr Met Cys Val Asn Thr Pro Gly Ser Phe
                450                 455                 460
        Met Cys Ile Cys Lys Thr Gly Tyr Ile Arg Ile Asp Asp Tyr Ser Cys
        465                 470                 475                 480
        Thr Glu His Asp Glu Cys Ile Thr Asn Gln His Asn Cys Asp Glu Asn
                        485                 490                 495
        Ala Leu Cys Phe Asn Thr Val Gly Gly His Asn Cys Val Cys Lys Pro
                        500                 505                 510
        Gly Tyr Thr Gly Asn Gly Thr Thr Cys Lys Ala Phe Cys Lys Asp Gly
                        515                 520                 525
        Cys Arg Asn Gly Gly Ala Cys Ile Ala Ala Asn Val Cys Ala Cys Pro
                        530                 535                 540
        Gln Gly Phe Thr Gly Pro Ser Cys Glu Thr Asp Ile Asp Glu Cys Ser
        545                 550                 555                 560
        Asp Gly Phe Val Gln Cys Asp Ser Arg Ala Asn Cys Ile Asn Leu Pro
                        565                 570                 575
        Gly Trp Tyr His Cys Glu Cys Arg Asp Gly Tyr His Asp Asn Gly Met
                        580                 585                 590
        Phe Ser Pro Ser Gly Glu Ser Cys Glu Asp Ile Asp Glu Cys Gly Thr
                        595                 600                 605
        Gly Arg His Ser Cys Ala Asn Asp Thr Ile Cys Phe Asn Leu Asp Gly
                610                 615                 620
        Gly Tyr Asp Cys Arg Cys Pro His Gly Lys Asn Cys Thr Gly Asp Cys
        625                 630                 635                 640
        Ile His Asp Gly Lys Val Lys His Asn Gly Gln Ile Trp Val Leu Glu
                        645                 650                 655
        Asn Asp Arg Cys Ser Val Cys Ser Cys Gln Asn Gly Phe Val Met Cys
                        660                 665                 670
        Arg Arg Met Val Cys Asp Cys Glu Asn Pro Thr Val Asp Leu Phe Cys
                        675                 680                 685
        Cys Pro Glu Cys Asp Pro Arg Leu Ser Ser Gln Cys Leu His Gln Asn
                690                 695                 700
        Gly Glu Thr Leu Tyr Asn Ser Gly Asp Thr Trp Val Gln Asn Cys Gln
        705                 710                 715                 720
        Gln Cys Arg Cys Leu Gln Gly Glu Val Asp Cys Trp Pro Leu Pro Cys
                        725                 730                 735
```

```
Pro Asp Val Glu Cys Glu Phe Ser Ile Leu Pro Glu Asn Glu Cys Cys
            740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Met Asn Val Val Arg Phe Thr Gly
            770                 775                 780

Ser Ser Trp Ile Lys His Gly Thr Glu Cys Thr Leu Cys Gln Cys Lys
785                 790                 795                 800

Asn Gly His Ile Cys Cys Ser Val Asp Pro Gln Cys Leu Gln Glu Leu
                805                 810                 815

<210> SEQ ID NO 9
<211> LENGTH: 2451
<212> TYPE: DNA
<213> ORGANISM: Rattus norvegicus
<220> FEATURE:
<221> NAME/KEY: CDS
<222> LOCATION: (1)...(2451)

<400> SEQUENCE: 9 atg gaa tcc cgg gta tta ctg aga acg ttc tgc gtg atc ctc ggg ctc       48
Met Glu Ser Arg Val Leu Leu Arg Thr Phe Cys Val Ile Leu Gly Leu
 1               5                  10                  15 gaa gcg gtt tgg gga ctt ggt gtg gac ccc tcc cta cag att gac gtc       96
Glu Ala Val Trp Gly Leu Gly Val Asp Pro Ser Leu Gln Ile Asp Val
            20                  25                  30 tta tca gag tta gaa ctt ggg gag tcc aca gct gga gtg cgc caa gtc      144
Leu Ser Glu Leu Glu Leu Gly Glu Ser Thr Ala Gly Val Arg Gln Val
        35                  40                  45 cca gga ctg cat aat ggg acg aaa gcc ttc ctc ttc caa gat tcc ccc      192
Pro Gly Leu His Asn Gly Thr Lys Ala Phe Leu Phe Gln Asp Ser Pro
    50                  55                  60 aga agc ata aaa gca ccc att gct aca gct gag cgg ttt ttc cag aag      240
Arg Ser Ile Lys Ala Pro Ile Ala Thr Ala Glu Arg Phe Phe Gln Lys
65                  70                  75                  80 ctg agg aat aaa cac gag ttc aca att ctg gtg acc ctg aaa cag atc      288
Leu Arg Asn Lys His Glu Phe Thr Ile Leu Val Thr Leu Lys Gln Ile
                85                  90                  95 cac tta aat tcg gga gtc att ctc tcc atc cac cac ttg gat cac agg      336
His Leu Asn Ser Gly Val Ile Leu Ser Ile His His Leu Asp His Arg
            100                 105                 110 tac ctg gaa ctg gaa agc agc ggc cac cgg aat gag atc aga ctg cat      384
Tyr Leu Glu Leu Glu Ser Ser Gly His Arg Asn Glu Ile Arg Leu His
        115                 120                 125 tac cgc tct gga act cac cgc ccg cac acg gaa gtg ttt cct tat att      432
Tyr Arg Ser Gly Thr His Arg Pro His Thr Glu Val Phe Pro Tyr Ile
    130                 135                 140 ttg gct gat gcc aag tgg cac aag ctc tcc tta gcc ttc agt gcc tcc      480
Leu Ala Asp Ala Lys Trp His Lys Leu Ser Leu Ala Phe Ser Ala Ser
145                 150                 155                 160 cac tta att tta cac atc gac tgc aac aag atc tat gaa cga gtg gtg      528
His Leu Ile Leu His Ile Asp Cys Asn Lys Ile Tyr Glu Arg Val Val
                165                 170                 175 gaa atg cct tct aca gac ttg cct ctg ggc acc aca ttt tgg ttg gga      576
Glu Met Pro Ser Thr Asp Leu Pro Leu Gly Thr Thr Phe Trp Leu Gly
            180                 185                 190 cag aga aat aac gca cac ggg tat ttt aag gga ata atg caa gat gtg      624
Gln Arg Asn Asn Ala His Gly Tyr Phe Lys Gly Ile Met Gln Asp Val
        195                 200                 205
```

```
caa tta ctt gtc atg ccc cag ggg ttc atc gct cag tgc ccg gat ctt      672
Gln Leu Leu Val Met Pro Gln Gly Phe Ile Ala Gln Cys Pro Asp Leu
    210                 215                 220 aat cga acc tgt cca aca tgc aac gac ttc cat ggg ctt gtg cag aaa      720
Asn Arg Thr Cys Pro Thr Cys Asn Asp Phe His Gly Leu Val Gln Lys
225                 230                 235                 240 atc atg gag ctg cag gac att tta tcg aag acg tca gcc aag ttg tct      768
Ile Met Glu Leu Gln Asp Ile Leu Ser Lys Thr Ser Ala Lys Leu Ser
                245                 250                 255 aga gct gaa caa cga atg aac agg ctg gat cag tgc tac tgt gag cgg      816
Arg Ala Glu Gln Arg Met Asn Arg Leu Asp Gln Cys Tyr Cys Glu Arg
            260                 265                 270 acg tgc acc atg aag gga gcc acc tac cgg gag ttc gag tcc tgg aca      864
Thr Cys Thr Met Lys Gly Ala Thr Tyr Arg Glu Phe Glu Ser Trp Thr
        275                 280                 285 gac ggc tgc aag aac tgc aca tgc ttg aat ggg acc atc cag tgc gag      912
Asp Gly Cys Lys Asn Cys Thr Cys Leu Asn Gly Thr Ile Gln Cys Glu
    290                 295                 300 act ctg gtc tgc cct gct ccc gac tgc ccg gct aaa tcg gct cca gcg      960
Thr Leu Val Cys Pro Ala Pro Asp Cys Pro Ala Lys Ser Ala Pro Ala
305                 310                 315                 320 tac gtg gat ggc aag tgc tgt aag gag tgc aag tcc acc tgc cag ttc     1008
Tyr Val Asp Gly Lys Cys Cys Lys Glu Cys Lys Ser Thr Cys Gln Phe
                325                 330                 335 cag ggg cgg agc tac ttt gag gga gaa agg agc aca gtc ttc tca gct     1056
Gln Gly Arg Ser Tyr Phe Glu Gly Glu Arg Ser Thr Val Phe Ser Ala
            340                 345                 350 tcc gga atg tgc gtc ttg tat gaa tgc aag gat cag acc atg aag ctt     1104
Ser Gly Met Cys Val Leu Tyr Glu Cys Lys Asp Gln Thr Met Lys Leu
        355                 360                 365 gtt gag aac gcc ggc tgc ccg gct tta gat tgc ccc gag tct cat cag     1152
Val Glu Asn Ala Gly Cys Pro Ala Leu Asp Cys Pro Glu Ser His Gln
    370                 375                 380 atc gcc ttg tct cac agc tgc tgc aag gtt tgc aaa ggt tat gac ttc     1200
Ile Ala Leu Ser His Ser Cys Cys Lys Val Cys Lys Gly Tyr Asp Phe
385                 390                 395                 400 tgt tct gag aag cat aca tgc atg gag aac tca gtc tgc agg aac ctg     1248
Cys Ser Glu Lys His Thr Cys Met Glu Asn Ser Val Cys Arg Asn Leu
                405                 410                 415 aac gac agg gca gtg tgc agc tgc cgg gat ggt ttc cgg gcc ctc cgg     1296
Asn Asp Arg Ala Val Cys Ser Cys Arg Asp Gly Phe Arg Ala Leu Arg
            420                 425                 430 gag gac aat gcc tac tgt gaa gac att gac gag tgt gca gag ggg cgc     1344
Glu Asp Asn Ala Tyr Cys Glu Asp Ile Asp Glu Cys Ala Glu Gly Arg
        435                 440                 445 cat tac tgc cgt gag aac acc atg tgt gtg aac aca ccg ggc tct ttc     1392
His Tyr Cys Arg Glu Asn Thr Met Cys Val Asn Thr Pro Gly Ser Phe
    450                 455                 460 ctg tgt atc tgc caa aca ggg tac atc aga atc gac gat tac tcg tgt     1440
Leu Cys Ile Cys Gln Thr Gly Tyr Ile Arg Ile Asp Asp Tyr Ser Cys
465                 470                 475                 480 acg gaa cat gac gag tgc ctc aca aac cag cac aac tgt gac gag aac     1488
Thr Glu His Asp Glu Cys Leu Thr Asn Gln His Asn Cys Asp Glu Asn
                485                 490                 495 gct ttg tgc ttt aac acc gtt gga ggt cac aac tgc gtc tgc aag cct     1536
Ala Leu Cys Phe Asn Thr Val Gly Gly His Asn Cys Val Cys Lys Pro
            500                 505                 510 ggg tac act ggg aat gga acc acg tgc aaa gct ttc tgc aaa gac ggc     1584
Gly Tyr Thr Gly Asn Gly Thr Thr Cys Lys Ala Phe Cys Lys Asp Gly
        515                 520                 525
```

```
tgc aaa aac gga ggt gcc tgc att gct gcc aat gtc tgt gct tgc cca    1632
Cys Lys Asn Gly Gly Ala Cys Ile Ala Ala Asn Val Cys Ala Cys Pro
    530                 535                 540 caa ggc ttc acc gga ccc agc tgt gag aca gac att gat gag tgc tct    1680
Gln Gly Phe Thr Gly Pro Ser Cys Glu Thr Asp Ile Asp Glu Cys Ser
545                 550                 555                 560 gag ggc ttt gtt cag tgt gac agc cgt gcc aac tgc att aac ctg cct    1728
Glu Gly Phe Val Gln Cys Asp Ser Arg Ala Asn Cys Ile Asn Leu Pro
                565                 570                 575 ggg tgg tac cac tgt gag tgc aga gat ggc tac cat gac aat ggg atg    1776
Gly Trp Tyr His Cys Glu Cys Arg Asp Gly Tyr His Asp Asn Gly Met
            580                 585                 590 ttt gcg cca ggt gga gaa tcc tgt gaa gat att gat gaa tgt ggg act    1824
Phe Ala Pro Gly Gly Glu Ser Cys Glu Asp Ile Asp Glu Cys Gly Thr
        595                 600                 605 ggg agg cac agc tgt gcc aat gac acc att tgc ttc aac ttg gac ggt    1872
Gly Arg His Ser Cys Ala Asn Asp Thr Ile Cys Phe Asn Leu Asp Gly
    610                 615                 620 ggc tac gat tgc cgg tgt ccc cat gga aag aac tgc aca ggg gac tgc    1920
Gly Tyr Asp Cys Arg Cys Pro His Gly Lys Asn Cys Thr Gly Asp Cys
625                 630                 635                 640 gtg cac gac ggg aaa gtc aaa cac aac ggc cag atc tgg gtg ctg gag    1968
Val His Asp Gly Lys Val Lys His Asn Gly Gln Ile Trp Val Leu Glu
                645                 650                 655 aac gac agg tgc tct gtg tgt tcc tgc cag act gga ttt gtt atg tgc    2016
Asn Asp Arg Cys Ser Val Cys Ser Cys Gln Thr Gly Phe Val Met Cys
            660                 665                 670 caa cgg atg gtc tgt gac tgc gaa aac ccc aca gtt gac ctc tcc tgc    2064
Gln Arg Met Val Cys Asp Cys Glu Asn Pro Thr Val Asp Leu Ser Cys
        675                 680                 685 tgc cct gag tgc gac cca agg ctg agc agc cag tgc ctg cat caa aac    2112
Cys Pro Glu Cys Asp Pro Arg Leu Ser Ser Gln Cys Leu His Gln Asn
    690                 695                 700 ggg gaa acc gtg tac aac agc ggt gac acc tgg gcc cag gat tgc cgt    2160
Gly Glu Thr Val Tyr Asn Ser Gly Asp Thr Trp Ala Gln Asp Cys Arg
705                 710                 715                 720 cag tgc cgc tgc ttg caa gaa gaa gtt gac tgc tgg ccc ctg gct tgc    2208
Gln Cys Arg Cys Leu Gln Glu Glu Val Asp Cys Trp Pro Leu Ala Cys
                725                 730                 735 cca gag gta gag tgt gaa ttt agt gtc ctt cct gag aac gag tgc tgc    2256
Pro Glu Val Glu Cys Glu Phe Ser Val Leu Pro Glu Asn Glu Cys Cys
            740                 745                 750 cca cgc tgt gtc acc gat cct tgt cag gct gac acc atc cgc aat gac    2304
Pro Arg Cys Val Thr Asp Pro Cys Gln Ala Asp Thr Ile Arg Asn Asp
        755                 760                 765 atc acc aaa acc tgc ctg gac gag atg aac gtg gtt cgc ttc act ggg    2352
Ile Thr Lys Thr Cys Leu Asp Glu Met Asn Val Val Arg Phe Thr Gly
    770                 775                 780 tct tcc tgg atc aag cac ggc acg gag tgc acc ctc tgc cag tgc aag    2400
Ser Ser Trp Ile Lys His Gly Thr Glu Cys Thr Leu Cys Gln Cys Lys
785                 790                 795                 800 aac ggc cac gtg tgc tgc tca gtg gac cca cag tgc ctc cag gag ctg    2448
Asn Gly His Val Cys Cys Ser Val Asp Pro Gln Cys Leu Gln Glu Leu
                805                 810                 815 tga                                                                2451
*

<210> SEQ ID NO 10
<211> LENGTH: 816
```

<212> TYPE: PRT
<213> ORGANISM: Rattus norvegicus

<400> SEQUENCE: 10

```
Met Glu Ser Arg Val Leu Leu Arg Thr Phe Cys Val Ile Leu Gly Leu
1               5                   10                  15

Glu Ala Val Trp Gly Leu Gly Val Asp Pro Ser Leu Gln Ile Asp Val
            20                  25                  30

Leu Ser Glu Leu Glu Leu Gly Glu Ser Thr Ala Gly Val Arg Gln Val
        35                  40                  45

Pro Gly Leu His Asn Gly Thr Lys Ala Phe Leu Phe Gln Asp Ser Pro
    50                  55                  60

Arg Ser Ile Lys Ala Pro Ile Ala Thr Ala Glu Arg Phe Phe Gln Lys
65                  70                  75                  80

Leu Arg Asn Lys His Glu Phe Thr Ile Leu Val Thr Leu Lys Gln Ile
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Ile Arg Leu His
        115                 120                 125

Tyr Arg Ser Gly Thr His Arg Pro His Thr Glu Val Phe Pro Tyr Ile
    130                 135                 140

Leu Ala Asp Ala Lys Trp His Lys Leu Ser Leu Ala Phe Ser Ala Ser
145                 150                 155                 160

His Leu Ile Leu His Ile Asp Cys Asn Lys Ile Tyr Glu Arg Val Val
                165                 170                 175

Glu Met Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ser Lys Thr Ser Ala Lys Leu Ser
                245                 250                 255

Arg Ala Glu Gln Arg Met Asn Arg Leu Asp Gln Cys Tyr Cys Glu Arg
            260                 265                 270

Thr Cys Thr Met Lys Gly Ala Thr Tyr Arg Glu Phe Glu Ser Trp Thr
        275                 280                 285

Asp Gly Cys Lys Asn Cys Thr Cys Leu Asn Gly Thr Ile Gln Cys Glu
    290                 295                 300

Thr Leu Val Cys Pro Ala Pro Asp Cys Pro Ala Lys Ser Ala Pro Ala
305                 310                 315                 320

Tyr Val Asp Gly Lys Cys Cys Lys Glu Cys Lys Ser Thr Cys Gln Phe
                325                 330                 335

Gln Gly Arg Ser Tyr Phe Glu Gly Glu Arg Ser Thr Val Phe Ser Ala
            340                 345                 350

Ser Gly Met Cys Val Leu Tyr Glu Cys Lys Asp Gln Thr Met Lys Leu
        355                 360                 365

Val Glu Asn Ala Gly Cys Pro Ala Leu Asp Cys Pro Glu Ser His Gln
    370                 375                 380

Ile Ala Leu Ser His Ser Cys Cys Lys Val Cys Lys Gly Tyr Asp Phe
385                 390                 395                 400
```

-continued

```
Cys Ser Glu Lys His Thr Cys Met Glu Asn Ser Val Cys Arg Asn Leu
                405                 410                 415

Asn Asp Arg Ala Val Cys Ser Cys Arg Asp Gly Phe Arg Ala Leu Arg
            420                 425                 430

Glu Asp Asn Ala Tyr Cys Glu Asp Ile Asp Glu Cys Ala Glu Gly Arg
        435                 440                 445

His Tyr Cys Arg Glu Asn Thr Met Cys Val Asn Thr Pro Gly Ser Phe
    450                 455                 460

Leu Cys Ile Cys Gln Thr Gly Tyr Ile Arg Ile Asp Asp Tyr Ser Cys
465                 470                 475                 480

Thr Glu His Asp Glu Cys Leu Thr Asn Gln His Asn Cys Asp Glu Asn
                485                 490                 495

Ala Leu Cys Phe Asn Thr Val Gly Gly His Asn Cys Val Cys Lys Pro
            500                 505                 510

Gly Tyr Thr Gly Asn Gly Thr Thr Cys Lys Ala Phe Cys Lys Asp Gly
        515                 520                 525

Cys Lys Asn Gly Gly Ala Cys Ile Ala Ala Asn Val Cys Ala Cys Pro
    530                 535                 540

Gln Gly Phe Thr Gly Pro Ser Cys Glu Thr Asp Ile Asp Glu Cys Ser
545                 550                 555                 560

Glu Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ala Pro Gly Gly Glu Ser Cys Glu Asp Ile Asp Glu Cys Gly Thr
        595                 600                 605

Gly Arg His Ser Cys Ala Asn Asp Thr Ile Cys Phe Asn Leu Asp Gly
    610                 615                 620

Gly Tyr Asp Cys Arg Cys Pro His Gly Lys Asn Cys Thr Gly Asp Cys
625                 630                 635                 640

Val His Asp Gly Lys Val Lys His Asn Gly Gln Ile Trp Val Leu Glu
                645                 650                 655

Asn Asp Arg Cys Ser Val Cys Ser Cys Gln Thr Gly Phe Val Met Cys
            660                 665                 670

Gln Arg Met Val Cys Asp Cys Glu Asn Pro Thr Val Asp Leu Ser Cys
        675                 680                 685

Cys Pro Glu Cys Asp Pro Arg Leu Ser Ser Gln Cys Leu His Gln Asn
    690                 695                 700

Gly Glu Thr Val Tyr Asn Ser Gly Asp Thr Trp Ala Gln Asp Cys Arg
705                 710                 715                 720

Gln Cys Arg Cys Leu Gln Glu Val Asp Cys Trp Pro Leu Ala Cys
                725                 730                 735

Pro Glu Val Glu Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
        755                 760                 765

Ile Thr Lys Thr Cys Leu Asp Glu Met Asn Val Val Arg Phe Thr Gly
    770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815
```

-continued

```
<210> SEQ ID NO 11
<211> LENGTH: 2460
<212> TYPE: DNA
<213> ORGANISM: Mus musculus
<220> FEATURE:
<221> NAME/KEY: CDS
<222> LOCATION: (1)...(2460)
<221> NAME/KEY: misc_feature
<222> LOCATION: (1)...(2460)
<223> OTHER INFORMATION: n = A,T,C or G

<400> SEQUENCE: 11 atg cac gcc atg gaa tcc cgg gtg tta ctg aga acg ttc tgc gtg atc      48
Met His Ala Met Glu Ser Arg Val Leu Leu Arg Thr Phe Cys Val Ile
 1               5                  10                  15 ctc ggc ctt gga gcg gtt tgg ggg ctt ggt gtg gac ccc tcc cta cag      96
Leu Gly Leu Gly Ala Val Trp Gly Leu Gly Val Asp Pro Ser Leu Gln
             20                  25                  30 att gac gtc tta aca gag tta gaa ctt ggg gag tct aca gat gga gtg     144
Ile Asp Val Leu Thr Glu Leu Glu Leu Gly Glu Ser Thr Asp Gly Val
         35                  40                  45 cgc caa gtc ccg gga ctg cat aat ggg acg aaa gcc ttc ctc ttc caa     192
Arg Gln Val Pro Gly Leu His Asn Gly Thr Lys Ala Phe Leu Phe Gln
     50                  55                  60 gag tcc ccc aga agc ata aag gca tcc act gct aca gct gag cgg ttt     240
Glu Ser Pro Arg Ser Ile Lys Ala Ser Thr Ala Thr Ala Glu Arg Phe
 65                  70                  75                  80 ctc cag aag ctg aga aat aaa cac gag ttc aca atc ttg gtg acc tta     288
Leu Gln Lys Leu Arg Asn Lys His Glu Phe Thr Ile Leu Val Thr Leu
                 85                  90                  95 aaa cag atc cac tta aat tcg gga gtt atc ctc tcc atc cac cac ttg     336
Lys Gln Ile His Leu Asn Ser Gly Val Ile Leu Ser Ile His His Leu
            100                 105                 110 gat cac agg tac ctg gaa ctg gaa agc agt ggc cat cgg aat gag atc     384
Asp His Arg Tyr Leu Glu Leu Glu Ser Ser Gly His Arg Asn Glu Ile
        115                 120                 125 aga ctc cac tac cgc tct ggc act cac cgc ccc cac acg gaa gtg ttt     432
Arg Leu His Tyr Arg Ser Gly Thr His Arg Pro His Thr Glu Val Phe
    130                 135                 140 cct tat att ttg gct gat gcc aag tgg cac aag ctc tcc tta gcc ttc     480
Pro Tyr Ile Leu Ala Asp Ala Lys Trp His Lys Leu Ser Leu Ala Phe
145                 150                 155                 160 agt gcc tct cac tta att tta cac atc gac tgc aat aag atc tat gaa     528
Ser Ala Ser His Leu Ile Leu His Ile Asp Cys Asn Lys Ile Tyr Glu
                165                 170                 175 cga gtg gtg gaa atg ccc ttc aca gac ttg gct ctg ggc aca aca ttt     576
Arg Val Val Glu Met Pro Phe Thr Asp Leu Ala Leu Gly Thr Thr Phe
            180                 185                 190 tgg ttg gga cag aga aat aat gca cat ggc tat ttt aag gga ata atg     624
Trp Leu Gly Gln Arg Asn Asn Ala His Gly Tyr Phe Lys Gly Ile Met
        195                 200                 205 cag gat gtg cac gtc ctt gtc atg cct cag ggc ttc att gct cag tgc     672
Gln Asp Val His Val Leu Val Met Pro Gln Gly Phe Ile Ala Gln Cys
    210                 215                 220 ccg gac ctt aat cga acc tgt cca aca tgc aac gac ttc cat ggg ctt     720
Pro Asp Leu Asn Arg Thr Cys Pro Thr Cys Asn Asp Phe His Gly Leu
225                 230                 235                 240 gtg cag aaa atc atg gag ctg cag gac att tta tca aag acg tca gcc     768
Val Gln Lys Ile Met Glu Leu Gln Asp Ile Leu Ser Lys Thr Ser Ala
                245                 250                 255 aag ctg tcc cga gct gaa caa aga atg aac agg ctg gat cag tgc tac     816
```

```
Lys Leu Ser Arg Ala Glu Gln Arg Met Asn Arg Leu Asp Gln Cys Tyr
            260                 265                 270 tgt gag cgg aca tgc act gtg aag gga acc acc tac cga gag tct gag      864
Cys Glu Arg Thr Cys Thr Val Lys Gly Thr Thr Tyr Arg Glu Ser Glu
        275                 280                 285 tcc tgg aca gac ggc tgt aag aac tgc aca tgc ttg aac ggg acc atc      912
Ser Trp Thr Asp Gly Cys Lys Asn Cys Thr Cys Leu Asn Gly Thr Ile
    290                 295                 300 cag tgc gag act ctg gtc tgc cct gct cct gac tgc cct cct aaa tcg      960
Gln Cys Glu Thr Leu Val Cys Pro Ala Pro Asp Cys Pro Pro Lys Ser
305                 310                 315                 320 gcc cct gcg tat gtg gat ggc aag tgc tgt aag gag tgc aaa tca acc     1008
Ala Pro Ala Tyr Val Asp Gly Lys Cys Cys Lys Glu Cys Lys Ser Thr
                325                 330                 335 tgc cag ttc cag gga cgg agc tac ttt gag gga gaa agg aac acg gca     1056
Cys Gln Phe Gln Gly Arg Ser Tyr Phe Glu Gly Glu Arg Asn Thr Ala
        340                 345                 350 tac tca tct tct gga atg tgt gtc tta tat gaa tgc aag gat cag acc     1104
Tyr Ser Ser Ser Gly Met Cys Val Leu Tyr Glu Cys Lys Asp Gln Thr
    355                 360                 365 atg aag ctt gtt gag aac att ggc tgc cca ccc tta gat tgt ccc gag     1152
Met Lys Leu Val Glu Asn Ile Gly Cys Pro Pro Leu Asp Cys Pro Glu
370                 375                 380 tct cat cag att gcc ttg tct cac agc tgc tgc aag gtt tgt aaa ggt     1200
Ser His Gln Ile Ala Leu Ser His Ser Cys Cys Lys Val Cys Lys Gly
385                 390                 395                 400 tat gac ttc tgt tct gag aag cat acc tgc atg gag aac tcg gtc tgc     1248
Tyr Asp Phe Cys Ser Glu Lys His Thr Cys Met Glu Asn Ser Val Cys
                405                 410                 415 agg aac ctg aac gac agg gtt gtg tgc agc tgc agg gat ggt ttt cgg     1296
Arg Asn Leu Asn Asp Arg Val Val Cys Ser Cys Arg Asp Gly Phe Arg
        420                 425                 430 gct ctc cga gag gac aac gcc tac tgt gaa gac att gac gag tgt gca     1344
Ala Leu Arg Glu Asp Asn Ala Tyr Cys Glu Asp Ile Asp Glu Cys Ala
    435                 440                 445 gaa ggg cgc cat tac tgc cgt gag aac acc atg tgt gtg aat aca cct     1392
Glu Gly Arg His Tyr Cys Arg Glu Asn Thr Met Cys Val Asn Thr Pro
450                 455                 460 ggt tct ttc atg tgt gtc tgc aaa act ggg tac atc agg atc gac gat     1440
Gly Ser Phe Met Cys Val Cys Lys Thr Gly Tyr Ile Arg Ile Asp Asp
465                 470                 475                 480 tac tca tgt aca gaa cat gat gag tgt ctc aca acc cag cac aat tgt     1488
Tyr Ser Cys Thr Glu His Asp Glu Cys Leu Thr Thr Gln His Asn Cys
                485                 490                 495 gat gaa aac gct ttg tgc ttt aac act gtt gga gga cac aac tgt gtc     1536
Asp Glu Asn Ala Leu Cys Phe Asn Thr Val Gly Gly His Asn Cys Val
        500                 505                 510 tgc aag cct ggc tac acc ggg aat gga acc acg tgc aaa gct ttc tgc     1584
Cys Lys Pro Gly Tyr Thr Gly Asn Gly Thr Thr Cys Lys Ala Phe Cys
    515                 520                 525 aaa gat ggc tgt aga aac gga gga gcg tgc att gct gcc aat gtg tgt     1632
Lys Asp Gly Cys Arg Asn Gly Gly Ala Cys Ile Ala Ala Asn Val Cys
530                 535                 540 gcc tgc cca caa ggc ttc acg gga ccc agc tgt gag aca gac att gac     1680
Ala Cys Pro Gln Gly Phe Thr Gly Pro Ser Cys Glu Thr Asp Ile Asp
545                 550                 555                 560 gag tgc tct gag ggc ttt gtt cag tgt gac agc cgt gcc aac tgc atc     1728
Glu Cys Ser Glu Gly Phe Val Gln Cys Asp Ser Arg Ala Asn Cys Ile
                565                 570                 575
```

```
aac ctg cct ggg tgg tat cac tgt gag tgc aga gac ggc tac cat gac    1776
Asn Leu Pro Gly Trp Tyr His Cys Glu Cys Arg Asp Gly Tyr His Asp
            580                 585                 590 aat ggg atg ttt gcg cca ggc gga gaa tcc tgt gaa gat att gac gaa    1824
Asn Gly Met Phe Ala Pro Gly Gly Glu Ser Cys Glu Asp Ile Asp Glu
        595                 600                 605 tgc ggg act ggg agg cac agc tgc acc aac gac acc att tgc ttc aac    1872
Cys Gly Thr Gly Arg His Ser Cys Thr Asn Asp Thr Ile Cys Phe Asn
    610                 615                 620 ttg gac ggg gga tac gat tgc cgg tgt ccc cat ggg aag aac tgc act    1920
Leu Asp Gly Gly Tyr Asp Cys Arg Cys Pro His Gly Lys Asn Cys Thr
625                 630                 635                 640 ggg gac tgc gtg cac gag ggg aaa gtg aag cac acc ggc cag atc tgg    1968
Gly Asp Cys Val His Glu Gly Lys Val Lys His Thr Gly Gln Ile Trp
                645                 650                 655 gtg ctg gaa aac gac agg tgc tcc gtg tgt tcc tgg cag act ggg ttt    2016
Val Leu Glu Asn Asp Arg Cys Ser Val Cys Ser Trp Gln Thr Gly Phe
            660                 665                 670 gtc atg tgt cga cgg atg gtc tgc gac tgc gaa aac ccc aca gat gac    2064
Val Met Cys Arg Arg Met Val Cys Asp Cys Glu Asn Pro Thr Asp Asp
        675                 680                 685 ctt tcc tgc tgc cct gag tgt gac cca agg ctg agc agt cag tgc ctg    2112
Leu Ser Cys Cys Pro Glu Cys Asp Pro Arg Leu Ser Ser Gln Cys Leu
    690                 695                 700 cat caa aac ggg gaa acc gtg tac aac agc ggc gac acc tgg gtc cag    2160
His Gln Asn Gly Glu Thr Val Tyr Asn Ser Gly Asp Thr Trp Val Gln
705                 710                 715                 720 gat tgc cgt cag tgc cgc tgc ttg caa gga gaa gtt gac tgt tgg ccc    2208
Asp Cys Arg Gln Cys Arg Cys Leu Gln Gly Glu Val Asp Cys Trp Pro
                725                 730                 735 ctg gct tgc cca gag gta gaa tgt gaa ttt agc gtc ctt cct gag aac    2256
Leu Ala Cys Pro Glu Val Glu Cys Glu Phe Ser Val Leu Pro Glu Asn
            740                 745                 750 gag tgc tgc cca cgc tgt gtc acc gat cct tgt cag gcc gac acc atc    2304
Glu Cys Cys Pro Arg Cys Val Thr Asp Pro Cys Gln Ala Asp Thr Ile
        755                 760                 765 cgc aat gac atc acc aaa acc tgc ctg gac gag atg aac gtg gtt cgc    2352
Arg Asn Asp Ile Thr Lys Thr Cys Leu Asp Glu Met Asn Val Val Arg
    770                 775                 780 ttc acc ggg tct tcc tgg atc aag cac ggc acg gag tgt acc ctc tgc    2400
Phe Thr Gly Ser Ser Trp Ile Lys His Gly Thr Glu Cys Thr Leu Cys
785                 790                 795                 800 cag tgc aag aat ggc cat ttg tgc tgc tca gtg gat cca cag tgc ctt    2448
Gln Cys Lys Asn Gly His Leu Cys Cys Ser Val Asp Pro Gln Cys Leu
                805                 810                 815 cag gag ctg tga                                                    2460
Gln Glu Leu  *

<210> SEQ ID NO 12
<211> LENGTH: 819
<212> TYPE: PRT
<213> ORGANISM: Mus musculus

<400> SEQUENCE: 12

Met His Ala Met Glu Ser Arg Val Leu Leu Arg Thr Phe Cys Val Ile
1               5                   10                  15

Leu Gly Leu Gly Ala Val Trp Gly Leu Gly Val Asp Pro Ser Leu Gln
            20                  25                  30

Ile Asp Val Leu Thr Glu Leu Glu Leu Gly Glu Ser Thr Asp Gly Val
        35                  40                  45
```

```
Arg Gln Val Pro Gly Leu His Asn Gly Thr Lys Ala Phe Leu Phe Gln
 50                  55                  60

Glu Ser Pro Arg Ser Ile Lys Ala Ser Thr Ala Thr Ala Glu Arg Phe
 65                  70                  75                  80

Leu Gln Lys Leu Arg Asn Lys His Glu Phe Thr Ile Leu Val Thr Leu
                 85                  90                  95

Lys Gln Ile His Leu Asn Ser Gly Val Ile Leu Ser Ile His His Leu
                100                 105                 110

Asp His Arg Tyr Leu Glu Leu Glu Ser Ser Gly His Arg Asn Glu Ile
            115                 120                 125

Arg Leu His Tyr Arg Ser Gly Thr His Arg Pro His Thr Glu Val Phe
130                 135                 140

Pro Tyr Ile Leu Ala Asp Ala Lys Trp His Lys Leu Ser Leu Ala Phe
145                 150                 155                 160

Ser Ala Ser His Leu Ile Leu His Ile Asp Cys Asn Lys Ile Tyr Glu
                165                 170                 175

Arg Val Val Glu Met Pro Phe Thr Asp Leu Ala Leu Gly Thr Thr Phe
            180                 185                 190

Trp Leu Gly Gln Arg Asn Asn Ala His Gly Tyr Phe Lys Gly Ile Met
        195                 200                 205

Gln Asp Val His Val Leu Val Met Pro Gln Gly Phe Ile Ala Gln Cys
    210                 215                 220

Pro Asp Leu Asn Arg Thr Cys Pro Thr Cys Asn Asp Phe His Gly Leu
225                 230                 235                 240

Val Gln Lys Ile Met Glu Leu Gln Asp Ile Leu Ser Lys Thr Ser Ala
                245                 250                 255

Lys Leu Ser Arg Ala Glu Gln Arg Met Asn Arg Leu Asp Gln Cys Tyr
            260                 265                 270

Cys Glu Arg Thr Cys Thr Val Lys Gly Thr Thr Tyr Arg Glu Ser Glu
        275                 280                 285

Ser Trp Thr Asp Gly Cys Lys Asn Cys Thr Cys Leu Asn Gly Thr Ile
    290                 295                 300

Gln Cys Glu Thr Leu Val Cys Pro Ala Pro Asp Cys Pro Pro Lys Ser
305                 310                 315                 320

Ala Pro Ala Tyr Val Asp Gly Lys Cys Cys Lys Glu Cys Lys Ser Thr
                325                 330                 335

Cys Gln Phe Gln Gly Arg Ser Tyr Phe Glu Gly Glu Arg Asn Thr Ala
            340                 345                 350

Tyr Ser Ser Ser Gly Met Cys Val Leu Tyr Glu Cys Lys Asp Gln Thr
        355                 360                 365

Met Lys Leu Val Glu Asn Ile Gly Cys Pro Pro Leu Asp Cys Pro Glu
    370                 375                 380

Ser His Gln Ile Ala Leu Ser His Ser Cys Cys Lys Val Cys Lys Gly
385                 390                 395                 400

Tyr Asp Phe Cys Ser Glu Lys His Thr Cys Met Glu Asn Ser Val Cys
                405                 410                 415

Arg Asn Leu Asn Asp Arg Val Val Cys Ser Cys Arg Asp Gly Phe Arg
            420                 425                 430

Ala Leu Arg Glu Asp Asn Ala Tyr Cys Glu Asp Ile Asp Glu Cys Ala
        435                 440                 445

Glu Gly Arg His Tyr Cys Arg Glu Asn Thr Met Cys Val Asn Thr Pro
450                 455                 460
```

```
Gly Ser Phe Met Cys Val Cys Lys Thr Gly Tyr Ile Arg Ile Asp Asp
465                 470                 475                 480

Tyr Ser Cys Thr Glu His Asp Glu Cys Leu Thr Thr Gln His Asn Cys
                485                 490                 495

Asp Glu Asn Ala Leu Cys Phe Asn Thr Val Gly Gly His Asn Cys Val
            500                 505                 510

Cys Lys Pro Gly Tyr Thr Gly Asn Gly Thr Thr Cys Lys Ala Phe Cys
        515                 520                 525

Lys Asp Gly Cys Arg Asn Gly Gly Ala Cys Ile Ala Ala Asn Val Cys
    530                 535                 540

Ala Cys Pro Gln Gly Phe Thr Gly Pro Ser Cys Glu Thr Asp Ile Asp
545                 550                 555                 560

Glu Cys Ser Glu Gly Phe Val Gln Cys Asp Ser Arg Ala Asn Cys Ile
                565                 570                 575

Asn Leu Pro Gly Trp Tyr His Cys Glu Cys Arg Asp Gly Tyr His Asp
            580                 585                 590

Asn Gly Met Phe Ala Pro Gly Gly Glu Ser Cys Glu Asp Ile Asp Glu
        595                 600                 605

Cys Gly Thr Gly Arg His Ser Cys Thr Asn Asp Thr Ile Cys Phe Asn
    610                 615                 620

Leu Asp Gly Gly Tyr Asp Cys Arg Cys Pro His Gly Lys Asn Cys Thr
625                 630                 635                 640

Gly Asp Cys Val His Glu Gly Lys Val Lys His Thr Gly Gln Ile Trp
                645                 650                 655

Val Leu Glu Asn Asp Arg Cys Ser Val Cys Ser Trp Gln Thr Gly Phe
            660                 665                 670

Val Met Cys Arg Arg Met Val Cys Asp Cys Glu Asn Pro Thr Asp Asp
        675                 680                 685

Leu Ser Cys Cys Pro Glu Cys Asp Pro Arg Leu Ser Ser Gln Cys Leu
    690                 695                 700

His Gln Asn Gly Glu Thr Val Tyr Asn Ser Gly Asp Thr Trp Val Gln
705                 710                 715                 720

Asp Cys Arg Gln Cys Arg Cys Leu Gln Gly Glu Val Asp Cys Trp Pro
                725                 730                 735

Leu Ala Cys Pro Glu Val Glu Cys Glu Phe Ser Val Leu Pro Glu Asn
            740                 745                 750

Glu Cys Cys Pro Arg Cys Val Thr Asp Pro Cys Gln Ala Asp Thr Ile
        755                 760                 765

Arg Asn Asp Ile Thr Lys Thr Cys Leu Asp Glu Met Asn Val Val Arg
    770                 775                 780

Phe Thr Gly Ser Ser Trp Ile Lys His Gly Thr Glu Cys Thr Leu Cys
785                 790                 795                 800

Gln Cys Lys Asn Gly His Leu Cys Cys Ser Val Asp Pro Gln Cys Leu
                805                 810                 815

Gln Glu Leu
```

<210> SEQ ID NO 13
<211> LENGTH: 2453
<212> TYPE: DNA
<213> ORGANISM: Gallus gallus
<220> FEATURE:
<221> NAME/KEY: CDS
<222> LOCATION: (1)...(2453)

<400> SEQUENCE: 13

-continued

| | |
|---|---|
| atg gag tcc ggc tgc ggc tta ggc acg ctt tgc ctt ctc ctc tgc ctg<br>Met Glu Ser Gly Cys Gly Leu Gly Thr Leu Cys Leu Leu Leu Cys Leu<br>1                      5                      10                    15 | 48 |
| ggg cca gtc gta ggc ttc ggc gtg gac ccc tcg ctg cag atc gac gtg<br>Gly Pro Val Val Gly Phe Gly Val Asp Pro Ser Leu Gln Ile Asp Val<br>                  20                      25                    30 | 96 |
| ctg tcc gag ctg ggg ctg ccg ggc tac gcg gcg ggc gtg cgc cag gtg<br>Leu Ser Glu Leu Gly Leu Pro Gly Tyr Ala Ala Gly Val Arg Gln Val<br>         35                      40                    45 | 144 |
| ccg ggg ctg cac aac ggg agc aaa gcc ttc ctc ttc cca gat act tca<br>Pro Gly Leu His Asn Gly Ser Lys Ala Phe Leu Phe Pro Asp Thr Ser<br>50                      55                      60 | 192 |
| aga agt gta aag gcg tct cca gaa aca gct gaa atc ttt ttt cag aag<br>Arg Ser Val Lys Ala Ser Pro Glu Thr Ala Glu Ile Phe Phe Gln Lys<br>65                      70                      75                    80 | 240 |
| ttg aga aat aaa tat gaa ttc aca atc ctg gtg acc tta aaa caa gcc<br>Leu Arg Asn Lys Tyr Glu Phe Thr Ile Leu Val Thr Leu Lys Gln Ala<br>                  85                      90                    95 | 288 |
| cat tta aat tca ggg gtt att ttc tct att cat cac tta gat cac agg<br>His Leu Asn Ser Gly Val Ile Phe Ser Ile His His Leu Asp His Arg<br>                100                    105                    110 | 336 |
| tat ctg gaa ttg gaa agc agc ggt cat cga aat gaa atc agg ttg cat<br>Tyr Leu Glu Leu Glu Ser Ser Gly His Arg Asn Glu Ile Arg Leu His<br>         115                      120                    125 | 384 |
| tac cgt aca ggc agt cat cgc tcc cac aca gaa gta ttc cca tac atc<br>Tyr Arg Thr Gly Ser His Arg Ser His Thr Glu Val Phe Pro Tyr Ile<br>130                      135                      140 | 432 |
| ctg gca gac gat aag tgg cac agg ctt tcc tta gca atc agt gcc tct<br>Leu Ala Asp Asp Lys Trp His Arg Leu Ser Leu Ala Ile Ser Ala Ser<br>145                      150                      155                    160 | 480 |
| cac ttg att tta cac gtg gac tgc aat aaa atc tat gaa aga gtt gtg<br>His Leu Ile Leu His Val Asp Cys Asn Lys Ile Tyr Glu Arg Val Val<br>                165                    170                    175 | 528 |
| gag aag ccc ttc atg gac tta cct gtg ggt aca acc ttt tgg cta gga<br>Glu Lys Pro Phe Met Asp Leu Pro Val Gly Thr Thr Phe Trp Leu Gly<br>         180                      185                    190 | 576 |
| cag agg aat aat gca cac ggt tat ttt aag ggc ata atg caa gat gtg<br>Gln Arg Asn Asn Ala His Gly Tyr Phe Lys Gly Ile Met Gln Asp Val<br>         195                      200                    205 | 624 |
| caa tta ctt gtc atg cct caa gga ttt att tct cag tgc cca gat ctt<br>Gln Leu Leu Val Met Pro Gln Gly Phe Ile Ser Gln Cys Pro Asp Leu<br>210                      215                      220 | 672 |
| aat cgg aca tgc cca act tgt aat gat ttc cat gga ctt gtg cag aaa<br>Asn Arg Thr Cys Pro Thr Cys Asn Asp Phe His Gly Leu Val Gln Lys<br>225                      230                      235                    240 | 720 |
| att atg gaa ctg caa gac att tta gct aaa acg tca gct aag ctg tcg<br>Ile Met Glu Leu Gln Asp Ile Leu Ala Lys Thr Ser Ala Lys Leu Ser<br>                245                    250                    255 | 768 |
| caa gct gag cag agg atg aac aag ttg gat cag tgc tat tgt gaa agg<br>Gln Ala Glu Gln Arg Met Asn Lys Leu Asp Gln Cys Tyr Cys Glu Arg<br>         260                      265                    270 | 816 |
| acc tgc aca atg aaa ggc atg aca tac aga gaa ttt gaa tcc tgg aca<br>Thr Cys Thr Met Lys Gly Met Thr Tyr Arg Glu Phe Glu Ser Trp Thr<br>275                      280                      285 | 864 |
| gat ggt tgt aag aac tgc act tgc atg aat ggc act gtg cag tgt gaa<br>Asp Gly Cys Lys Asn Cys Thr Cys Met Asn Gly Thr Val Gln Cys Glu<br>         290                      295                    300 | 912 |
| gct ttg att tgc tcc ctc tct gac tgt cca cct aat tct gcc ctg tca<br>Ala Leu Ile Cys Ser Leu Ser Asp Cys Pro Pro Asn Ser Ala Leu Ser<br>305                      310                      315                    320 | 960 |

-continued

```
tac gtg gat ggc aag tgc tgc aaa gaa tgt caa tcg gtg tgc ata ttt      1008
Tyr Val Asp Gly Lys Cys Cys Lys Glu Cys Gln Ser Val Cys Ile Phe
                325                 330                 335 gaa ggc aga acc tac ttt gaa gga caa aga gaa acg gtg tat tca agc      1056
Glu Gly Arg Thr Tyr Phe Glu Gly Gln Arg Glu Thr Val Tyr Ser Ser
            340                 345                 350 tca ggg gac tgt gtt ctg ttt gag tgc aag gac cac aaa atg cag cgt      1104
Ser Gly Asp Cys Val Leu Phe Glu Cys Lys Asp His Lys Met Gln Arg
        355                 360                 365 att cca aaa gac agt tgt gca act ttg aac tgc ccg gaa tct caa cag      1152
Ile Pro Lys Asp Ser Cys Ala Thr Leu Asn Cys Pro Glu Ser Gln Gln
    370                 375                 380 atc cca tta tct cac agt tgc tgc aaa atc tgt aaa ggc cat gac ttt      1200
Ile Pro Leu Ser His Ser Cys Cys Lys Ile Cys Lys Gly His Asp Phe
385                 390                 395                 400 tgc act gaa gga cat aac tgt atg gag cat tct gtc tgc cga aac cta      1248
Cys Thr Glu Gly His Asn Cys Met Glu His Ser Val Cys Arg Asn Leu
                405                 410                 415 gat gac aga gct gtc tgt agc tgc cga gat ggc ttc cgg gcc ctt cgg      1296
Asp Asp Arg Ala Val Cys Ser Cys Arg Asp Gly Phe Arg Ala Leu Arg
            420                 425                 430 gag gac aat gcc tac tgt gaa gat gtt gat gag tgt gcc gag ggg cag      1344
Glu Asp Asn Ala Tyr Cys Glu Asp Val Asp Glu Cys Ala Glu Gly Gln
        435                 440                 445 cac tac tgt cgg gag aac acc atg tgt gta aat aca cca gga tcc ttc      1392
His Tyr Cys Arg Glu Asn Thr Met Cys Val Asn Thr Pro Gly Ser Phe
    450                 455                 460 atg tgc atc tgc aaa aca gga tat ata cgc att gat gac tat tca tgt      1440
Met Cys Ile Cys Lys Thr Gly Tyr Ile Arg Ile Asp Asp Tyr Ser Cys
465                 470                 475                 480 aca gag cac gat gaa tgt gta aca aac cag cac aac tgt gat gaa aat      1488
Thr Glu His Asp Glu Cys Val Thr Asn Gln His Asn Cys Asp Glu Asn
                485                 490                 495 gcg cta tgt ttc aac acg gtg ggt ggg cac aac tgt gtc tgc aag ctg      1536
Ala Leu Cys Phe Asn Thr Val Gly Gly His Asn Cys Val Cys Lys Leu
            500                 505                 510 ggt tac aca gga aat ggg acg gtg tgt aaa gca ttt tgc aaa gat ggg      1584
Gly Tyr Thr Gly Asn Gly Thr Val Cys Lys Ala Phe Cys Lys Asp Gly
        515                 520                 525 tgc agg aat gga gga gcc tgt att gct tcc aac gtg tgt gcc tgc cca      1632
Cys Arg Asn Gly Gly Ala Cys Ile Ala Ser Asn Val Cys Ala Cys Pro
    530                 535                 540 caa ggc ttc act ggc ccc agc tgt gaa act gac att gat gaa tgc tct      1680
Gln Gly Phe Thr Gly Pro Ser Cys Glu Thr Asp Ile Asp Glu Cys Ser
545                 550                 555                 560 gat ggc ttt gtg cag tgt gac agc cgt gct aat tgc atc aat ctg cca      1728
Asp Gly Phe Val Gln Cys Asp Ser Arg Ala Asn Cys Ile Asn Leu Pro
                565                 570                 575 ggg tgg tac cac tgt gaa tgc agg gat ggc tac cat gac aat ggg atg      1776
Gly Trp Tyr His Cys Glu Cys Arg Asp Gly Tyr His Asp Asn Gly Met
            580                 585                 590 ttt tca cca agt gga gaa tcc tgt gaa gac att gat gaa tgt gca act      1824
Phe Ser Pro Ser Gly Glu Ser Cys Glu Asp Ile Asp Glu Cys Ala Thr
        595                 600                 605 gga agg cat agc tgt gcc aat gac act gtt tgc ttt aac ctg gat ggt      1872
Gly Arg His Ser Cys Ala Asn Asp Thr Val Cys Phe Asn Leu Asp Gly
    610                 615                 620 ggg tat gac tgt cga tgt cca cat ggc aag aac tgc aca gga gac tgt      1920
Gly Tyr Asp Cys Arg Cys Pro His Gly Lys Asn Cys Thr Gly Asp Cys
```

```
                625                 630                 635                 640
atc cat gaa gac aaa atc aag cac aat ggt cag att tgg gtg ctg gag    1968
Ile His Glu Asp Lys Ile Lys His Asn Gly Gln Ile Trp Val Leu Glu
                645                 650                 655 aac gac aga tgc tct gtc tgc tca tgc cag agt gga tac gtg atg tgc    2016
Asn Asp Arg Cys Ser Val Cys Ser Cys Gln Ser Gly Tyr Val Met Cys
                660                 665                 670 cgg cga atg gtc tgt gac tgt gaa aat ccc act gtt gac ctc ttt tgc    2064
Arg Arg Met Val Cys Asp Cys Glu Asn Pro Thr Val Asp Leu Phe Cys
                675                 680                 685 tgt cct gag tgt gac cca agg ctc agc agt caa tgt tta cat cag agt    2112
Cys Pro Glu Cys Asp Pro Arg Leu Ser Ser Gln Cys Leu His Gln Ser
                690                 695                 700 ggg gag ctt tcc tac aac agt ggt gac tcc tgg ata caa aac tgt cag    2160
Gly Glu Leu Ser Tyr Asn Ser Gly Asp Ser Trp Ile Gln Asn Cys Gln
705                 710                 715                 720 cag tgt cgc tgc ttg caa gga gag gtt gac tgt tgg ccc tta ccg tgc    2208
Gln Cys Arg Cys Leu Gln Gly Glu Val Asp Cys Trp Pro Leu Pro Cys
                725                 730                 735 cca gag gta gac tgt gag ttc agt gtc ctc cct gag aat gag tgc tgc    2256
Pro Glu Val Asp Cys Glu Phe Ser Val Leu Pro Glu Asn Glu Cys Cys
                740                 745                 750 cca cgc tgt gtc act gac ccc tgc caa gcg gac acc atc cgt aat gac    2304
Pro Arg Cys Val Thr Asp Pro Cys Gln Ala Asp Thr Ile Arg Asn Asp
                755                 760                 765 atc acc aaa acc tgc ctg gat gaa acc aat gtt gtt cgc ttc act gga    2352
Ile Thr Lys Thr Cys Leu Asp Glu Thr Asn Val Val Arg Phe Thr Gly
770                 775                 780 tct tct tgg att aag cat ggc aca gag tgc aca ctc tgc caa tgt aag    2400
Ser Ser Trp Ile Lys His Gly Thr Glu Cys Thr Leu Cys Gln Cys Lys
785                 790                 795                 800 aat ggc cac gtc tgt tgc tca gtg gat cca cag tgc ctt cag gaa ctg    2448
Asn Gly His Val Cys Cys Ser Val Asp Pro Gln Cys Leu Gln Glu Leu
                805                 810                 815 tga ca                                                              2453
*
```

<210> SEQ ID NO 14
<211> LENGTH: 816
<212> TYPE: PRT
<213> ORGANISM: Gallus gallus

<400> SEQUENCE: 14

```
Met Glu Ser Gly Cys Gly Leu Gly Thr Leu Cys Leu Leu Cys Leu
1               5                   10                  15

Gly Pro Val Val Gly Phe Gly Val Asp Pro Ser Leu Gln Ile Asp Val
                20                  25                  30

Leu Ser Glu Leu Gly Leu Pro Gly Tyr Ala Ala Gly Val Arg Gln Val
            35                  40                  45

Pro Gly Leu His Asn Gly Ser Lys Ala Phe Leu Phe Pro Asp Thr Ser
        50                  55                  60

Arg Ser Val Lys Ala Ser Pro Glu Thr Ala Glu Ile Phe Phe Gln Lys
65                  70                  75                  80

Leu Arg Asn Lys Tyr Glu Phe Thr Ile Leu Val Thr Leu Lys Gln Ala
                85                  90                  95

His Leu Asn Ser Gly Val Ile Phe Ser Ile His His Leu Asp His Arg
            100                 105                 110

Tyr Leu Glu Leu Glu Ser Ser Gly His Arg Asn Glu Ile Arg Leu His
```

-continued

```
            115                 120                 125
Tyr Arg Thr Gly Ser His Arg Ser His Thr Glu Val Phe Pro Tyr Ile
130                 135                 140
Leu Ala Asp Asp Lys Trp His Arg Leu Ser Leu Ala Ile Ser Ala Ser
145                 150                 155                 160
His Leu Ile Leu His Val Asp Cys Asn Lys Ile Tyr Glu Arg Val Val
                165                 170                 175
Glu Lys Pro Phe Met Asp Leu Pro Val Gly Thr Thr Phe Trp Leu Gly
                180                 185                 190
Gln Arg Asn Asn Ala His Gly Tyr Phe Lys Gly Ile Met Gln Asp Val
                195                 200                 205
Gln Leu Leu Val Met Pro Gln Gly Phe Ile Ser Gln Cys Pro Asp Leu
210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Gln Ala Glu Gln Arg Met Asn Lys Leu Asp Gln Cys Tyr Cys Glu Arg
                260                 265                 270
Thr Cys Thr Met Lys Gly Met Thr Tyr Arg Glu Phe Glu Ser Trp Thr
                275                 280                 285
Asp Gly Cys Lys Asn Cys Thr Cys Met Asn Gly Thr Val Gln Cys Glu
                290                 295                 300
Ala Leu Ile Cys Ser Leu Ser Asp Cys Pro Pro Asn Ser Ala Leu Ser
305                 310                 315                 320
Tyr Val Asp Gly Lys Cys Cys Lys Glu Cys Gln Ser Val Cys Ile Phe
                325                 330                 335
Glu Gly Arg Thr Tyr Phe Glu Gly Gln Arg Glu Thr Val Tyr Ser Ser
                340                 345                 350
Ser Gly Asp Cys Val Leu Phe Glu Cys Lys Asp His Lys Met Gln Arg
                355                 360                 365
Ile Pro Lys Asp Ser Cys Ala Thr Leu Asn Cys Pro Glu Ser Gln Gln
                370                 375                 380
Ile Pro Leu Ser His Ser Cys Cys Lys Ile Cys Lys Gly His Asp Phe
385                 390                 395                 400
Cys Thr Glu Gly His Asn Cys Met Glu His Ser Val Cys Arg Asn Leu
                405                 410                 415
Asp Asp Arg Ala Val Cys Ser Cys Arg Asp Gly Phe Arg Ala Leu Arg
                420                 425                 430
Glu Asp Asn Ala Tyr Cys Glu Asp Val Asp Glu Cys Ala Glu Gly Gln
                435                 440                 445
His Tyr Cys Arg Glu Asn Thr Met Cys Val Asn Thr Pro Gly Ser Phe
                450                 455                 460
Met Cys Ile Cys Lys Thr Gly Tyr Ile Arg Ile Asp Asp Tyr Ser Cys
465                 470                 475                 480
Thr Glu His Asp Glu Cys Val Thr Asn Gln His Asn Cys Asp Glu Asn
                485                 490                 495
Ala Leu Cys Phe Asn Thr Val Gly Gly His Asn Cys Val Cys Lys Leu
                500                 505                 510
Gly Tyr Thr Gly Asn Gly Thr Val Cys Lys Ala Phe Cys Lys Asp Gly
                515                 520                 525
Cys Arg Asn Gly Gly Ala Cys Ile Ala Ser Asn Val Cys Ala Cys Pro
530                 535                 540
```

-continued

```
Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
                580                 585                 590

Phe Ser Pro Ser Gly Glu Ser Cys Glu Asp Ile Asp Glu Cys Ala Thr
            595                 600                 605

Gly Arg His Ser Cys Ala Asn Asp Thr Val Cys Phe Asn Leu Asp Gly
        610                 615                 620

Gly Tyr Asp Cys Arg Cys Pro His Gly Lys Asn Cys Thr Gly Asp Cys
625                 630                 635                 640

Ile His Glu Asp Lys Ile Lys His Asn Gly Gln Ile Trp Val Leu Glu
                645                 650                 655

Asn Asp Arg Cys Ser Val Cys Ser Cys Gln Ser Gly Tyr Val Met Cys
                660                 665                 670

Arg Arg Met Val Cys Asp Cys Glu Asn Pro Thr Val Asp Leu Phe Cys
            675                 680                 685

Cys Pro Glu Cys Asp Pro Arg Leu Ser Ser Gln Cys Leu His Gln Ser
        690                 695                 700

Gly Glu Leu Ser Tyr Asn Ser Gly Asp Ser Trp Ile Gln Asn Cys Gln
705                 710                 715                 720

Gln Cys Arg Cys Leu Gln Gly Glu Val Asp Cys Trp Pro Leu Pro Cys
                725                 730                 735

Pro Glu Val Asp Cys Glu Phe Ser Val Leu Pro Glu Asn Glu Cys Cys
                740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Thr Asn Val Val Arg Phe Thr Gly
        770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815
```

COMPOSITION FOR PROMOTING CARTILAGE FORMATION OR REPAIR COMPRISING A NELL GENE PRODUCT AND METHOD OF TREATING CARTILAGE-RELATED CONDITIONS USING SUCH COMPOSITION

CROSS-REFERENCE TO RELATED APPLICATIONS

This application is a continuation-in-part of U.S. application Ser. No. 10/527,786, filed on Sep. 28, 2005, which is a U.S. National Phase of international application No. PCT/US 2003/29281, filed on Sep. 15, 2003, which claims priority to U.S. provisional application No. 60/410,846, filed on Sep. 13, 2002; U.S. Ser. No. 10/527,786 is now abandoned.

This application is also a continuation-in-part of U.S. application Ser. No. 10/544,553, filed on May 15, 2006, now U.S. Pat. No.7,544,486, which is a U.S. National Phase of PCT application PCT/US2004/003808, filed on Feb. 9, 2004, which claims priority to U.S. provisional application No. 60/445,672, filed on Feb. 7, 2003, and PCT/US2003/29281, filed on Sep. 15, 2003, the teachings of which are incorporated herein by reference. This application is also a continuation-in-part of international application No. PCT/US2006/005473, filed on Feb. 16, 2006, which claims priority to U.S. Provisional Application No. 60/653,722 filed on Feb. 16, 2005. This application is also a continuation-in-part of U.S. application Ser. No. 11/392,294, filed on Mar. 28, 2006, which is a continuation application of U.S. application Ser. No. 09/412,297, filed on Oct. 5, 1999, issued as U.S. Pat. No. 7,052,856.

STATEMENT AS TO RIGHTS TO INVENTIONS MADE UNDER FEDERALLY SPONSORED RESEARCH AND DEVELOPMENT

Part of this work was supported by NIH/NIDR grant number DE9400 and CRC/NIH grant number RR00865, NIH/NIDCR RO3 DE 014649-01, NIH/NIDCR K23DE00422, NIH DE016107-01, and NIH/SBIR R43-DE016781-01. The Government of the United States of America has certain rights in this invention.

FIELD OF THE INVENTION

The invention generally relates to a composition for cartilage formation or regeneration.

BACKGROUND OF THE INVENTION

Growth factors are substances, such as peptides, which affect the growth and differentiation of defined populations of cells in vivo or in vitro.

Cartilage is a type of dense connective tissue. It is composed of chondrocytes which are dispersed in a firm gel-like matrix. Cartilage is avascular (contains no blood vessels) and nutrients are diffused through the matrix. Cartilage is found in the joints, the rib cage, the ear, the nose, in the throat and between intervertebral disks. There are three main types of cartilage: hyaline (e.g., costal cartilages, the cartilages of the nose, trachea, and bronchi, and the articular cartilages of joints), elastic (e.g., external ear, external auditory meatus, part of the Eustachian tube, epiglottis, and in some of the laryngeal cartilages) and fibrocartilage [e.g. meniscus (e.g., wrist triangular fibrocartilage complex, knee meniscus), intervertebral discs, temporomandibular joint disc, the pubic symphysis, and in some tendons and ligaments at their attachment to bones. One of the main purposes of cartilage is to provide a framework upon which bone deposition could begin (i.e., during endochondral ossification). Another important purpose of cartilage is to provide smooth surfaces for the movement of articulating bones. For example, articular cartilage, most notably that which is found in the knee joint, is generally characterized by very low friction, high wear resistance, and poor regenerative qualities. It is responsible for much of the compressive resistance and load bearing qualities of the knee joint and, without it, walking is painful to impossible. Yet another important purpose of cartilage is to provide, firm, yet flexible support (e.g., nasal cartilage, spinal discs, tracheal cartilage, knee meniscus, bronchial cartilage). For instance, cartilage such as the meniscus plays a crucial role in joint stability, lubrication, and force transmission. Under a weight bearing load, the meniscus maintains the balanced position of the femur on the tibia and distributes the compressive forces by increasing the surface contact area, thereby decreasing the average stress two to three times. Additionally, the menisci interact with the joint fluid to produce a coefficient of friction that is five times as slick as ice on ice. In another example, the intervertebral disc has several important functions, including functioning as a spacer, as a shock absorber, and as a motion unit. The gelatinous central portion of the disc is called the nucleus pulposus. It is composed of 80-90% water. The solid portion of the nucleus is Type II collagen and non-aggregated proteoglycans. The outer ligamentous ring around the nucleus pulposus is called the annulus fibrosus, which hydraulically seals the nucleus, and allows intradiscal pressures to rise as the disc is loaded. The annulus has overlapping radial bands, not unlike the plies of a radial tire, and this allows torsional stresses to be distributed through the annulus under normal loading without rupture. The disc functions as a hydraulic cylinder. The annulus interacts with the nucleus. As the nucleus is pressurized, the annular fibers serve a containment function to prevent the nucleus from bulging or herniating.

Cartilage can be damaged by wear, injury or diseases. As we age, the water and protein content of the body's cartilage changes. This change results in weaker, more fragile and thin cartilage. Osteoarthritis is a common condition of cartilage failure that can lead to limited range of motion, bone damage and invariably, pain. Due to a combination of acute stress and chronic fatigue, osteoarthritis directly manifests itself in a wearing away of the articulating surface and, in extreme cases, bone can be exposed in the joint. In another example, loss of the protective stabilizing meniscus leads to increased joint laxity or abnormal motions that lead to joint instability. The excessive motion and narrowed contact area promotes early arthritic changes. At the cellular level, there is initially a loss of cells from the superficial layer of the articular cartilage followed by cartilage splitting, subsequent thinning and erosion occurs, and finally protrusion of the underlying raw bone. The earliest arthritic changes have been noted three weeks after loss of the entire meniscus. In yet another example, because both the discs and the joints that stack the vertebrae (facet joints) are partly composed of cartilage, these areas are subject to wear and tear over time (degenerative changes). As the inner nucleus dehydrates, the disc space narrows, and redundant annular ligaments bulge. With progressive nuclear dehydration, the annular fibers can crack and tear. Loss of normal soft tissue tension may allow the spinal segment to sublux (e.g. partial dislocation of the joint), leading to osteophyte formation (bone spurs), foraminal narrowing, mechanical instability, and pain. If the annular fibers stretch or rupture, allowing the pressurized nuclear material to bulge or herniate and compress neural tissues, pain and weakness may result. This is the condition called a pinched nerve, slipped disc, or herniated disc. Radiculopathy refers to nerve irritation caused by damage to the disc between the vertebrae. Mechanical dysfunction may also cause disc degeneration and pain (e.g. degenerative disc disease). For example, the disc may be damaged as the result of some trauma that overloads the capacity of the disc to withstand increased forces passing through it, and inner or outer portions of the annular fibers may tear. These torn fibers may be the focus for inflammatory response when they are subjected to increased stress, and may cause pain directly, or through the compensatory protective spasm of the deep paraspinal muscles.

There are several different repair options available for cartilage damage or failure. Osteoarthritis is the second leading cause of disability in the elderly population in the United States. It is a degenerative disorder that generally starts off relatively mild and escalates with time and wear. For those patients experiencing mild to moderate symptoms, the disorder can be dealt with by several non-surgical treatments. The use of braces and drug therapies, such as anti-inflammatories (ex. diclofenac, ibuprofen, and naproxen), COX-2 selective inhibitors, hydrocortisone, glucosamine, and chondroitin sulfate, have been shown to alleviate the pain caused by cartilage deficiency and some claim they can slow the degenerative process.

Most surgical treatments for articular cartilage, short of total joint replacement, can be divided into various treatment groups. Treatments that remove the diseased and undermined cartilage with an aim to stop inflammation and pain include shaving (chondrectomy) and debridement. Another group of treatments consists of a range of abrasive procedures aimed at triggering cartilage production, such as drilling, microfracture surgery, chondroplasty, and spongialization. Abrasion, drilling, and microfracture originated 20 years ago. They rely on the phenomenon of spontaneous repair of the cartilage tissue following vascular injury to the subchondral plate of the bone. Laser assisted treatments, currently experimental, compose another category; they combine the removal of diseased cartilage with cartilage reshaping and also induce cartilage proliferation. Additional treatments include autologous cartilage implants (e.g., Carticel by Genzyme). Other treatments, more applicable to meniscal cartilage, include early surgical intervention and suture repair of torn structures or allograft meniscus transplantation in severe injury cases.

Although the overwhelming majority of patients with a herniated disc and sciatica heal without surgery, if surgery is indicated procedures include removal of the herniated disc with laminotomy (producing a small hole in the bone of the spine surrounding the spinal cord), laminectomy (removal of the bony wall adjacent to the nerve tissues), by needle technique through the skin (percutaneous discectomy), disc-dissolving procedures (chemonucleolysis), and others. For patients with mechanical pain syndrome, unresponsive to conservative treatment, and disabling to the individual's way of life, the problem can be addressed by spinal fusion, intradiscal electrothermal coagulation (or annuloplasty), posterior dynamic stabilization, artificial disc technologies, or still experimental disc regeneration therapies using various molecular based therapies delivered using proteins, peptides, gene therapies, or nucleotides. Although numerous methods have been described for treatment of cartilage problems, it is clear that many are artificial or mechanically based solutions that do not seek to recreate normal cartilage tissue biology. Therefore, there is a need for methods for stimulating cartilage formation.

The embodiments described below address the above identified issues and needs.

SUMMARY OF THE INVENTION

The present invention is related to agents and methods for inducing cartilage formation or repair using a NELL peptide or related agent (collectively referred as "agent"). The composition can include a NELL peptide, a Nell-like molecule, and optionally at least one other active agent, cells, and biocompatible material implanted for the purpose of cartilage repair (i.e., hyaline cartilage, elastic cartilage, or fibrocartilage).

In some embodiments, the present invention provides a composition that contains an effective amount of at least one agent for either directly or indirectly promoting the generation of cartilage for treating, preventing or ameliorating a cartilage related medical condition. One of the agents for direct promotion of cartilage generation can be NELL peptides or NELL-based gene therapy or NELL-gene product enhancers applied to chondrogenic cells such as, but not limited to, chondroblasts, chondrocytes, or chondroprogenitor cells, adult and embryonic stem cells, bone marrow cells, bone marrow stromal cells, mesenchymal cells, a fibroblast, or adipose derived cells. The agent for indirect promotion of cartilage generation (e.g., through inducing chondroblast/chondrocyte differentiation) can be, e.g., one of NELL peptide, or agonists of NELL peptide receptors.

In some embodiments, the composition can include, e.g., one or more inhibitors or antagonists of NELL peptide receptors, high dose NELL peptides, or combinations thereof. Such a composition is effective for inhibition of chondrogenic differentiation by inhibiting potential or committed chondrogenic cells such as, but not limited to, osteoblasts, osteoprogenitor cells, stem cells, bone marrow cells, fibroblastic cells, dural cells, periosteal cells, pericytes, and/or muscle cells.

BRIEF DESCRIPTION OF THE DRAWINGS

FIGS. 2A and 2B with arrows pointing at the meniscus between the femoral and tibial cartilage head in wild type (FIG. 2A) and NELL1 overexpression (FIG. 2B) animals. FIGS. 2C and 2D are higher magnification views of FIGS. 2A and 2B. FIG. 2E is a higher magnification of the wild type control shown in 2C demonstrating less differentiated chondrocytes with minimal hypertrophy. FIG. 2F is a higher magnification of the NELL1 overexpression animal shown in 2D demonstrating significantly more differentiated chondrocyte in the cartilage matrix. Vacuoles in the hypertrophic chondrocytes are observed indicating well differentiation of chondrocyte in the meniscus.

FIG. 3A shows the efficiency of adenoviral (Ad) transduction with significant number of positively stained cells expressing beta-galactosidase. FIG. 3B is a Western gel demonstrating significant NELL1 protein expression in the AdNELL1 transduced goat chondrocytes (relative to beta-actin controls) and no NELL1 protein expression in Ad BMP2 or AdLacZ (control) transduced goat chondrocytes.

FIG. 5A demonstrates undesirable mineralization (red coloring) in the AdBMP2 transduced specimens but not AdNELL1 or AdLacZ specimens. FIG. 5B demonstrates that NELL1 induces significantly more cartilage mass than AdLacZ controls. FIG. 5C demonstrates that AdBMP2 significantly increased density (another indicator of mineralization) in the specimens.

DETAILED DESCRIPTION

The present invention is related to agents and methods for inducing cartilage formation or repair using a NELL peptide or related agent (collectively referred as "agent"). The composition can include a NELL peptide, a Nell-like molecule, and optionally at least one other active agent, cells, and biocompatible material implanted for the purpose of articular cartilage repair.

In some embodiments, the present invention provides a composition that contains an effective amount of at least one agent for either directly or indirectly promoting the generation of cartilage for treating, preventing or ameliorating a cartilage related medical condition. One of the agents for direct promotion of cartilage generation can be NELL peptides applied to chondrogenic cells such as, but not limited to, chondroblasts, chondrocytes, or chondroprogenitor cells, stem cells, bone marrow cells, a bone marrow stromal cells, a fibroblast, or adipose derived cells. The agent for indirect promotion of cartilage generation (e.g., through inducing chondroblast/chondrocyte differentiation) can be, e.g., one of NELL peptide, or agonists of NELL peptide receptors.

In some embodiments, the present invention includes a systemic or local application of the composition described herein to a mammalian subject (e.g., a human being) to promote cartilage formation or regeneration.

In some embodiments, the composition can include, e.g., one or more inhibitors or antagonists of NELL peptide receptors, high dose NELL peptides, or combinations thereof. Such a composition is effective for inhibition of chondrogenic differentiation by inhibiting potential or committed chondrogenic cells such as, but not limited to, osteoblasts, osteoprogenitor cells, stem cells, bone marrow cells, fibroblastic cells, dural cells, periosteal cells, pericytes, and/or muscle cells.

The effectiveness of the present invention for cartilage formation or regeneration are shown in FIGS. 1-10.

Figure 1:
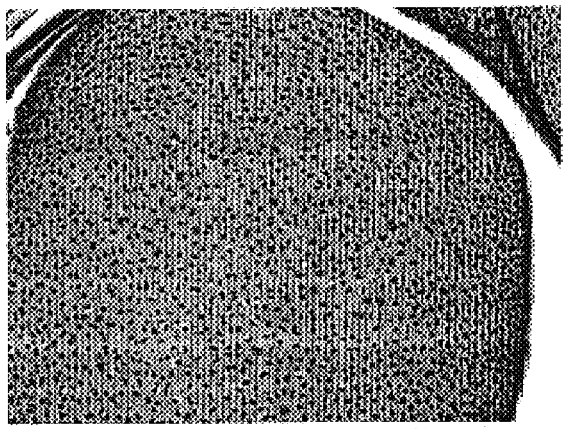
FIG. 1 shows increased cartilage maturation and hypertrophy in femoral head cartilage of NELL1 overexpression mice compared with wild type littermate. On the left is wild type newborn femoral head cartilage demonstrating small, less mature chondrocytes in the femoral head. On the right is the NELL1 over-expression transgenic mice demonstrating well differentiated, more mature, hypertrophic chondrocytes present throughout the femoral head with large nuclei and vacuoles present.
Figure 1:
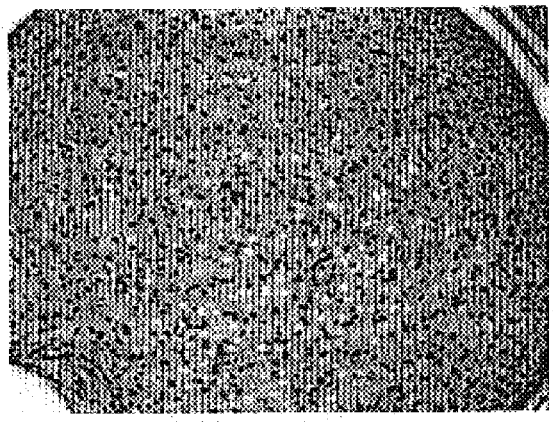
Figure 1:
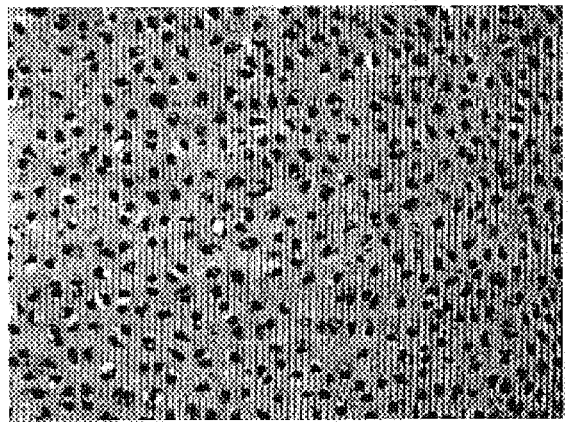
Figure 1:
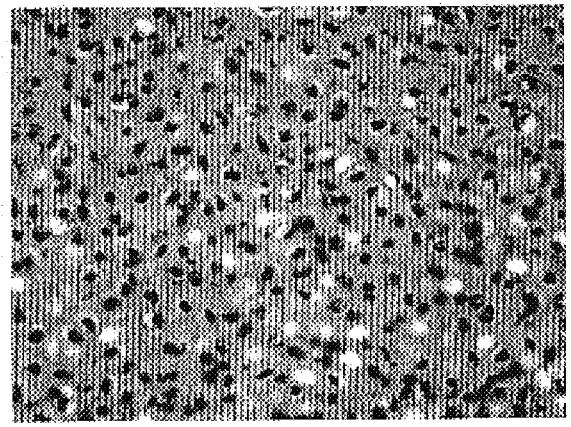
Figure 2:
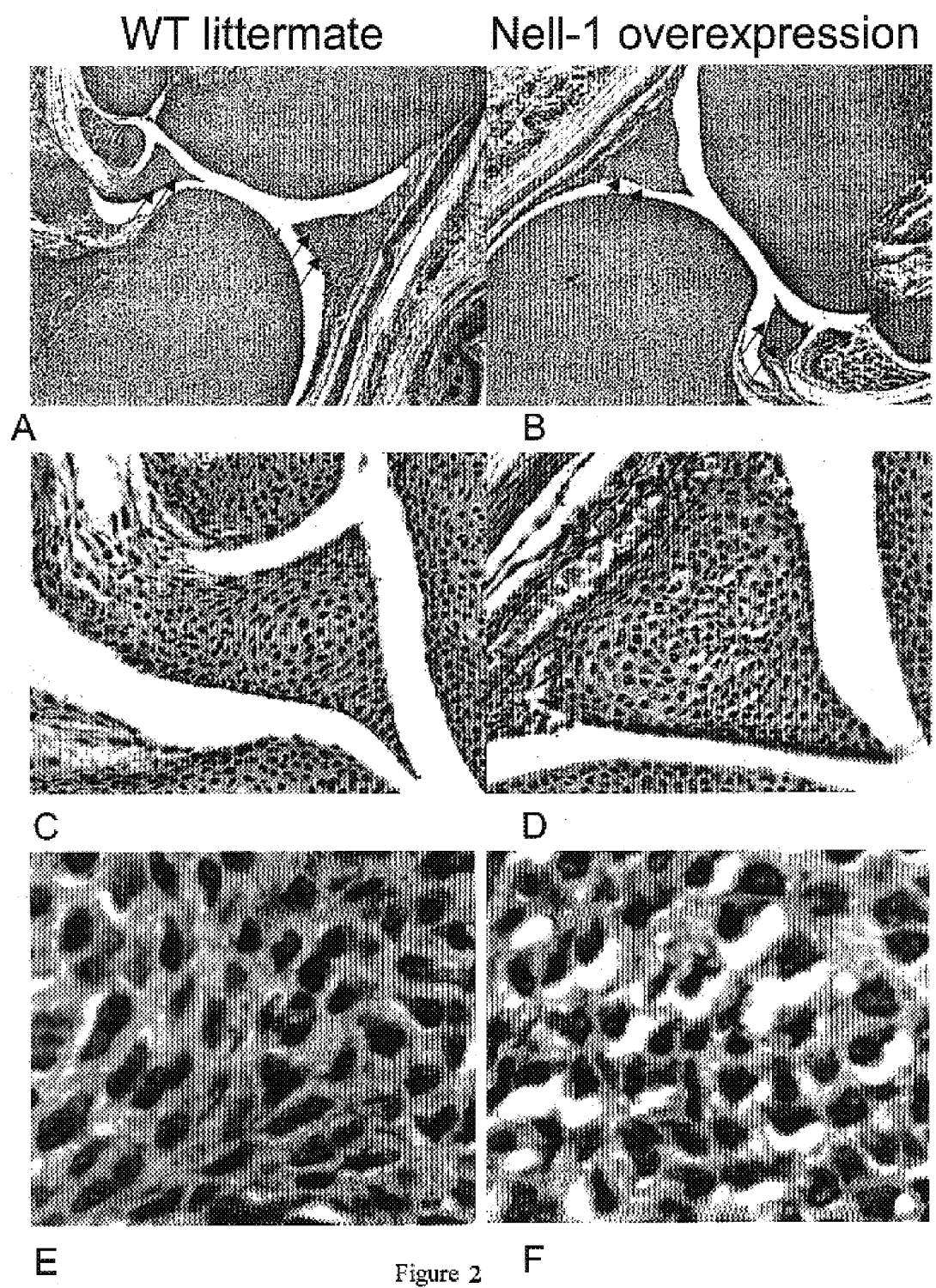
FIGS. 2A-2F show increased meniscus development in E18 NELL1 overexpression mice compared with wild type littermate.

FIG. 1 shows increased cartilage maturation and hypertrophy in femoral head cartilage of NELL1 overexpression mice compared with wild type littermate. On the left is wild type newborn femoral head cartilage demonstrating small, less mature chondrocytes in the femoral head. On the right is the NELL1 over-expression transgenic mice demonstrating well differentiated, more mature, hypertrophic chondrocytes present throughout the femoral head with large nuclei and vacuoles present. Note the absence of mineralization in the hypertrophied cartilage. These studies demonstrate that NELL1 increases chondrocyte maturation, hypertrophy without necessarily inducing mineralization.

FIGS. 2A-2F show increased meniscus development in E18 NELL1 overexpression mice compared with wild type littermate. FIGS. 2A and 2B with arrows pointing at the meniscus between the femoral and tibial cartilage head in wild type (FIG. 2A) and NELL1 overexpression (FIG. 2B) animals. FIGS. 2C and 2D are higher magnification views of FIGS. 2A and 2B. FIG. 2E is a higher magnification of the wild type control shown in 2C demonstrating less differentiated chondrocytes with minimal hypertrophy. FIG. 2F is a higher magnification of the NELL1 overexpression animal shown in 2D demonstrating significantly more differentiated chondrocyte in the cartilage matrix. Vacuoles in the hypertrophic chondrocytes are observed indicating well differentiation of chondrocyte in the meniscus. This data indicates that Nell-1 can promote meniscus formation and differentiation.

Figure 3A:
FIGS. 3A and 3B show adenovirus transduction of goat primary chondrocytes isolated from auricular cartilage.
Figure 3B:

FIGS. 3A and 3B show adenovirus transduction of goat primary chondrocytes isolated from auricular cartilage. FIG. 3A shows the efficiency of adenoviral (Ad) transduction with significant number of positively stained cells expressing beta-galactosidase. FIG. 3B is a Western gel demonstrating significant NELL1 protein expression in the AdNELL1 transduced goat chondrocytes (relative to beta-actin controls) and no NELL1 protein expression in AdBMP2 or AdLacZ (control) transduced goat chondrocytes. These studies demonstrate that there is efficient adenoviral transduction and that AdNELL1, but not AdBMP2, increases NELL1 protein expression.

Figure 4A:
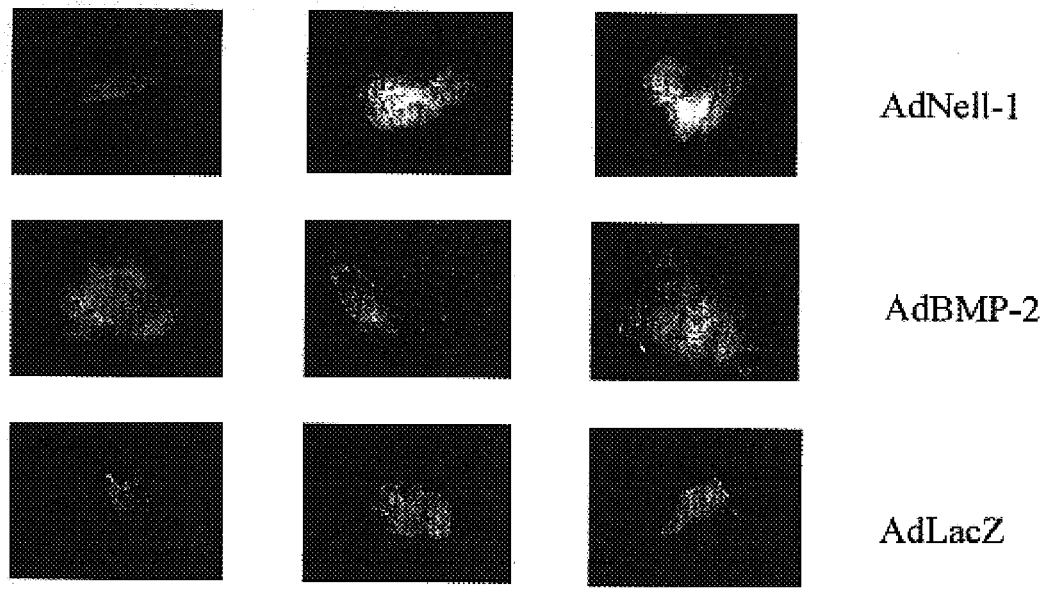
FIGS. 4A and 4B show gross appearance of AdNELL1, AdBMP2, or AdLacZ (control) transduced goat primary chondrocytes 4 weeks after implantation/injection into nude mice. NELL1 transduced samples were significantly larger than control by both inspection (FIG. 4A) and weight (FIG. 4B). In addition, NELL1 transduced samples did not demonstrate the discoloration present in the BMP2 transduced samples.
Figure 4B:
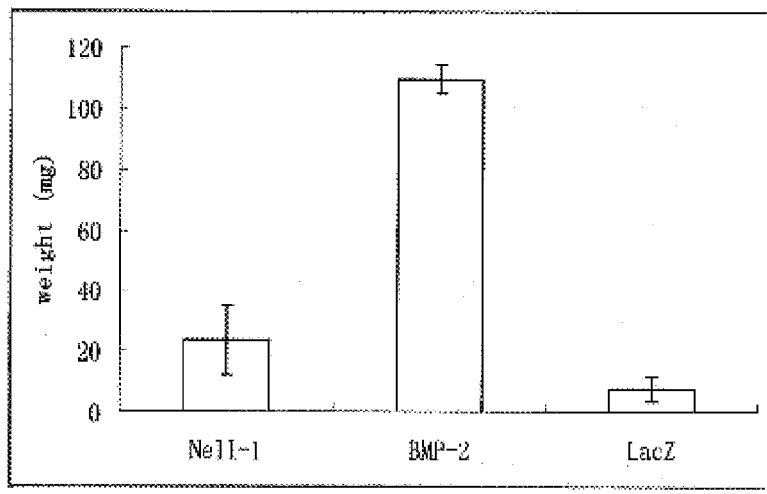

FIGS. 4A and 4B show gross appearance of AdNELL1, AdBMP2, or AdLacZ (control) transduced goat primary chondrocytes 4 weeks after implantation/injection into nude mice. NELL1 transduced samples were significantly larger than control by both inspection (FIG. 4A) and weight (FIG. 4B). In addition, NELL1 transduced samples did not demonstrate the discoloration present in the BMP2 transduced samples. These studies unexpectedly demonstrate that although BMP2 induces a larger tissue mass, the appearance of the induced mass is not consistent with a purely cartilaginous phenotype.

Figure 5A:
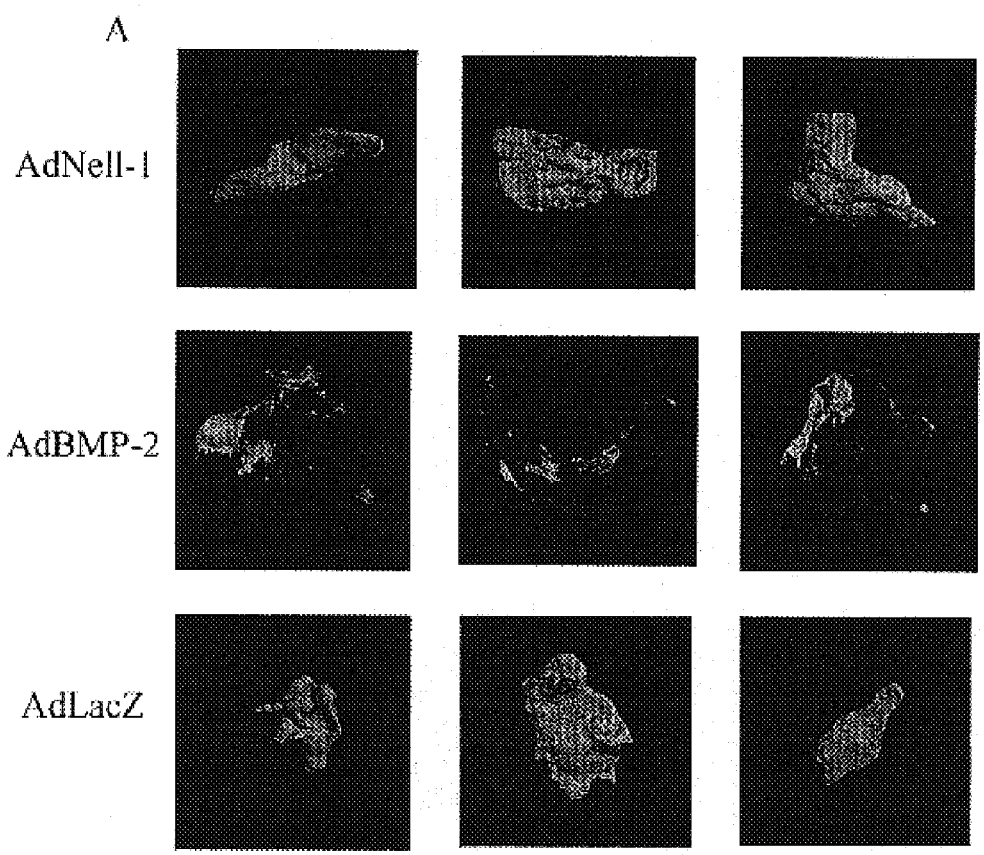
FIGS. 5A-C show micro computed tomography (CT) examination of the samples shown in FIG. 4.
Figure 5B:
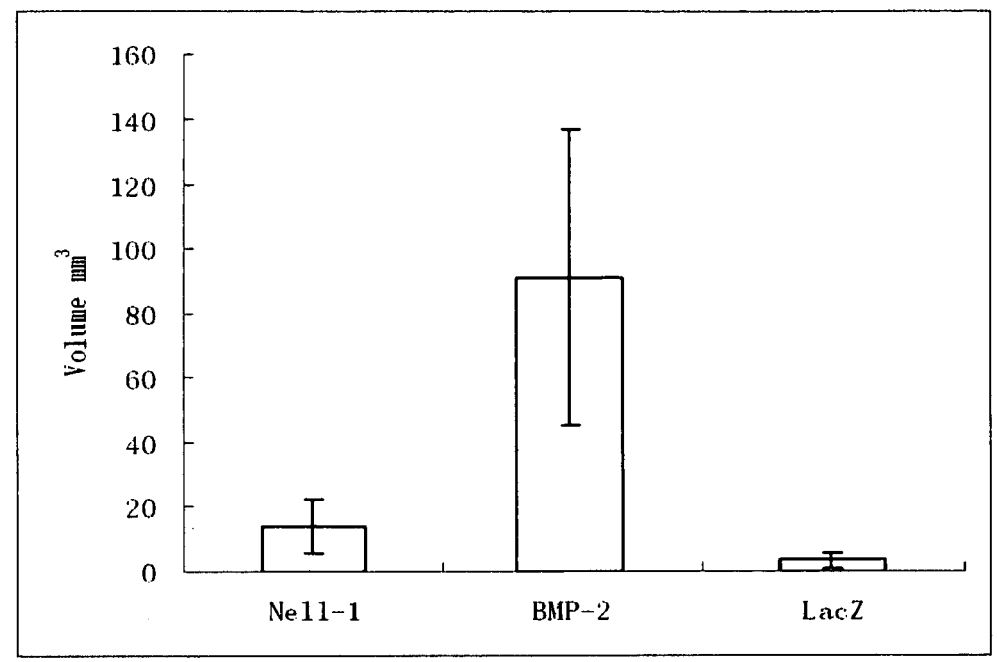
Figure 5C:
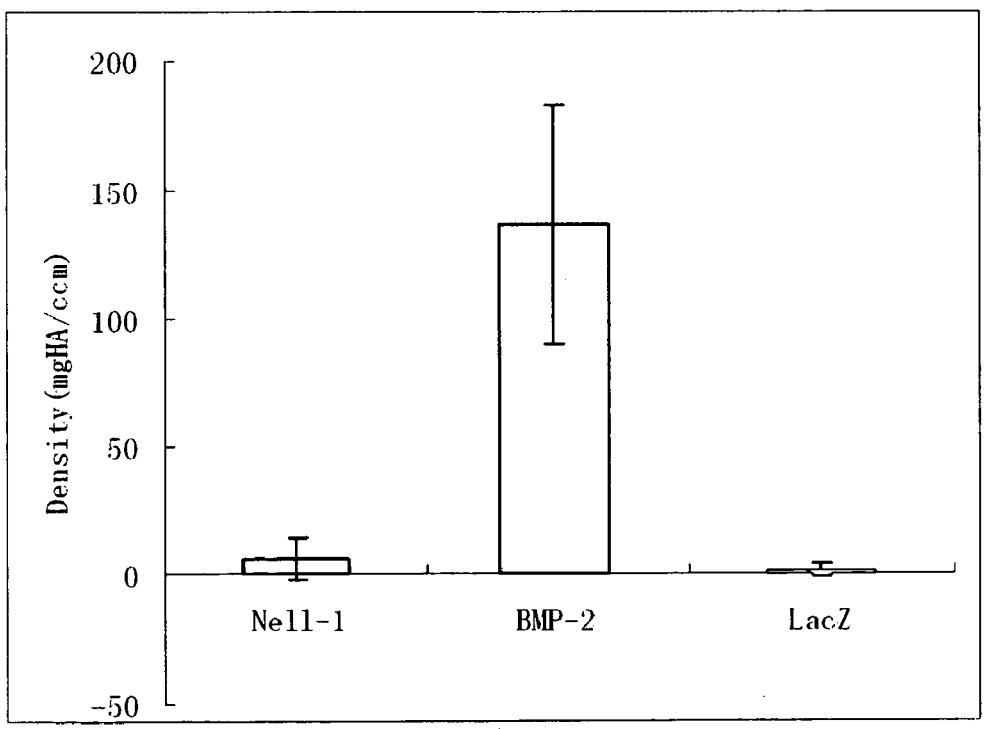

FIGS. 5A-C show micro computed tomography (CT) examination of the samples shown in FIG. 4. FIG. 5A demonstrates undesirable mineralization (red coloring) in the AdBMP2 transduced specimens but not AdNELL1 or AdLacZ specimens. FIG. 5B demonstrates that NELL1 induces significantly more cartilage mass than AdLacZ controls. FIG. 5C demonstrates that AdBMP2 significantly increased density (another indicator of mineralization) in the specimens. These studies quantitatively demonstrate that although BMP2 induces a larger tissue mass, the induced mass is largely mineralized and is not consistent with a purely cartilaginous phenotype.

Figure 6:
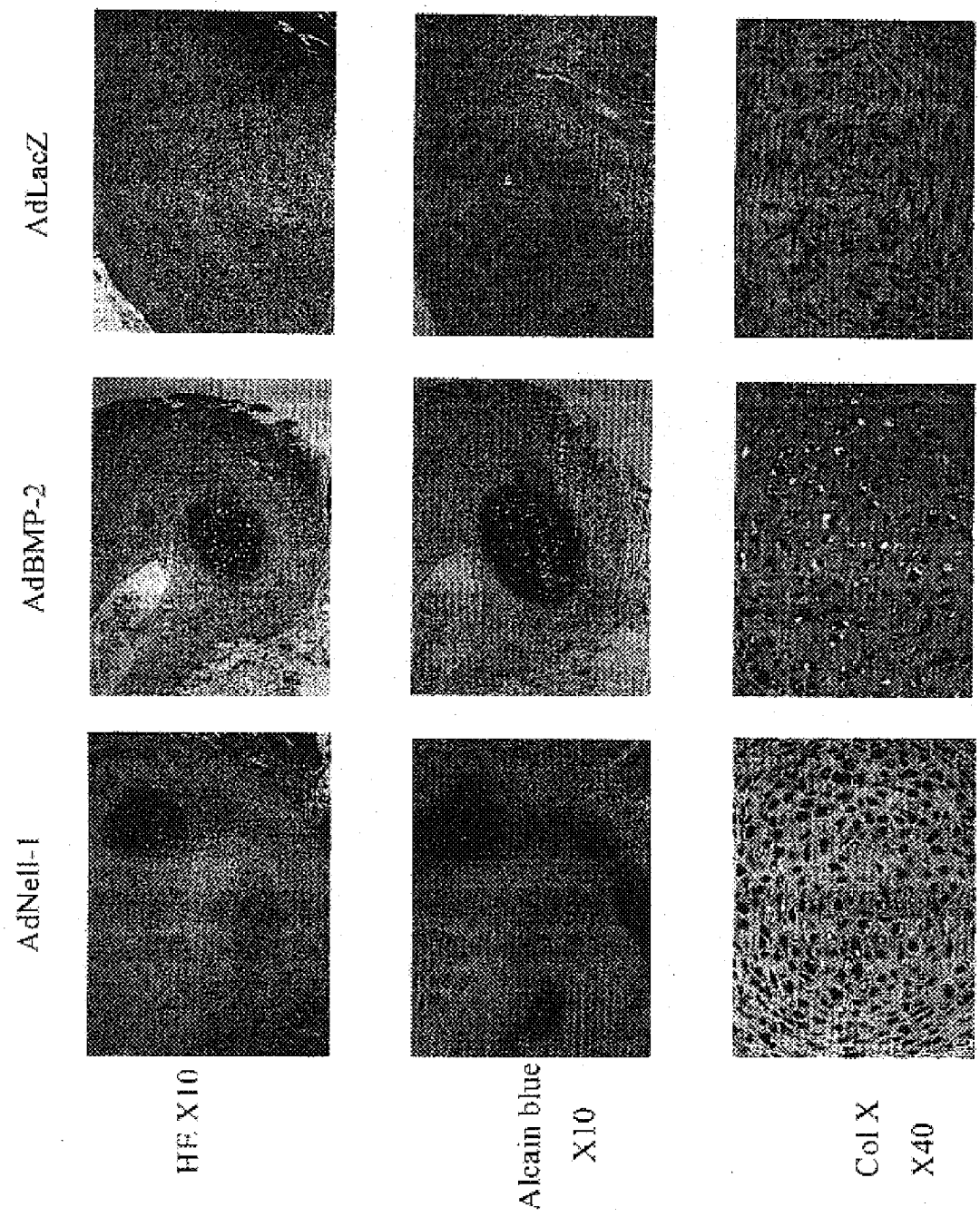
FIG. 6 shows histologic appearance of AdNELL1, AdBMP2, or AdLacZ (control) transduced goat primary chondrocytes 2 weeks after implantation/injection into nude mice. Hematoxylin and eosin (H&E) staining ($1^{st}$ row) shows evidence of increased cartilage formation in the AdNELL1 and AdBMP2 transduced specimens relative to AdLacZ controls. Alcian blue staining which stains cartilage ($2^{nd}$ row) also demonstrates increased cartilage formation in the AdNELL1 and AdBMP2 transduced specimens relative to AdLacZ controls. Type X collagen (ColX) immunostaining which stains more mature cartilage cells ($3^{rd}$ row) demonstrates increased staining in the AdNELL1 and AdBMP2 transduced specimens.

FIG. 6 shows histologic appearance of AdNELL1, AdBMP2, or AdLacZ (control) transduced goat primary chondrocytes 2 weeks after implantation/injection into nude mice. Hematoxylin and eosin (H&E) staining ($1^{st}$ row) shows evidence of increased cartilage formation in the AdNELL1 and AdBMP2 transduced specimens relative to AdLacZ controls. Alcian blue staining which stains cartilage ($2^{nd}$ row) also demonstrates increased cartilage formation in the AdNELL1 and AdBMP2 transduced specimens relative to AdLacZ controls. Type X collagen (ColX) immunostaining which stains more mature cartilage cells ($3^{rd}$ row) demonstrates increased staining in the AdNELL1 and AdBMP2 transduced specimens. Collectively, these data indicate that both AdNELL1 and AdBMP2 induce comparable cartilage formation and maturation at 2 weeks.

Figure 7:
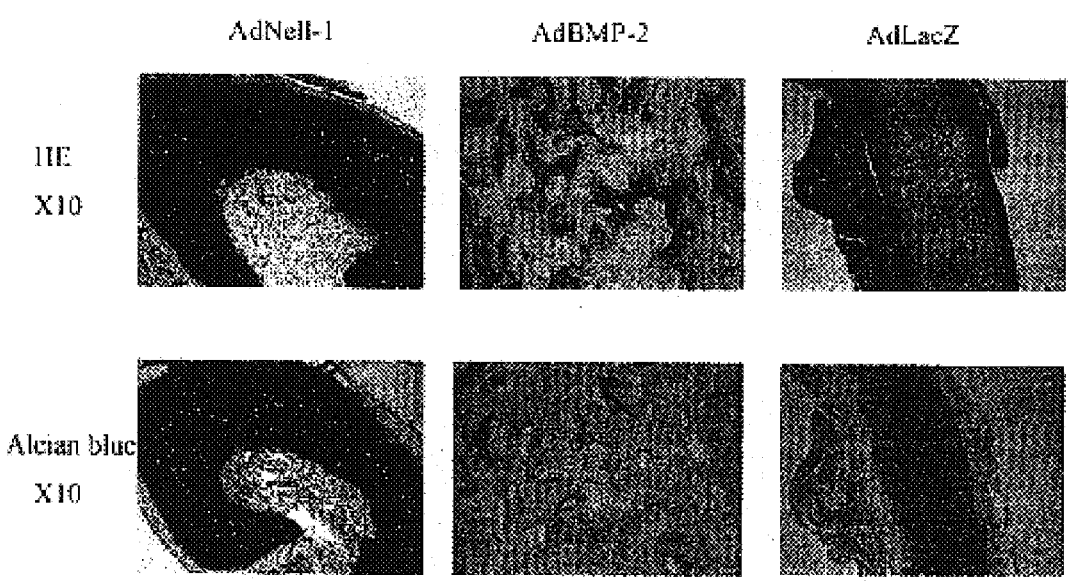
FIG. 7 shows histologic appearance of AdNELL1, AdBMP2, or AdLacZ (control) transduced goat primary chondrocytes 4 weeks after implantation/injection into nude mice. H&E staining ($1^{st}$ row) shows significant cartilage formation in the AdNELL transduced samples with no evidence of bone formation, while AdBMP2 samples show significant bone formation. A small amount of cartilage formation is seen the AdLacZ controls. Alcian blue staining ($2^{nd}$ row) also demonstrates significant cartilage formation in the AdNELL transduced samples with no evidence of bone formation, while AdBMP2 samples show significant bone formation and minimal cartilage formation. A small amount of immature cartilage formation is seen the AdLacZ controls.

FIG. 7 shows histologic appearance of AdNELL1, AdBMP2, or AdLacZ (control) transduced goat primary chondrocytes 4 weeks after implantation/injection into nude mice. H&E staining ($1^{st}$ row) shows significant cartilage formation in the AdNELL transduced samples with no evidence of bone formation, while AdBMP2 samples show significant bone formation. A small amount of cartilage formation is seen the AdLacZ controls. Alcian blue staining ($2^{nd}$ row) also demonstrates significant cartilage formation in the AdNELL transduced samples with no evidence of bone formation, while AdBMP2 samples show significant bone formation and minimal cartilage formation. A small amount of immature cartilage formation is seen the AdLacZ controls. Collectively, these data indicate that by 4 weeks, AdNELL1 can continue to induce and maintain a cartilaginous phenotype, while AdBMP2 goes on to form bone and is unable to maintain a cartilaginous phenotype in chondrogenic cells.

Figure 8:
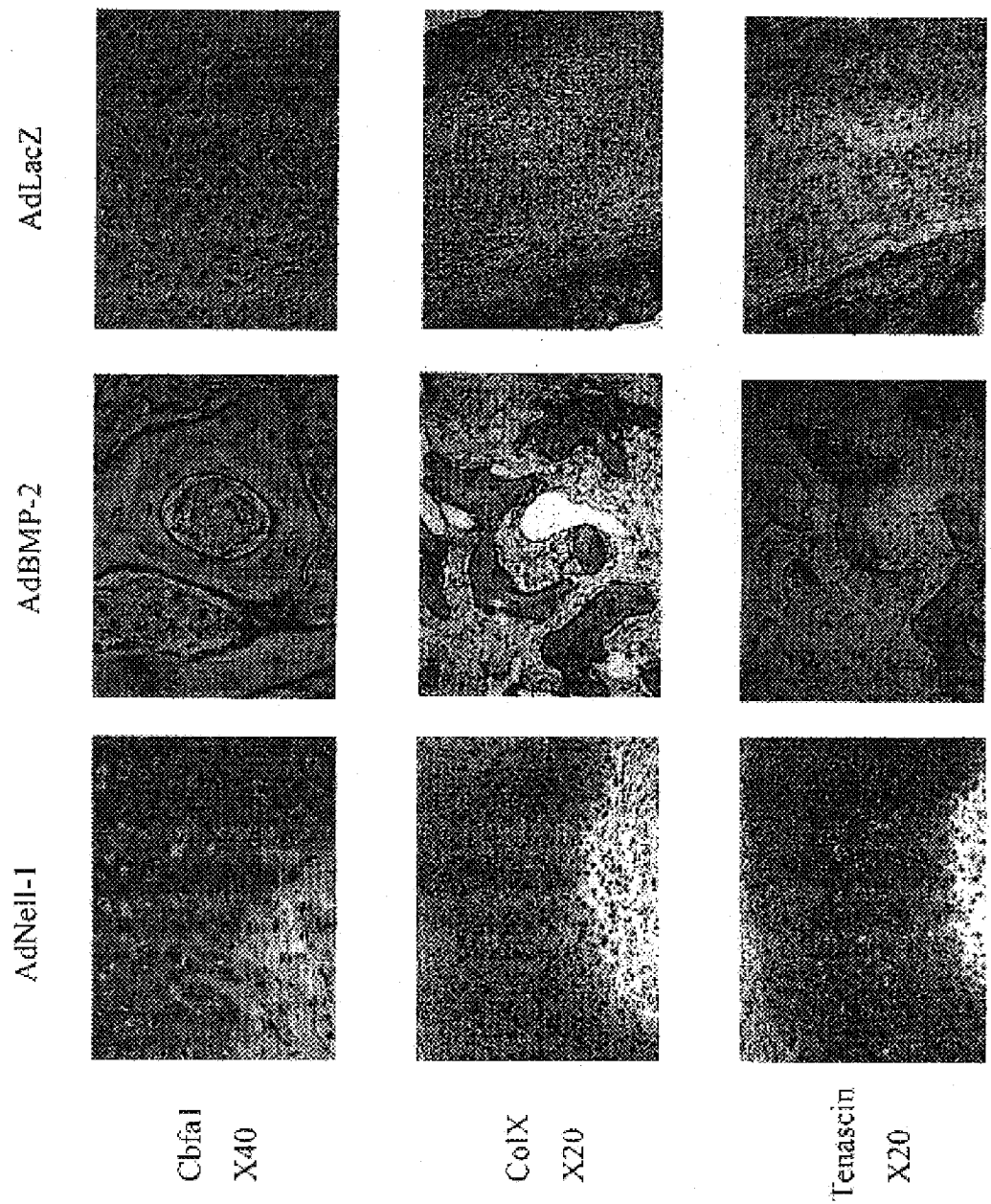
FIG. 8 shows immunostaining for bone marker Cbfa1/Runx2 and cartilage markers ColX and tenascin in AdNELL1, AdBMP2, or AdLacZ (control) transduced goat primary chondrocytes 4 weeks after implantation/injection into nude mice. Tenascin is intimately associated with the development of articular cartilage and other permanent cartilages whereas absence or reduced amounts of this matrix protein characterize transient cartilages which undergo maturation and are replaced by bone (Pacifici, M., M. Iwamoto, et al. Tenascin is associated with articular cartilage development. Dev Dyn 198(2): 123-34, 1993). Cbfa1/Runx2 is minimally expressed in cartilaginous AdNELL1 or control AdLacZ transduced samples and moderately expressed in bony AdBMP2 transduced samples ($1^{st}$ row). ColX is highly expressed and localized largely to cells in cartilaginous AdNELL1 samples without evidence of bone formation, while ColX is largely associated with the extracelluar matrix rather than cells in the AdBMP2 treated samples ($2^{nd}$ row). Tenascin is highly expressed in AdNELL1 samples and minimally present in AdBMP2 and control AdLacZ samples ($3^{rd}$ row).

FIG. 8 shows immunostaining for bone marker Cbfa1/Runx2 and cartilage markers ColX and tenascin in AdNELL1, AdBMP2, or AdLacZ (control) transduced goat primary chondrocytes 4 weeks after implantation/injection into nude mice. Tenascin is intimately associated with the development of articular cartilage and other permanent cartilages whereas absence or reduced amounts of this matrix protein characterize transient cartilages which undergo maturation and are replaced by bone (Pacifici, M., M. Iwamoto, et al. Tenascin is associated with articular cartilage development. Dev Dyn 198(2): 123-34, 1993). Cbfa1/Runx2 is minimally expressed in cartilaginous AdNELL1 or control AdLacZ transduced samples and moderately expressed in bony AdBMP2 transduced samples ($1^{st}$ row). ColX is highly expressed and localized largely to cells in cartilaginous AdNELL1 samples without evidence of bone formation, while ColX is largely associated with the extracelluar matrix rather than cells in the AdBMP2 treated samples ($2^{nd}$ row). Tenascin is highly expressed in AdNELL1 samples and minimally present in AdBMP2 and control AdLacZ samples ($3^{rd}$ row). These studies show NELL1 is able to induce molecules (e.g., tenascin) associated with development of articular cartilage and other permanent cartilages.

Figure 9:
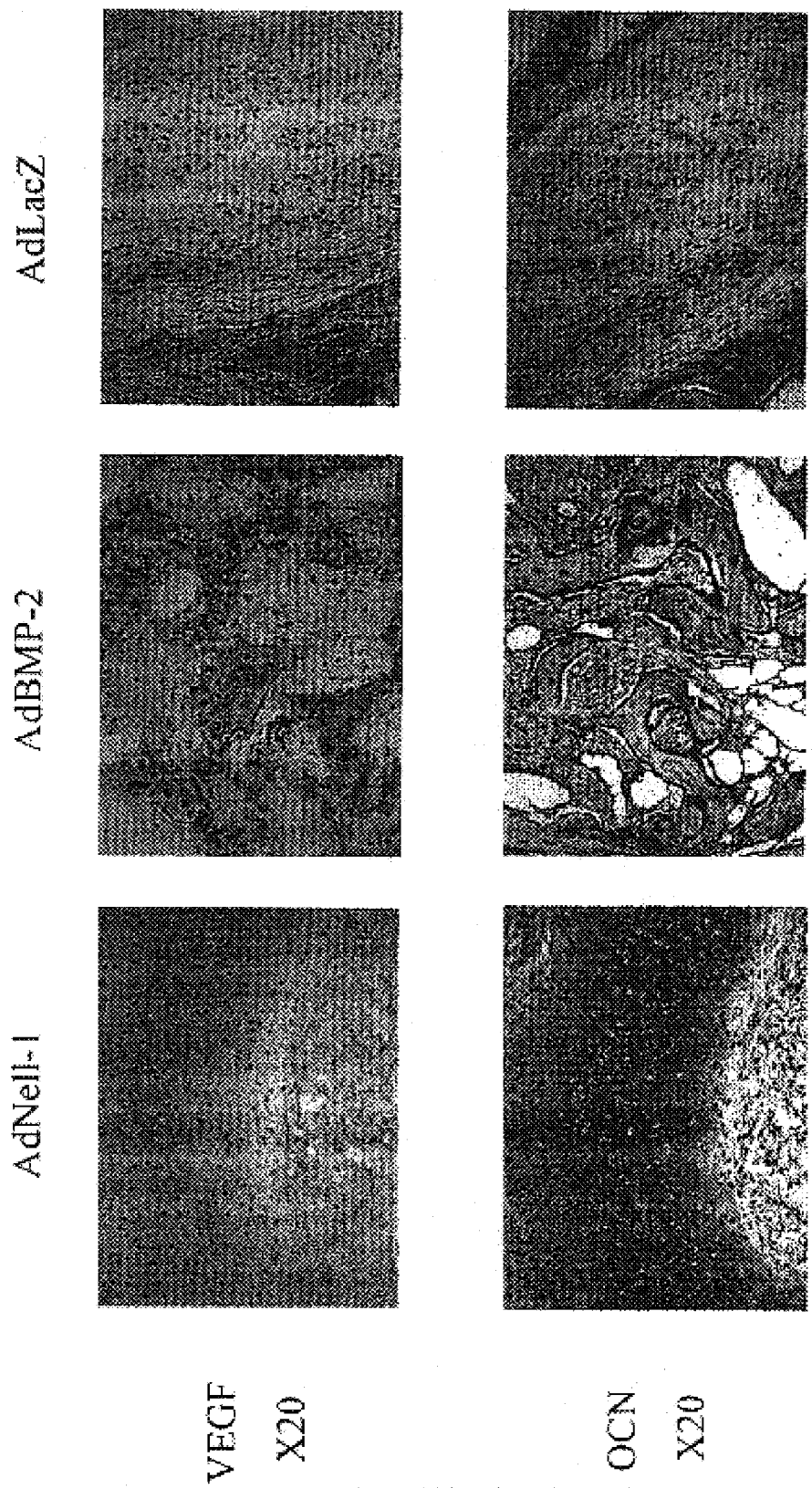
FIG. 9 shows immunostaining for endochondral ossification associated angiogenic growth factor, vascular endothelial growth factor (VEGF), and bone marker osteocalcin (OCN) in AdNELL1, AdBMP2, or AdLacZ (control) transduced goat primary chondrocytes 4 weeks after implantation/injection into nude mice. Both VEGF and OCN are not expressed in cartilaginous AdNELL1 or control AdLacZ transduced samples and moderately expressed in bony AdBMP2 transduced samples.

FIG. 9 shows immunostaining for endochondral ossification associated angiogenic growth factor, vascular endothelial growth factor (VEGF), and bone marker osteocalcin (OCN) in AdNELL1, AdBMP2, or AdLacZ (control) transduced goat primary chondrocytes 4 weeks after implantation/injection into nude mice. Both VEGF and OCN are not expressed in cartilaginous AdNELL1 or control AdLacZ transduced samples and moderately expressed in bony AdBMP2 transduced samples. These data show that NELL1 does not promote angiogenesis and that NELL1 may inhibit angiogenesis in cartilaginous samples.

Figure 10:
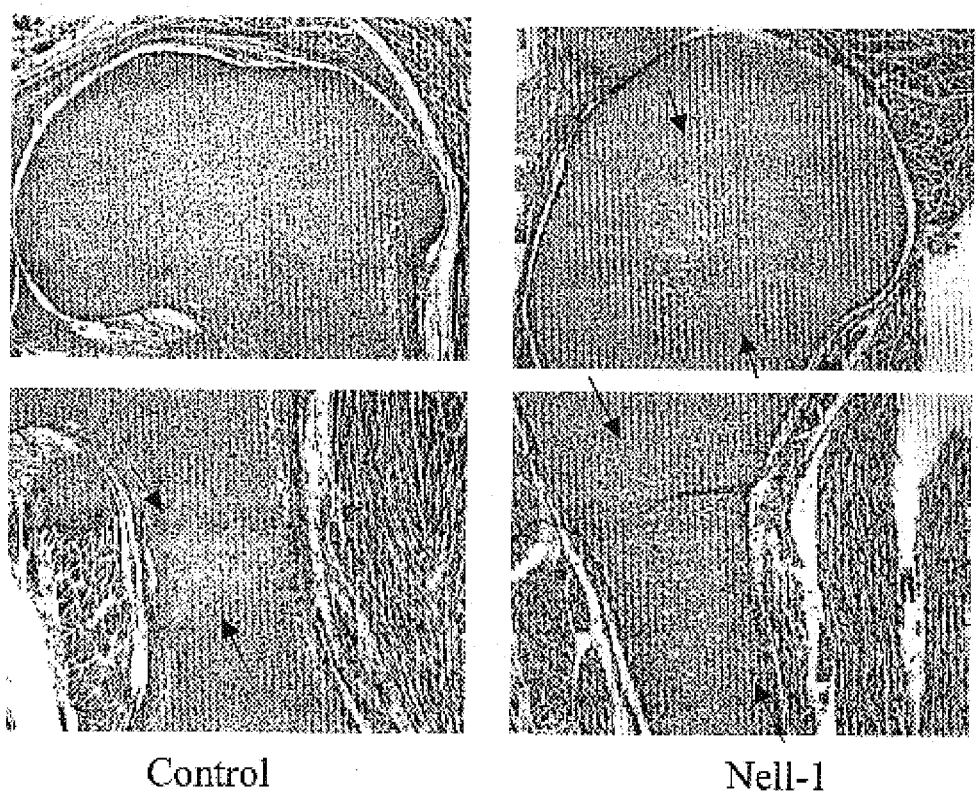
FIG. 10 shows the histology of long bone cartilage in NELL-1 over expression mice. NELL1 is expressed throughout the tibia during endochondral bone formation including both articular cartilage region (Upper panel) and also the long bone formation region (lower panel). Upper panel demonstrates that NELL1 can modulate and increase cartilage differentiation in the articular cartilage region. Accordingly, these data show that increased NELL peptide activity directly (e.g., through addition of NELL peptides or increased NELL peptide expression) or indirectly (e.g., through addition of NELL peptide enhancers and/or NELL peptide receptor agonists and/or activators) promotes cartilage formation. In the lower panel, in the long bone shaft region where bone formation originated, increased NELL1 causes cartilage formation and then hypertrophy and increased bone formation through endochondral ossification.

FIG. 10 shows the histology of long bone cartilage in NELL-1 over expression mice. NELL1 is expressed throughout the tibia during endochondral bone formation including both articular cartilage region (Upper panel) and also the long bone formation region (lower panel). Upper panel demonstrates that NELL1 can modulate and increase cartilage differentiation in the articular cartilage region. Accordingly, these data show that increased NELL peptide activity directly (e.g., through addition of NELL peptides or increased NELL peptide expression) or indirectly (e.g., through addition of NELL peptide enhancers and/or NELL peptide receptor agonists and/or activators) promotes cartilage formation. In the lower panel, in the long bone shaft region where bone formation originated, increased NELL1 causes cartilage formation and then hypertrophy and increased bone formation through endochondral ossification. Accordingly, these data show that increased NELL peptide activity directly or indirectly promotes cartilage formation, cartilage hypertrophy and endochondral ossification. The absence of NELL1 associates with less differentiated articular chondroblast/chondrocyte phenotype and less hypertrophy which is important to prevent articular cartilage replaced by bone. Accordingly, the inhibition of NELL peptide activity directly (through decreased NELL peptide expression or use of NELL peptide inhibitors) or indirectly (through NELL peptide receptor antagonists and/or inhibitors) can prevent cartilage hypertrophy and endochondral ossification and promote maintenance of a less differentiated or hypertrophied cartilage phenotype. Overall, these data are not intended to be limiting, but rather to show that NELL has broad effects on osteochondroprogenitor cell types and that the exact phenotype induced by NELL depends on a complex interplay between the amount and timing of NELL application, the exact cell type, cell differentiation state, and the microenvironment.

DEFINITIONS

The term "cartilage" is understood to encompass hyaline, elastic and fibrocartilage and can refer to any cartilaginous component of a mammal. For instance, spinal disc and knee meniscus are fibrocartilaginous structures that are included in the definition of cartilage.

The terms "polypeptide", "peptide" and "protein" can be used interchangeably herein to refer to a polymer of amino acid residues. The terms can apply to amino acid polymers in which one or more amino acid residue is an artificial chemical analogue of a corresponding naturally occurring amino acid, as well as to naturally occurring amino acid polymers.

The term "NELL" refers to "NELL1 and NELL2 peptide. A NELL1 peptide is a protein which can be expressed by the NELL1 gene or cDNA and includes SEQ ID NO: 2, 4, and 6. The NELL1 peptide can include a NELL1 peptide fragment that retains the ability to induce chondrogenic cell differentiation for cartilage formation. A NELL2 peptide is a protein which can be expressed by the NELL2 gene or cDNA and includes SEQ ID NO: 8, 10, 12 and 14. The NELL2 peptide can include NELL2 peptide fragments that retain similar activity to the full NELL2 peptide sequence. Nell-1, Nell-2, etc. intact proteins, completely or partially glycosylated, fragments, deletions, additions, amino acid substitutes, mutations and modifications that retain the biological characteristics of the naturally occurring agents. Small molecules containing Nell active domains and Nell binding sites.

In some embodiments, the term "NELL peptide" can include a fragment of a NELL1 or NELL2 related polypeptide.

In some embodiments, the term "NELL peptide" can include a NELL related agent. For example, a NELL peptide related agent can include any polypeptide with significant homology to a NELL peptide or a fragment thereof. Significant homology can be a homology of higher than about 50% homology to a NELL peptide, e.g., higher than about 60% homology to a NELL peptide, higher than about 70% homology to a NELL peptide, or higher than about 80% homology to a NELL peptide.

The NELL peptides can be natural and/or recombinant NELL peptides with a non-mutated wild-type sequence or recombinant NELL peptides with a mutated wild-type sequence that still contains significant homology to NELL peptides. In addition, NELL peptides can be derived from, but not limited to, an organism such as human cells, bacteria, yeast, or insect or plant cells. In some embodiments, the term "NELL peptide" includes structural, functional or conformational equivalents of NELL peptide. As used herein, a structural equivalent of a NELL peptide refers to a protein or peptide including a structure equivalent or substantially similar to that of a NELL peptide or of a functional domain of a NELL peptide. A functional equivalent of a NELL peptide refers to a protein or peptide having a function equivalent or substantially similar to that of a NELL peptide or of a functional domain of a NELL peptide. A conformational equivalent of a NELL peptide refers to a protein or peptide having a conformation equivalent or substantially similar to that of a NELL peptide or of a functional domain of a NELL peptide.

In some embodiments, the NELL peptide described herein can be a derivative of the NELL peptide. The term "derivative" as used herein, refers to any chemical or biological compounds or materials derived from a NELL peptide, structural equivalents thereof, or conformational equivalents thereof. For example, such a derivative can include any prodrug form, PEGylated form, or any other form of a NELL peptide that renders the NELL peptide more stable or to have a better osteo philicity or lipophilicity. In some embodiments, the derivative can be a NELL peptide attached to poly(ethylene glycol), a poly(amino acid), a hydrocarbyl short chain having C1-C20 carbons, or a biocompatible polymer. In some embodiments, the term "derivative" can include a NELL peptide mimetics. Synthesis of mimetics of a peptide is well document in the art. The following describes an example of the basic procedure for the synthesis of a peptide, including a peptide mimetics:

Before the peptide synthesis starts, the amine terminus of the amino acid (starting material) can protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free-amine is reacted with carboxyl terminus using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetics.

In some embodiments, the peptide derivative described herein includes a physically or chemically modified NELL peptide. Physically modified peptide can be modification by, for example, modification by ionic force such as forming an ionic pair with a counterion, modification by hydrogen bonding, modification by modulation of pH, modulation by solvent selection, or modification by using different protein folding/unfolding procedures, which can involve selection of folding/unfolding temperature, pH, solvent, and duration at different stage of folding/unfolding.

In some embodiments, the peptide derivative can include a chemically modified NELL peptide. For example, a short hydrocarbon group(s) (e.g. methyl or ethyl) can be selectively attached to one or multiple sites on the NELL peptide molecule to modify the chemical and/or physical properties of the peptide. In some embodiments, a mono-, oligo- or poly(ethylene glycol) (PEG) group(s) can be selectively attached to one or multiple sites on the NELL peptide molecule to modify the chemical and/or physical properties of the peptide by commonly known protein PEGylation procedures (see, e.g., Mok, H., et al., Mol. Ther., 11(1):66-79 (2005)).

The terms "NELL1 cDNA" can refer to SEQ ID NO:1, 3 and 5, and "NELL2 cDNA" can refer to SEQ ID NO:7, 9, 11 and 13.

The term "antibody" refers to any antibody that specifically binds to a NELL peptide or a related agent. The term can include various forms of modified or altered antibodies, such as an intact immunoglobulin, an Fv fragment containing only the light and heavy chain variable regions, an Fv fragment linked by a disulfide bond, a Fab or (Fab)'2 fragment containing the variable regions and parts of the constant regions, a single-chain antibody and the like. An antibody can include intact molecules as well as fragments thereof, such as, Fab and F(ab')$^{2'}$, and/or single-chain antibodies (e.g. scFv) which can bind an epitopic determinant. An antibody can be of animal (such as mouse or rat) or human origin or can be chimeric or humanized. Antibodies can be polyclonal or monoclonal antibodies ("mAb's"), such as monoclonal antibodies with specificity for a polypeptide encoded by a NELL1 or NELL2 protein.

The term "capture agent" can refer to molecules that specifically bind other molecules to form a binding complex such as antibody-antigen, lectin-carbohydrate, nucleic acid-nucleic acid, biotin-avidin, and the like.

The term "specifically binds" can refer to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody can bind to its particular "target" molecule and can not bind in a significant amount to other molecules present in the sample.

The terms "nucleic acid" or "oligonucleotide" can refer to at least two nucleotides covalently linked together. A nucleic acid of the present invention can be single-stranded or double stranded and can contain phosphodiester bonds, although in some cases, nucleic acid analogs can be included that can have alternate backbones, comprising, for example, phosphoramide, phosphorothioate, phosphorodithioate, omethylphophoroamidite linkages, and/or peptide nucleic acid backbones and linkages. Analog nucleic acids can have positive backbones and/or non-ribose backbones. Nucleic acids can also include one or more carbocyclic sugars. Modifications of the ribose-phosphate backbone can be done to facilitate the addition of additional moieties such as labels, or to increase the stability and half-life of such molecules in physiological environments, for example.

The term "specific hybridization" can refer to the binding, duplexing, or hybridizing of a nucleic acid molecule preferentially to a particular nucleotide sequence under stringent conditions, including conditions under which a probe can hybridize preferentially to its target subsequence, and can hybridize to a lesser extent to other sequences.

The term "inhibitor of NELL peptides" refers to a chemical or biological compound capable of inhibiting the activity of NELL peptides. The term also includes a chemical or biological compound capable of suppressing the expression of NELL peptides. Inhibitors of NELL peptides can interact directly or indirectly with NELL peptide transcripts or translational products. As examples, methods of interactions can include but are not limited to decreased transcription or translation of NELL peptides, decreased stability of NELL peptide transcripts or protein products, decreased activity of NELL peptide transcripts or protein products, and increased degradation of NELL peptide transcript or protein products. The term "enhancer of NELL peptides" refers to a chemical or biological compound capable of enhancing the activity of NELL peptides. The term also includes a chemical or biological compound capable of enhancing the expression of NELL peptides. As examples, methods of interactions can include but are not limited to increased transcription or translation of NELL peptides, increased stability of NELL peptide transcripts or protein products, increased activity of NELL peptide transcripts or protein products, and decreased degradation of NELL peptide transcript or protein products.

The term "modulator of NELL peptide receptors" refers to a chemical or biological compound capable of facilitating or inhibiting the binding of NELL peptide receptors to or by NELL peptides or to a chemical or biological compound capable of modulating NELL peptide receptor activity irrespective of the presence or the absence of NELL peptide. The modulator that facilitates the binding and/or activation of NELL peptide receptors to or by NELL peptides is referred to as an "agonist" of the receptor, and the modulator that inhibits the binding and/or activation of NELL peptide receptors to or by NELL peptides is referred to as an "antagonist" of the receptor. The modulator that facilitates the activation of NELL peptide receptors irrespective of NELL peptides is referred to as an "activator" of the receptor, and the modulator that inhibits activation of NELL peptide receptors irrespective of NELL peptides is referred to as an "inhibitor" of the receptor.

The term "NELL peptide," "NELL related agent," "inhibitor of NELL peptide" or "modulator of NELL peptide receptor(s)" can also be referred to as an "agent" throughout the specification.

The term "delivery vehicle" refers to any delivery vehicle used in the art of biochemistry. Some examples of common delivery vehicle are a naked DNA type vehicle, an RNA type vehicle, a virus type vehicle. Some further examples are e.g., a polymer or a peptide, sustained release carriers, synthetic scaffolds, natural scaffolds, allograft or xenograft scaffolds.

The term "mammalian subject" or "mammal" refers to any mammals, examples of which include human beings and animals such as horse.

Cartilage Formation

Cartilage formation generally proceeds via chondrification process. Chondrification is the process in which cartilage is formed from condensed mesenchyme tissue, which differentiates into chondrocytes and begins secreting the materials that form the matrix. Cartilage can undergo mineralization. Adult hyaline articular cartilage, for example, is progressively mineralized at the junction between cartilage and bone. A mineralization front advances through the base of the hyaline articular cartilage at a rate dependent on cartilage load and shear stress. Intermittent variations in the rate of advance and mineral deposition density of the mineralizing front lead to multiple tidemarks in the articular calcified cartilage.

Adult articular calcified cartilage is penetrated by vascular buds, and new bone produced in the vascular space in a process similar to endochondral ossification at the physis. A cement line demarcates articular calcified cartilage from subchondral bone. Two types of growth can occur in cartilage: appositional and interstitial. Appositional growth results in the increase of the diameter or thickness of the cartilage. The new cells derive from the perichondrium and occur on the surface of the cartilage model. Interstitial growth results in an increase of cartilage mass and occurs from within. Chondrocytes undergo mitosis within their lacuna but remain imprisoned in the matrix, which results in clusters of cells called isogenous groups.

Cartilage can also be formed via endochondral ossification. The mammalian skeleton develops through both endochondral and intramembranous bone formation processes. Embryologically, During skeletal development, the establishment of a layer of cartilage at the ends of certain bones is intimately linked to the process of endochondral ossification. The cartilaginous portion of endochondral bone formation involves chondroblast/chondrocyte differentiation, maturation, hypertrophy with or without mineralization depending on the location of the cartilage. Non-mineralizing cartilage formation includes but is not limited to formation of articular cartilage, temporomandibular joint, wrist, knee, and intervertebral disc fibrocartilages.

Endochondral ossification or long bone formation is related to bone formation, which permits functional stresses to be sustained during skeletal growth and is well demonstrated in the development of the long bones. In this process, a small model of the long bone is first formed in solid hyaline cartilage which undergoes mainly appositional growth to form an elongated, dumb-bell shaped mass of cartilage consisting of a shaft (diaphysis) and future articular portions (epiphysis) surrounded by perichondrium (see, e.g., Wheater, P. R. and H. G. Burkitt (1987). *Functional histology: a text and colour atlas.* Edinburgh; New York, Churchill Livingstone; Beaupre, G. S., S. S. Stevens, et al., *J Rehabil Res Dev* 37(2): 145-51) (2000)).

Within the shaft of the cartilage model then chondrocytes enlarge greatly, resorbing the surrounding cartilage so as to leave only slender perforated trabeculae of cartilage, matrix. This cartilage matrix then calcifies and the chondrocytes degenerate leaving large, interconnecting spaces. During this period the perichondrium of the shaft develops chondrogenic potential and assumes the role of periosteum. The periosteum then lays down a thin layer of bone around the surface of the shaft and primitive mesenchymal cells and blood vessels invade the spaces left within the shaft after degeneration of the chondrocytes. The primitive mesenchymal cells differentiate into osteoblasts and blood-forming cells on the surface of the calcified remnants of the cartilage matrix and commence the formation of irregular, woven bone (Wheater and Burkitt, 1987, supra). In the cartilage model described in Wheater and Burkitt, 1987, supra, the ends of the original cartilage model have then become separated by a large site of primary ossification in the shaft. The cartilaginous ends of the model, however, continue to grow in diameter. Meanwhile, the cartilage at the ends of the shaft continues to undergo regressive changes followed by ossification so that the developing bone now consists of an elongated, bony diaphyseal shaft with a semilunar cartilage epiphysis at each end. The interface between the shaft and each epiphysis constitutes a growth or epiphyseal plate. Within the growth plate, the cartilage proliferates continuously, resulting in progressive elongation of the bone. At the diaphyseal aspect of each growth plate, the chondrocytes mature and then die, the degenerating zone of cartilage being replaced by bone. Thus the bony diaphysis lengthens and the growth plates are pushed further and further apart. On reaching maturity, hormonal changes inhibit further cartilage proliferation and the growth plates are replaced by bone causing fusion of the diaphysis and epiphysis (Wheater and Burkitt, 1987, supra). In the meantime, in the center of the mass of cartilage of each developing epiphysis, regressive changes and bone formation similar to that in the diaphyseal cartilage occur along with appositional growth of cartilage over the whole external surface of the epiphysis. This conversion of central epiphyseal cartilage to bone is known as secondary ossification. A thin zone of hyaline cartilage always remains at the surface as the articular cartilage (Wheater and Burkitt, 1987, supra).

Thus, endochondral bone formation and growth is achieved in part by the proliferation and maturation of cartilage cells (chondroblasts, chondrocytes) with or without cartilage cell mineralization. Cartilage formation or regeneration can be achieved by controlling cartilage cell mineralization. Without being bound by a particular theory, cartilage cell mineralization can be controlled by controlling factors such as: a) location, b) cell type, c) cell differentiation state, d) microenvironment, and e) biomechanical forces. For example, the mineralization of a cartilage cell can be controlled by placing the cartilage cell near an epiphyseal growth plate in which mineralization generally occurs or near an articular surface in which mineralization generally does not occur. It is known in the art that chondrocyte hypertrophy and up-regulated matrix calcification are dissociable states (see, e.g., Johnson, van Etten et al. 2003) (see, e.g., Johnson, K. A., D., et al., J Biol Chem 278(21):18824-32 (2003)). For example, the formation of endochondral bone can be evaluated by chondroblast hypertrophy as viewed by an increase in hypertrophic and apoptotic chondroblasts, elucidated by TUNEL staining. In another example, the formation of cartilage can be evaluated also by chondroblast hypertrophy without necessarily apoptosis or mineralization.

Cartilage Regeneration

Cartilage contains a significant amount of water. For instance, articular cartilage is comprised of mostly water (60-80 wt %) and the remaining ECM comprises mostly type II collagen (50-90% dry mass) and proteoglycans (5-10%). Other collagens and minor ECM molecules have been identified in small quantities. It is organization of the ECM into distinct zones, and the interaction between water and the ECM in the various zones that provide the toughness that is required for the absorption and transmission of biomechanical forces across joints, and simultaneously the frictionless articulating surfaces that are needed for joint motion. Stresses as high as 4 and 20 MPa have been reported in human hip joints during routine walking and jumping, respectively! As amazing as the articular cartilage is, it exhibits unfortunately minimal capacity for repair. Over 20 million Americans suffer from osteoarthritis and degenerative joint diseases with an associated annual healthcare burden of over $60 billion. A wide array of scaffolds, cytokines, and growth factors have been investigated for cartilage tissue engineering (see, e.g., Frenkel, S. R., et al., Ann. Biomed. Eng. 32:26-34 (2004); Tuli, R., et al., Arthritis Res. Ther. 5:235-238 (2003); and Ashammakhi, N. and Reis, R L. Topics in Tissue Engineering, Vol. 2, 2005). The role of static vs. dynamic compression, shear stress, hydrostatic pressure, fluid flow, electrical streaming potentials, bioreactors, and complex loading on chondrocyte biological response and tissue remodeling have been investigated extensively and the mechanotransduction pathways reviewed Ashammakhi, N. and Reis, R L. Topics in Tissue Engineering, Vol. 2, 2005) (see FIGS. 7A-D therein)

Accordingly, in a further aspect of the present invention, the composition provided herein includes at least a NELL peptide or an agonist of the receptor of NELL peptides in an amount effective for inducing chondroblast and chondrocyte to form cartilage. NELL proteins, peptides, DNA, RNA, and NELL agonists, and antagonist inhibitors can be used alone or in conjunction with scaffolds with and without cells, with or without mechanical stimulation, in the presence or absence of additional growth factors. For example, in one embodiment, the composition can be effective in regenerating or repairing or augmenting cartilage in intervertebral disc, temporomandibular disc, knee and wrist fibrocartilage, and articular surfaces. In another embodiment, the composition can be effective in forming cartilage via ex vivo gene therapy and protein application to cells with or without scaffold in tissue engineering.

Depending on the delivery method and the local environment, a composition including a NELL peptide (e.g., a NELL1 peptide) can be used to induce an chondrogenic cell, as such as a chondrocyte or chondroblast, to differentiate and form cartilage only. For example, in an articular cartilage defect, the composition described herein can induce an chondrogenic cell such as chondrocyte/blast to form cartilage only. The composition can be applied to the defected cartilage area as a scaffold/carrier. In some embodiments, the composition can optionally include cells (stem cells, chondroblast etc). In some embodiments, the composition can be applied as gene therapy.

In some embodiments, as used herein, the cells can be, e.g., differentiated chondrocytes; differentiated cells (e.g. skeletal muscle cells, fibroblasts) that are de-differentiated after implantation, or prior to implantation; adult stem cells that are differentiated after implantation, or prior to implantation; embryonic stem cells that are differentiated after implantation, or prior to implantation; human; modified by nucleic acid, protein, small molecules, siRNA, antibodies.

In some yet embodiments, the composition can be used in cartilage tissue engineering. For example, when chondroblasts are cultured on an "oscillating", intermittent stress tension environment, NELL1 peptide can include the chondroblast cells to differentiate and form cartilage. In these embodiments, the duration of application of the oscillating stress also plays an important role. For example, if the oscillating force is applied continuously, the composition having a NELL1 peptide can induce endochondral bone formation. Therefore, in the application of the oscillating stress shall be intermittently such that the differentiation of an chondrogenic cell (e.g., chondrocyte/blast) can stop at the cartilage stage and thus prevent the cell from differentiating into endochondral bone formation.

Therefore, in some embodiments, the composition described herein can be used to regenerate/repair cartilage, e.g., for disc repair in articular cartilage and intervertebral disc.

Other exemplary cartilage conditions that can be treated, prevented, or ameliorated by a composition disclosed herein include, but are not limited to, chondrocalcinosis, osteoarthritis, and/or other diseases characterized by pathological cartilage degeneration.

In one embodiment, a method of increasing endochondral bone formation can include increasing the concentration of a NELL1 gene product in a region where bone formation is desired; optionally applying a second agent to the region where bone formation is desired and at least inducing hypertrophy of chondroblast in the region where bone formation is desired.

The method can include increasing the concentration of a NELL1 gene product by applying a NELL1 peptide to the location where bone formation is desired, and the NELL1 peptide can be selected from the group comprising: SEQ ID NO:2, SEQ ID NO: 4, or SEQ ID NO:6, or any portion of the NELL peptide which is effective in increasing endochondral bone formation, which involves both cartilage and bone.

The second agent can include, but is not limited to TGF-beta, BMP2, BMP4, BMP7, bFGF, insulin like growth factor (IGF), Sox9, collagen, chondrogenic cells, bone, bone matrix, tendon matrix, ligament matrix. The second agent can be selected to have a complimentary or synergistic effect with NELL1 in inducing endochondral bone formation. Other agents are described below.

Inhibition of Angiogenesis and Cartilage Formation/Regeneration

As specified in Shukunami et al., cartilage forms a template for most of the bony skeleton in embryonic development (Shukunami, C., Y. Oshima, et al., Biochem Biophys Res Commun 333(2): 299-307) (2005)). Cartilage is not directly converted to bone but is gradually replaced through the actions of osteoclasts and osteoblasts, which are brought to the ossification center of cartilage with vascular invasion (endochondral bone formation). Thus, the vascular invasion of cartilage can be crucial for bone formation at an appropriate stage of development. Cartilage acquires an anti-angiogenic nature upon chondrogenesis and quickly loses it, as chondrocytes mature to become hypertrophic and calcified prior to vascular invasion, suggesting that cartilage undergoes a dynamic switching of the anti-angiogenic phenotype. Undoubtedly pro-angiogenic factors act as a driving force for vascular invasion into tissues. VEGF-A is a key regulator of angiogenesis during endochondral bone formation: VEGF-A is expressed in hypertrophic cartilage, but not in resting or proliferating cartilage.

Matrix metalloproteinases (MMPs) can influence bone development, which involves matrix-remodeling during vascular invasion (e.g., MMP-9, MMP-13, MMP-14). In mice lacking MMP-9, vascular invasion and subsequent ossification were delayed, causing progressive lengthening of the growth plate. The delay in ossification appeared to be secondary to a diminished vascular invasion of cartilage probably because MMP-9-deficient hypertrophic cartilage fails to release normal levels of pro-angiogenic activity to stimulate vessel formation and to recruit osteo/chondroclasts. Targeted inactivation of MMP-14 (membrane type 1 MMP: MT1-MMP) causes severe defects in both endochondral and intramembranous bone formation in mice. These results indicate that MMPs play a regulatory role in angiogenic switching of the cartilage phenotype. Thus, an important part of cartilage formation and regeneration can involve differential regulation of pro-angiogenic factors such as MMP-9, MMP-13, MMP-14, and VEGF and anti-angiogenic factors such as chondromodulin-I (ChM-I), thrombospondin (TSP)-1, TSP-2, tissue inhibitor of metalloproteinase (TIMP)-2, TIMP-3. Specifically, pro-angiogenic factors can be relatively more prominent in areas of cartilage undergoing ossification, and anti-angiogenic factors may be relatively more prominent in areas of cartilage not undergoing ossification. These results also indicate that the transcription factor Cbfa1/Runx2 can be involved in the control of angiogenic switching in cartilage: Cbfa1/Runx2 null mice are defective in hypertrophic cartilage differentiation, vascular invasion of cartilage rudiments, and VEGF expression, and exhibit a sustained expression of the ChM-I gene. In Cbfa1/Runx2 null mice expressing the Cbfa1/Runx2 transgene in non hypertrophic chondrocytes, vascular invasion, and cartilage remodeling was restored with the upregulation of VEGF and concomitant downregulation of ChM-I gene expression.

Without being bound by a particular theory, NELL1 can have a role in the angiogenic switching in cartilage, since NELL1 is a direct downstream effector of Cbfa1/Runx2 effects. In addition without being bound by a particular theory, NELL1's role in cartilage formation can also relate to potential anti-angiogenic effects of NELL1——as NELL1 also contains a $NH_2$-terminal thrombospondin-like module.

Other Agents

In one embodiment, the composition for cartilage formation and regeneration described herein can include one or more other agents. Such agents can be chondroprotective agents, anti-pain and/or anti-inflammatory agents, growth factors, anti-angiogenic agents, or combinations thereof.

The chondroprotective agents can be, for example, (1) antagonists of receptors for the interleukin-1 family of proteins, including, for example, IL-1.beta., IL-17 and IL-18; (2) antagonists of the tumor necrosis factor (TNF) receptor family, including, for example, TNF-R1; (3) agonists for interleukin 4, 10 and 13 receptors; (4) agonists for the TGF-.beta. receptor superfamily, including, for example, BMP-2, BMP-4 and BMP-7; (5) inhibitors of COX-2; (6) inhibitors of the MAP kinase family, including, for example, p38 MAP kinase; (7) inhibitors of the matrix metalloproteinases (MMP) family of proteins, including, for example, MMP-3 and MMP-9; (8) inhibitors of the NF-.kappa.B family of proteins, including, for example, the p50/p65 dimer complex with I.kappa.B; (9) inhibitors of the nitric oxide synthase (NOS) family, including, for example, iNOS; (10) agonists and antagonists of integrin receptors, including, for example, agonists of $\alpha_v\beta_3$ integrin; (11) inhibitors of the protein kinase C (PKC) family; (12) inhibitors of the protein tyrosine kinase family, including, for example, the src subfamily; (13) modulators of protein tyrosine phosphatases; and (14) inhibitors of protein src homology 2 (SH2) domains. Additional chondroprotective agents include other growth factors, such as by way of example insulin-like growth factors (e.g., IGF-1) and fibroblast growth factors (e.g., bFGF). Other chondroprotective agents are described in U.S. Pat. No. 7,067,144, the teachings of which are incorporated herein by reference. These chondroprotective agents can be used alone or in combination along with a NELL peptide or related agent. In some embodiments, the composition described herein can specifically exclude any of the above described chondroprotective agents.

The anti-pain and/or anti-inflammatory agents can be, e.g., (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin.sub.1 and neurokinin.sub.2 receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA.sub.2 isoform inhibitors and PLC isoform inhibitors, (b) cyclooxygenase inhibitors, and (c) lipooxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B.sub.4 receptor subtype antagonists and leukotriene D.sub.4 receptor subtype antagonists; (12) opioid receptor agonists, including μ-opioid, δ-opioid, and .kappa.-opioid receptor subtype agonists; (13) purinoceptor antagonists including $P_2X$ receptor antagonists and $P_2Y$ receptor antagonists; and (14) calcium channel antagonists. Each of the above agents functions either as an anti-inflammatory agent and/or as an anti-nociceptive (i.e., anti-pain or analgesic) agent. The selection of agents from these classes of compounds is tailored for the particular application. These anti-pain and/or anti-inflammatory agents can be used alone or in combination along with a NELL peptide or related agent. In some embodiments, the composition described herein can specifically exclude any of the above described anti-pain and/or anti-inflammatory agents.

The growth factors can be, e.g., FGF-2, FGF-5, IGF-1, TGF-.beta., BMP-2, BMP-7, PDGF, VEGF, OP1, OP2, OP3, BMP2, BMP3, BMP4, BMP5, BMP6, BMP9, BMP10, BMP11, BMP12, BNP15, BMP16, DPP, Vgl, 60A protein, GDF-1, GDF3, GDF5, GDF6, GDF7, GDF8, GDF9, GDF10 and GDF11. Some other growth factors are described in U.S. Pat. Nos. 7,067,123, and 7,041,641, the teachings of which are incorporated herein by reference. These growth factors can be used alone or in combination along with a NELL peptide or related agent. In some embodiments, the composition described herein can specifically exclude any of the above described growth factors.

The anti-angiogenic agents can be, e.g., anti-angiogenic factors, including for example Anti-Invasive Factor, retinoic acids and their derivatives, paclitaxel including analogues and derivatives thereof, Suramin, Tissue Inhibitor of Metalloproteinase-1, Tissue Inhibitor of Metalloproteinase-2, Plasminogen Activator Inhibitor-1 and Plasminogen Activator Inhibitor-2, and lighter "d group" transition metals. Similarly, a wide variety of polymeric carriers may be utilized, representative examples of which include poly(ethylene-vinyl acetate) (40% cross-linked), poly(D,L-lactic acid) oligomers and polymers, poly(L-lactic acid) oligomers and polymers, poly(glycolic acid), copolymers of lactic acid and glycolic acid, poly(caprolactone), poly(valerolactone), poly(anhydrides), copolymers of poly(caprolactone) or poly(lactic acid) with polyethylene glycol, and blends thereof. Within certain preferred embodiments, the compositions comprise a compound which disrupts microtubule function, such as, for example, paclitaxel, estramustine, colchicine, methotrexate, curacin-A, epothilone, vinblastine or tBCEV. Within other preferred embodiments, the compositions comprise a polymeric carrier and a lighter d group transition metal (e.g., a vanadium species, molybdenum species, tungsten species, titanium species, niobium species or tantalum species) which inhibits the formation of new blood vessels (as specified in USP 20060240113), inhibitors of VEGF (as specified in USP 20060241084), other inhibitors of angiogenesis (as specified in USP 20060235034, 7,122,635), chondromodulin-I or tenomodulin (Shukunami, et al., 2005, supra), or other endogenous or exogenous anti-angiogenic factors well known to those in the art.

Formulations

The composition described herein can be formulated into any desired formulation. The composition can include materials and carriers to effect a desired formulation. For example, the composition can include an injectable or moldable material that can set within a pre-defined period of placement. Such a pre-defined period can be, e.g., 10 minutes, 30 minutes, one hour, two hours, etc.

In some embodiments, the composition can include a chemical gel that includes primary bonds formed due to changes in pH, ionic environment, and solvent concentration. Examples of such chemical gels can be, but are not limited to, polysaccharides such as chitosan, chitosan plus ionic salts such as beta-glycerophosphates, aginates plus Ba2+, Sr2+, Ca2+, Mg2+, collagen, fibrin, plasma or combinations thereof.

In some embodiments, the composition can include a physical gel that include secondary bonds formed due to temperature changes. Examples of such physical gels can be, but are not limited to, alginate, poly(ethylene glycol)-poly (lactic acid-co-glycolic acid)-poly(ethylene glycol) (PEG-PLGA-PEG) tri-block copolymers, agarose, and celluloses. In some embodiments, physical gels that can be used in the composition described herein can include physical gels that are liquid under high shear but gels to solid at low shear. Examples of such physical gels include, but are not limited to, hyaluronic acid, or polyethylene oxides. The physical gels can have pre-formed materials with pre-defined dimensions and shape.

In some embodiments, the composition described herein can include a material that degrade or release active agents in response to a stimulus. Some examples of such stimuli are mechanical stimuli, light, temperature changes, pH changes, change of ionic strength, or electromagnetic field. Such materials are know in the art some examples of such materials are chitosan, alginates, pluronics, methyl cellulose, hyaluronic acids, and polyethylene oxides. Other examples are described by Brandl F, Sommer F, Goepferich A. "Rational design of hydrogels for tissue engineering: Impact of physical factors on cell behavior" in Biomaterials. Epub Sep. 29, 2006.

In some embodiments, the composition described herein can include a gel containing any of hydroxyapatites, apatites, tricalcium phostphates, calcium phosphates, bioactive glass, human allograft bone and cartilage, bovine bone and cartilage, or their mixtures thereof.

In some embodiments, the composition described herein including any of the gels described above can further include a crosslinker to further tailor degradation kinetics and controlled release. Alternatively, in some embodiments, the composition described herein can include an interpenetrating phase composite or interpenetrating network (IPN) that includes any of the above described gels. Some examples of the crosslinker includes, but are not limited to, common crosslinking agents (polyalkylene oxide, ethylene dimethacrylate, N,N'-methylenebisacrylamide, methylenebis(4-phenyl isocyanate), ethylene dimethacrylate, divinylbenzene,allyl methacrylate, carbodiimidazole, sulfonyl chloride, chlorocarbonates, n-hydroxysuccinimide ester, succinimidyl ester, epoxides, aryl halides, sulfasuccinimidyl esters, and maleimides); PEG based crosslinkers (e.g. MAL-dPEGx-NHS-esters, MAL-dPEGx acid, Bis-MAL-dPEGx, etc.) and photo/light activated crosslinkers, N-hydroxysuccinimide-based crosslinkers, dilysine, trilysine, and tetralysine.

The composition described herein can include a carrier. The carrier can be a polymeric carrier or non-polymeric carrier. In some embodiments, the carrier can be biodegradable, such as degradable by enzymatic or hydrolytic mechanisms. Examples of carriers include, but are not limited to synthetic absorbable polymers such as such as but not limited to poly (α-hydroxy acids) such as poly(L-lactide) (PLLA), poly(D, L-lactide) (PDLLA), polyglycolide (PGA), poly(lactide-co-glycolide) (PLGA), poly(-caprolactone), poly(trimethylene carbonate), poly(p-dioxanone), poly(-caprolactone-co-glycolide), poly (glycolide-co-trimethylene carbonate) poly(D, L-lactide-co-trimethylene carbonate), polyarylates, polyhydroxybutyrate (PHB), polyanhydrides, poly(anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly(glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. No. WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier can further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65 degrees C. See, for example, U.S. Pat. Nos. 6,426,114 and 6,013,591; and PCT Int. Appl. WO/9117965 herein incorporated by reference.

Other examples of carriers include, collagen (e.g. Collastat, Helistat collagen sponges), hyaluronan, fibrin, chitosan, alginate, and gelatin. See for example, PCT Int. Appls. WO/9505846; WO/02085422, herein incorporated by reference.

In one embodiment, the carrier can include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278(44), p. 43229-43235, herein incorporated by reference.

In one embodiment, the composition can be in the form of a liquid, solid or gel. In one embodiment, the substrate can include a carrier that is in the form of a flowable gel. The gel can be selected so as to be injectable, such as via a syringe at the site where cartilage formation is desired. The gel can be a chemical gel which can be a chemical gel formed by primary bonds, and controlled by pH, ionic groups, and/or solvent concentration. The gel can also be a physical gel which can be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier can be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the substrate can include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate. PCT Int. Appl. WO/2001070288; U.S. Pat. No. 5,124,151 herein incorporated by reference. In one embodiment, where the carrier can have a surface that is decorated and/or immobilized with cell adhesion molecules, adhesion peptides, and adhesion peptide analogs which can promote cell-matrix attachment via receptor mediated mechanisms, and/or molecular moieties which can promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, herein incorporated by reference.

In one embodiment, the carrier can include various naturally occurring matrices or their components such as devitalized cartilage matrix, demineralized bone matrix, or other components derived from allograft, xenograft, or any other naturally occurring material derived from Monera, Protista, Fungi, Plantae, or Animalia kingdoms.

In one embodiment, the carrier can include comprised of sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier can include surfactants to promote NELL1 stability and/or distribution within the carrier materials such as, but not limited to polyoxyester (e.g. polysorbate 80, polysorbate 20 or Pluronic F-68).

In one embodiment, the carrier can include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier can include a combination of materials such as those listed above. By way of example, the carrier can a be PLGA/collagen carrier membrane. The membrane can be soaked in a solution including NELL1 peptide.

In one embodiment, an implant for use in the human body can include a substrate including NELL1 in an amount sufficient to induce cartilage formation or repair proximate to the implant.

In one embodiment, an implant for use in the human body can include a substrate having a surface including NELL1 in an amount sufficient to induce cartilage formation or repair proximate to the implant.

In one embodiment, an implant for use in the human body can include a substrate having a surface including chondrogenic cells, and NELL1 in an amount sufficient to induce cartilage formation or repair. In one embodiment, the implant can be seeded with cells, including but not limited to autologous cells, chondrogenic or osteoblastic cells, cells expressing NELL1 or another chondrogenic molecule.

An implant can include a substrate formed into the shape of a mesh, pin, screw, plate, or prosthetic joint. By way of example, a substrate can be in a form of a dental or orthopedic implant, and NELL1 can be used to enhance integration in bone in proximity to the implant. An implant can include a substrate that is resorbable, such as a substrate including collagen.

The NELL1 peptide can be combined with a acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable can include powder, or injectable or moldable pastes or suspension.

The compositions of this invention can comprise a solution of the NELL1 peptide dissolved in a pharmaceutically acceptable carrier, such as an aqueous carrier for water-soluble peptides. A variety of carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL1 peptide in these formulations can vary widely, and will be selected primarily based on fluid volumes, viscosities, body weight and the like in accordance with the particular mode of administration selected and the patient's needs.

The dosage regimen will be determined by the clinical indication being addressed, as well as by various patient variables (e.g. weight, age, sex) and clinical presentation (e.g. extent of injury, site of injury, etc.).

However, a therapeutically effective dose of a NELL1 peptide or agent useful in this invention is one which has a positive clinical effect on a patient or desired effect in cells as measured by the ability of the agent to enhance chondrogenic differentiation for cartilage formation or repair, as described above. The therapeutically effective dose of each peptide or agent can be modulated to achieve the desired clinical effect, while minimizing negative side effects. The dosage of the peptide or agent can be selected for an individual patient depending upon the route of administration, severity of the disease, age and weight of the patient, other medications the patient is taking and other factors normally considered by an attending physician, when determining an individual regimen and dose level appropriate for a particular patient.

Device

The composition can be formulated into an injectable or implantable device in any desired form. Some exemplary devices can be for intervertebral disc nucleus replacement, knee meniscus replacement, wrist triangular fibrocartilage replacement, temporomandibular joint replacement, articular cartilage replacement and can consist of, porous scaffold with preformed shape and attachment features to anchor to underlying bone; viscous gel with preformed shape that can be re-shaped by manual manipulation and the cured to new shape by the application of light; or low viscosity liquid that can polymerize in situ. For example, the composition can be formulated into a single mixture (or a simple mixture) for cartilage formation.

In some embodiments, the composition can be formulated into a single device containing specifically designed layers that are tissue-specific, e.g. it may be desirable to have a bone layer to anchor to the hard tissues, and then a cartilage layer immediately adjacent to the bone layer.

In some embodiments, the composition can be formulated into a single mixture allowing multiple tissues formation and self-assembly, such as polymers or monomers with amphiphilic functional groups can self-assemble into macroscopic structures.

In some embodiments, where a device including a composition described herein having a cell(s), the device can be subjected to pre-implantation stimulation. For example, the device can be placed in a mechanical bioreactor with controlled mechanical stimulation (frequency, duty cycle, amplitude, etc.); Frequency in the range of 0.01 Hz to 10,000 Hz, duty cycle above 10%; and amplitude in the range of 0.1-100% strain have reported enhanced cellular function. In some embodiments, the device described herein can be placed in a mechanical bioreactor with controlled microfluidic flow and shear stresses, which arise when at least one flow path or channel has one dimension less than 1 mm. In some embodiments, a device described herein can be implanted in a human being via direct implantation immediately following cell harvesting.

In some embodiments, the composition provided herein can form any of the following examples of devices, which illustrate, but shall not be construed to limit the claimed invention:

An injectable/implantable device containing NELL protein (with or without cells) that can be directly injected/implanted into spinal discs to promote cartilage formation;

A disc nucleus replacement device impregnated with NELL that is designed to replace the inner portion of the vertebral disc (the nucleus) or both the inner and outer portion of the disc;

An injectable/implantable device containing NELL (with or without cells) that can be directly injected into the various joint spaces (e.g., knee, temporomandibular joint, wrist) or implanted arthroscopically or openly into various joint spaces;

An injectable/implantable device containing NELL nucleic acids (with or without delivery vehicle such as a virus) (with or without cells) that can be directly injected/implanted into spinal discs to promote cartilage formation;

A disc nucleus replacement device impregnated with NELL nucleic acids (with or without delivery vehicle such as a virus) that is designed to replace the inner portion of the vertebral disc (the nucleus) or both the inner and outer portion of the disc;

An injectable/implantable device containing NELL nucleic acids (with or without delivery vehicle such as a virus) (with or without cells) that can be directly injected into the various joint spaces (e.g., knee, temporomandibular joint, wrist) or implanted arthroscopically or openly into various joint spaces;

An injectable/implantable device containing NELL protein (with or without cells) and other factors that can be directly injected/implanted into spinal discs to promote cartilage formation;

A disc nucleus replacement device impregnated with NELL and other factors that is designed to replace the inner portion of the vertebral disc (the nucleus) or both the inner and outer portion of the disc;

An injectable/implantable device containing NELL and other factors (with or without cells) that can be directly injected into the various joint spaces (e.g., knee, temporomandibular joint, wrist) or implanted arthroscopically or openly into various joint spaces;

An injectable/implantable device containing NELL nucleic acids and other factors (with or without delivery vehicle such as a virus) (with or without cells) that can be directly injected/implanted into spinal discs to promote cartilage formation;

A disc nucleus replacement device impregnated with NELL nucleic acids (with or without delivery vehicle such as a virus) that is designed to replace the inner portion of the vertebral disc (the nucleus) or both the inner and outer portion of the disc;

An injectable/implantable device containing NELL nucleic acids (with or without delivery vehicle such as a virus) (with or without cells) that can be directly injected into the various joint spaces (e.g., knee, temporomandibular joint, wrist) or implanted arthroscopically or openly into various joint spaces.

Dosages

Dosages of NELL peptides and other agents can be determined according to methods known in the art based on type of agent, the disease, and other factors such as age and gender.

In one embodiment, the dosage of NELL peptide for cartilage formation or repair generally ranges from 0.001 $pg/mm^2$ to 1 $pg/mm^2$, or more preferably from 0.001 $ng/mm^2$ to 1 $ng/mm^2$, or more preferably from 0.001 $\mu g/mm^2$ to 1 $\mu g/mm^2$, or more preferably from 0.001 $mg/mm^2$ to 1 $mg/mm^2$, or more preferably from 0.001 $g/mm^2$ to 1 $g/mm^2$, with or without a particular carrier or scaffold. In another embodiment, the dosage of NELL peptide for cartilage formation or repair generally ranges from 0.001 pg/ml to 1 pg/ml, or more preferably from 0.001 ng/ml to 1 ng/ml, or more preferably from 0.001 $\mu g/ml$ to 1 $\mu g/ml$, or more preferably from 0.001 mg/ml to 1 mg/ml, or more preferably from 0.001 g/ml to 100 g/ml, with or without a particular carrier or scaffold. In yet another embodiment, the dosage of NELL peptide for cartilage formation or repair generally ranges from 0.001 pg/kg to 1 pg/kg, or more preferably from 0.001 ng/kg to 1 ng/kg, or more preferably from 0.001 gg/kg to 1 gg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

However, because NELL peptides can have effects on in vitro osteoblast apoptosis (Zhang, X., et al., J Bone Miner Res, 2003. 18(12): p. 2126-34), NELL dosages (e.g., NELL1 dosages) that are significantly above an optimal range can not increase cartilage formation or repair. Accordingly, even more preferable dosages of NELL peptide shall not be significantly above the optimal dosage range. The even more preferable optimal dosage ranges of NELL peptides can vary according to factors such as the type, the age, the location, and the gender of a mammalian subject; the carrier or scaffold material employed; and the purity and potency of different NELL peptides. In one embodiment, the even more preferable optimal dosage ranges of NELL peptides includes but are not limited to 1 ng/mm$^2$ to 100 ng/mm$^2$, or even more preferably from 100 ng/mm$^2$ to 1000 ng/mm$^2$, or even more preferably from 1 µg/mm$^2$ to 100 µg/mm$^2$, or even more preferably from 100 µg/mm$^2$ to 1000 µg/mm$^2$. In another embodiment, the even more preferable optimal dosage ranges of NELL peptides includes but are not limited to 1 ng/ml to 100 ng/ml, or even more preferably from 100 ng/ml to 1000 ng/ml, or even more preferably from 1 µg/ml to 100 µg/ml, or even more preferably from 100 µg/ml to 1000 µg/ml. In yet another embodiment, even more preferable optimal dosage ranges of NELL peptide for cartilage formation or repair generally ranges from 1 µg/kg to 100 µg/kg, or even more preferably from 100 µg/kg to 1000 µg/kg, or even more preferably from 1 mg/kg to 100 mg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth. As used herein, the term "significantly above the optimal range" means, e.g., about 1% to about 50%, about 5% to about 50%, about 10% to about 50%, about 20% to about 50%, about 30% to about 50%, or about 40% to 50% over the optimal range.

The dosage for inhibitors of NELL peptides varies according to the type of the inhibitor, the bone or cartilage condition to be treated, prevented, or ameliorated, and the age, the location, and the gender of the mammalian subject receiving the composition containing the inhibitor. Generally, the dosage for inhibitors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for inhibitors of NELL peptides generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage for inhibitors of NELL peptides generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

The dosage for modulators of receptors of NELL peptides varies according to the type of the inhibitor, the type of receptor, the bone or cartilage condition to be treated, prevented, or ameliorated, and the age, the location, and the gender of the mammalian subject receiving the composition containing the modulators of receptors of NELL peptides. Generally, the dosage for modulators of receptors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for modulators of receptors of NELL peptides generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage for modulators of receptors of NELL peptides generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

Dosage Form

The therapeutically effective dose of an agent included in the dosage form can be selected by considering the type of agent selected and the route of administration. The dosage form can include a agent in combination with other inert ingredients, including adjutants and pharmaceutically acceptable carriers for the facilitation of dosage to the patient, as is known to those skilled in the pharmaceutical arts.

In one embodiment, the invention can include a method of treating a patient to induce cartilage formation, comprising administering NELL1 peptide at a therapeutically effective dose in an effective dosage form at a selected interval to enhance cartilage formation or repair. The method of can further comprise administering at least one secondary agent in the region where cartilage formation or repair is desired, including but not limited to TGF-beta, BMP2, BMP4, BMP7, bFGF, VEGF, PDGF, collagen, bone, bone matrix, tendon matrix or ligament matrix, chondrogenic or osteoblastic cells.

In one embodiment, a method of treating a patient to induce cartilage formation or repair can include harvesting mammalian chondrogenic cells, increasing the concentration of expression of NELL1 peptide in contact with the chondrogenic cells and administering the chondrogenic cells to a region where cartilage formation or repair is desired.

EXAMPLES

The following examples are offered to illustrate, but not to limit the claimed invention.

Example 1

Injectable Devices

An injectable device containing NELL (with or without cells) can be directly injected into spinal discs to promote cartilage formation. A disc nucleus replacement device impregnated with NELL is designed to replace the inner portion of the vertebral disc (the nucleus) or both the inner and outer portion of the disc. An injectable device containing NELL (with or without cells) can be directly injected into the various joint spaces (e.g., knee, temporomandibular joint, wrist) or implanted arthroscopically or openly into various joint spaces.

Example 2

Cartilage Differentiation, Maturation and Hypertrophy Without Necessarily Mineralization NELL1 transgenic overexpression mice were created with the rationale was that NELL1 overexpression transgenic mice would exhibit altered intramembranous or endochondral bone formation. The invention was tested with F2 progeny from NELL1 transgenic mice. Histology from various forms of NELL1 overexpression mice has demonstrated increased cartilage differentiation, maturation, and hypertrophy without necessarily mineralization in both hyaline cartilage areas (FIG. 1) and fibrocartilage areas (FIGS. 2A-2F).

Figure 3B:

Goat auricular cartilage was minced to 1×3 mm pieces and digested with 0.25% trypsin/1 mM EDTA at room temperature for 30 min, followed by 3 mg/ml collagenase II (Sigma, St Louis, Mo., USA) digestion with shaking at 37 C for 6 h. The cell suspension was filtered through a 70 mm strainer and the chondrocytes were then pelleted by centrifugation. After washing with PBS, the cells were cultured in DMEM (Gibco BRL, Grand Island, N.Y., USA) plus 10% fetal calf serum (Hyclone, Logan, Utah, USA), 100 U/ml penicillin and 100 mg/l streptomycin at 37° C. with 5% CO2. The cells were then treated/transduced with AdNELL1, AdBMP2, or AdLacZ. The in vitro transduction efficiency was assessed by staining for beta galactosidase (FIG. 3). The cells were combined with pluronic F127 (Sigma) as a common carrier for nude mice subcutaneous injection/or implantation and then examined at 2 weeks (FIG. 6) or 4 weeks (FIGS. 4,5,7-9). A total of 8 million cells were injected/implanted per site.

High-resolution micro-computed tomography (microCT), which utilized 9-20 μm resolution technology from μCT40 (Scanco Medical, Basserdorf, Switzerland) was performed on 4 week samples (FIG. 5). MicroCT data were collected at 55 kVp and 145 μA and reconstructed using the cone-beam algorithm supplied with the microCT scanner by Scanco. Visualization and reconstruction of the data were performed using the μCT Ray T3.3 and μCT Evaluation Program V5.0 provided by Scanco Medical.

Harvested samples were processed and embedded in paraffin wax. Six micron-thick sections, using a microtome (McBain Instruments, Chatsworth, Calif.), were placed on poly-L-lysine-coated Polysine microscope slides (Erie Scientific Company, Portsmouth, N.H.) and baked at 37° C. overnight. Samples were hematoxylin and eosin (H&E) stained. Additional analysis utilized alcian blue staining. Sections were stained with alcian blue solution for 30 min followed by washing in 3% glacial acetic acid followed by water. Sections were then counterstained with nuclear fast red solution and rinsed in distilled water. Finally, sections were dehydrated in alcohol and cleared in xylenes before mounting in permount (FIGS. 6 and 7).

Six-micron-thick sections were dewaxed in xylenes and rehydrated in ethanol baths. Sections were enzyme-treated for antigen retrieval with 20 μg/ml Proteinase K at 37° C. for 10 min and then blocked with 5% horse serum for 2 h at room temperature. Sections were incubated with appropriate primary antibodies at 4° C. overnight then incubated with a biotinylated anti-rabbit IgG secondary antibody (Vector Laboratories, Burlingame, Calif.) for 1 h at room temperature. Positive immunoreactivity was detected using Vectastain ABC reagents and AEC chromagen (both from Vector Laboratories) according to the manufacturer's instructions. Controls for each antibody consisted of incubation with secondary antibody in the absence of primary antibody. Sections were counterstained with hematoxylin for 2 min followed by 10 min in running water. Aqueous mounting medium was used with cover slips.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A method of increasing cartilage formation or repair comprising:
   applying a NELL-1 peptide or an expression vector encoding said NELL-1 peptide in an effective amount for cartilage formation or repair in a region where cartilage formation or repair is desired;
   optionally applying an agent to the region where cartilage formation or repair is desired; and
   at least inducing hypertrophy of chondroblast in the region where cartilage formation or repair is desired,
   wherein the NELL-1 peptide comprises the amino acid sequence set forth in SEQ ID NO: 2, 4, or 6 or a fragment of the amino acid sequence of SEQ ID NO: 2, 4, or 6 which has cartilage-forming activity.

2. The method of claim 1, wherein cartilage formation or repair includes bone healing or bone regeneration.

3. The method of claim 1, wherein the agent is selected from chondroprotective agents, anti-pain and/or anti-inflammatory agents, growth factors, cytokines, small molecules, anti-angiogenic factors, and combinations thereof.

4. The method of claim 1, wherein the agent is selected from collagen, bone matrix, ligament matrix, tendon matrix, chondrogenic cells, and osteochondroprogenitor cells.

5. A method of treating or ameliorating a cartilage related condition, comprising applying to a site in a mammalian subject a composition comprising a NELL-1 peptide or an expression vector encoding said NELL-1 peptide in an effective amount for cartilage formation or repair;
   wherein the NELL-1 peptide comprises the amino acid sequence set forth in SEQ ID NO: 2, 4, or 6 or a fragment of the amino acid sequence of SEQ ID NO: 2, 4, or 6 which has cartilage-forming activity.

6. The method of claim 5, wherein the composition further comprises a second agent selected from the group consisting of chondroprotective agents, anti-pain and/or anti-inflammatory agents, growth factors, cytokines, small molecules, anti-angiogenic factors and combinations thereof.

7. A method of treating or ameliorating a cartilage related condition, comprising applying to a site in a mammalian subject an implant comprising a substrate having a surface, wherein at least a portion of the surface includes a composition that comprises a NELL-1 peptide or an expression vector encoding said NELL-1 peptide in an effective amount for cartilage formation or repair;
    wherein the NELL-1 peptide comprises the amino acid sequence set forth in SEQ ID NO: 2, 4, or 6 or a fragment of the amino acid sequence of SEQ ID NO: 2, 4, or 6 which has cartilage-forming activity.

8. The method of claim 7, wherein the composition further comprises a second agent selected from the group consisting of chondroprotective agents, anti-pain and/or anti-inflammatory agents, growth factors, cytokines, small molecules, anti-angiogenic factors and combinations thereof.

\* \* \* \* \*

UNITED STATES PATENT AND TRADEMARK OFFICE
CERTIFICATE OF CORRECTION

PATENT NO. : 7,687,462 B2
APPLICATION NO. : 11/594510
DATED : March 30, 2010
INVENTOR(S) : Kang Ting et al.

Page 1 of 1

It is certified that error appears in the above-identified patent and that said Letters Patent is hereby corrected as shown below:

In Column 1, lines 38-43, please delete the statement:

"Part of this work was supported by NIH/NIDR grant number DE9400 and CRC/NIH grant number RR00865, NIH/NIDCR RO3 DE 014649-01, NIH/NIDCR K23DE00422, NIH DE016107-01, and NIH/SBIR R43-DE016781-01. The Government of the United States of America has certain rights in this invention."

and insert the statement:

-- This invention was made with Government support under Grant Nos. DE094001, RR000865, DE000422, DE014649, DE016781, and DE016107 awarded by the National Institutes of Health. The Government has certain rights in this invention. --

Signed and Sealed this

Twentieth Day of July, 2010

David J. Kappos
*Director of the United States Patent and Trademark Office*